(12) United States Patent
El-Agnaf

(10) Patent No.: US 10,208,111 B2
(45) Date of Patent: Feb. 19, 2019

(54) ALPHA-SYNUCLEIN ANTIBODIES AND USES THEREOF

(71) Applicant: United Arab Emirates University, Al-Ain (AE)

(72) Inventor: Omar El-Agnaf, Doha (QA)

(73) Assignee: United Arab Emirates University, Al-Ain (AE)

( * ) Notice: Subject to any disclaimer, the term of this patent is extended or adjusted under 35 U.S.C. 154(b) by 0 days.

(21) Appl. No.: 15/355,543

(22) Filed: Nov. 18, 2016

(65) Prior Publication Data

US 2017/0190765 A1 Jul. 6, 2017

Related U.S. Application Data

(60) Division of application No. 14/138,347, filed on Dec. 23, 2013, now Pat. No. 9,534,044, which is a continuation of application No. 13/781,158, filed on Feb. 28, 2013.

(51) Int. Cl.
*C07K 16/18* (2006.01)
*G01N 33/68* (2006.01)

(52) U.S. Cl.
CPC ......... *C07K 16/18* (2013.01); *G01N 33/6896* (2013.01); *C07K 2317/33* (2013.01); *C07K 2317/34* (2013.01); *C07K 2317/565* (2013.01); *C07K 2317/92* (2013.01)

(58) Field of Classification Search
CPC .......... A61K 51/1018; A61K 2039/505; A61K 39/0007; A61K 38/1709; A61K 39/00; A61K 49/14; A61K 49/16; C07K 16/18; C07K 2317/92; C07K 2317/70; C07K 14/47; C07K 2317/76; C07K 16/00; C07K 2317/565; G01N 33/6896; G01N 2800/2821; G01N 2800/2814; G01N 2333/4709; G01N 2800/2828; G01N 2800/28; G01N 2800/7047; G01N 33/5058; G01N 33/6854; Y10S 530/839
See application file for complete search history.

(56) References Cited

U.S. PATENT DOCUMENTS

| | | | | |
|---|---|---|---|---|
| 5,948,658 | A * | 9/1999 | Landry ............... | C12N 9/0002 435/188.5 |
| 7,785,593 | B2 * | 8/2010 | Barske ................. | C07K 14/47 424/130.1 |
| 2008/0138336 | A1 * | 6/2008 | Damschroder .... | C07K 16/2896 424/133.1 |

FOREIGN PATENT DOCUMENTS

| | | | |
|---|---|---|---|
| DE | 102011008153 | 7/2012 | |
| EP | 0585939 A2 * | 3/1994 | ......... C07K 14/7151 |
| WO | WO-2005005638 A2 * | 1/2005 | ........... C07K 14/715 |
| WO | WO-2005051307 A2 * | 6/2005 | ............. C07K 16/24 |
| WO | WO 2009/027690 | 3/2009 | |
| WO | WO 2010/069603 | 6/2010 | |
| WO | WO-2011016238 A1 * | 2/2011 | ............. C07K 16/18 |
| WO | WO 2011/104696 | 9/2011 | |
| WO | WO 2012/177972 | 12/2012 | |

OTHER PUBLICATIONS

Li et al. Cell culture processes for monoclonal antibody production. MAbs. Sep.-Oct. 2010;2(5):466-79. Epub Sep. 1, 2010.*
Barkhordarian et al., *Isolating recombinant antibodies against specific protein morphologies using atomic force microscopy and phage display technologies*, 19(11) Protein Engineering, Design & Selection 497-502 (2006).
Kovacs et al., *An antibody with high reactivity for disease-associated α-synuclein reveals extensive brain pathology*, 124 Acta Neuropathol 37-50 (2012).
Lindersson et al., *Proteasomal Inhibition by α-Synuclein Filaments and Oligomers*, 279(13) The Journal of Biology Chemistry 12924-12934 (2004).
Extended European Search Report dated Sep. 26, 2016, in corresponding EP Patent Application No. 14756906.5.
Paleologou et al., *Detection of elevated levels of soluble α-synuclein oligomers in post-mortem brain extracts from patients with dementia with Lewy bodies*, 132 Brain 1093-1101 (2009).
Fagerqvist et al., *Monoclonal antibodies selective for a-synuclein oligomers/protofibrils recognize brain pathology in Lewy body disorders and transgenic mice expressing the disease-causing A30P mutation*, 10.1111/jnc.12175, International Society for Neurochemistry, J. Neurochem. (2013) (Accepted Article).
Perring et al., Multimodal techniques for diagnosis and prognosis of Alzheimer's disease 461(7266) Nature 916-922 (Oct. 15, 2009).
Vicerks, *A vaccine against Alzheimer's disease: developments to date*, 19(7) Drugs Aging 487-494 (2002).
Kayed et al., *Fibril specific, conformation dependent antibodies recognize a generic epitope common to amyloid fibrils and fibrillar oligomers that is absent in prefibrillar oligomers*, 2 Mol. Neurodegener 18 (Sep. 26, 2007).

* cited by examiner

*Primary Examiner* — Gregory S Emch
(74) *Attorney, Agent, or Firm* — Buchanan Ingersoll & Rooney PC

(57) ABSTRACT

The invention describes antibodies having a high affinity for aggregated forms of α-synuclein and a low affinity for monomeric forms of α-synuclein. The antibodies are useful in the diagnosis of neurodegenerative diseases.

16 Claims, 30 Drawing Sheets
Specification includes a Sequence Listing.

Figure 8

```
         10          20          30          40          50          60
MDVFMKGLSK  AKEGVVAAAE  KTKQGVAEAA  GKTKEGVLYV  GSKTKEGVVH  GVATVAEKTK 70          80          90         100         110         120
EQVTNVGGAV  VTGVTAVAQK  TVEGAGSIAA  ATGFVKKDQL  GKNEEGAPQE  GILEDMPVDP 130         140
DNEAYEMPSE  EGYQDYEPEA
```

ALPHA-SYNUCLEIN ANTIBODIES AND USES THEREOF

CROSS-REFERENCE TO RELATED APPLICATIONS

This application is a Continuation-In-Part of U.S. patent application Ser. No. 13/781,158, filed on Feb. 28, 2013, the content of which is hereby expressly incorporated by reference herein in its entirety for all purposes

FIELD OF THE INVENTION

The invention relates to the antibodies or fragments thereof that have a high binding affinity for α-synuclein aggregates (e.g. amyloid fibrils, protofibrils or oligomers) and low binding affinity for α-synuclein monomers. The invention is also directed to the use of these antibodies and fragments in the diagnosis, treatment and prevention of neuropathologies associated with α-synuclein.

BACKGROUND

Synucleins are a family of small proteins, about 14 kDa that are expressed at high levels in nervous tissues. The three members of the family are α-, β-, and γ-synucleins.

α-Synuclein is expressed mainly in brain tissues and is primarily located at the presynpatic terminal of neurons. The primary structure of the human form of α-synuclein consists of a 140 amino acid polypeptide. The wild type sequence of human α-synuclein can be found in FIG. 20 (SEQ ID NO:49). α-Synuclein normally exists as an soluble monomeric protein but can adopt several different folded confirmations depending on its environment. Monomeric α-synuclein can also aggregate into oligomers and into higher molecular weight insoluble fibrils.

Diseases associated with abnormalities in synucleins are often referred to as the synucleinopathies. Synucleinopathies include the neurodegenerative conditions, Parkinson's disease (PD), dementia with Lewy bodies (DLB) and multiple system atrophy (MSA). In synucleinopathies it has been shown that soluble α-synuclein oligomers in brain homogenates of PD and DLB are elevated compared to normal brains. In addition the neuropathologic lesions (Lewy bodies) that often characterise the end stage of PD and DLB have largely been found to be composed of fibrillar α-synuclein deposits.

Commercially available α-synuclein antibodies are known, and are widely used for characterising PD pathology in the brain. However such antibodies are non-specific and recognise both the monomeric and the aggregated forms of α-synuclein, and may not recognise all aggregated forms of α-synuclein.

Known α-synuclein antibodies include Syn-1 (BD Biosciences) and mAb 211 (Santa Cruz Biotechnology), which are known to bind equally to monomeric and aggregated forms of α-synuclein.

WO2011/104696 discloses antibodies that specifically recognise the protofibril forms of α-synuclein. These antibodies exhibit low binding affinity to α-synuclein fibrils and monomers.

SUMMARY OF THE INVENTION

The invention is directed to antibodies and fragments thereof having a high binding affinity for α-synuclein aggregates and a low binding affinity for monomeric forms of α-synuclein.

The invention is also directed to compositions comprising such an antibody or fragment thereof and to methods of using the antibody or fragment to detect the presence of α-synuclein aggregates and their use in the diagnosis of diseases associated with α-synuclein.

In further embodiments the invention is directed to compositions comprising such an antibody or fragment thereof and methods using the antibody or fragment to treat or prevent diseases associated with α-synuclein pathologies.

Using antibodies specific for α-synuclein aggregates could help reveal novel pathologies for PD and other synucleinopathies.

By producing antibodies specific to the aggregates of α-synuclein and which have low binding affinity to α-synuclein monomers the present invention provides new tools to follow the progression of neurodegenerative diseases associated with α-synuclein. The antibodies of the invention also provide antibodies that could be used in the treatment of diseases associated with α-synuclein.

BRIEF DESCRIPTION OF THE DRAWINGS

The invention will now be described by way of example with reference to the accompanying drawings:

FIG. 8 shows the Pepscan results for the mAbs Syn-F1, Syn-F2, Syn-O1, Syn-O2, Syn-O3 and Syn-O4, and Syn-1 antibody (as a control) by dot blot for epitope determination as described in Example 7.

DETAILED DESCRIPTION

Figure 1A:
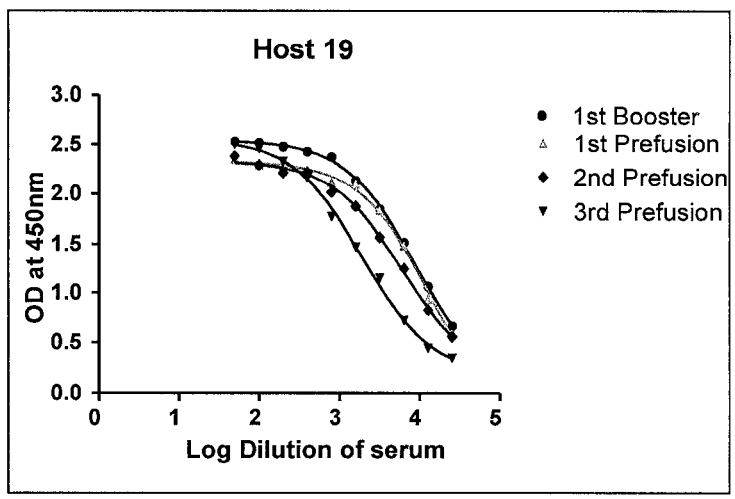
FIGS. 1A-1F show the results of the titer check for the hosts immunized with α-synuclein fibrils (hosts 19 (FIG. 1A), 22 (FIG. 1B), and 23 (FIG. 1C)) and α-synuclein oligomers (hosts 210 (FIG. 1D), 211 (FIG. 1E) and 212 (FIG. 1F)) as described in Example 1.
Figure 1B:
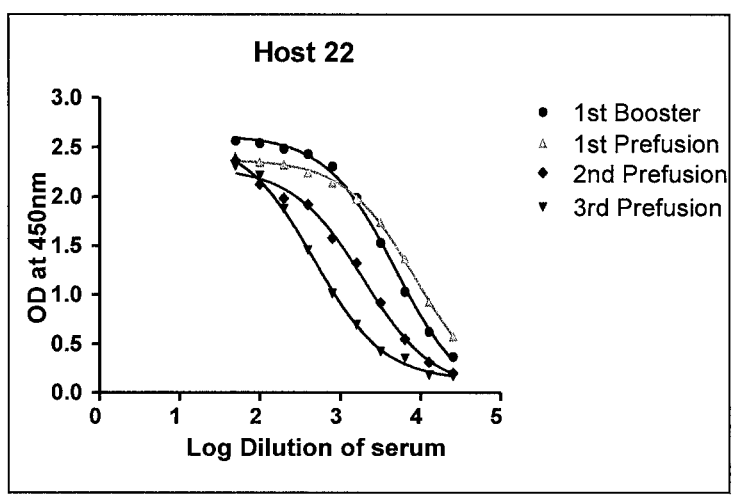
Figure 1C:
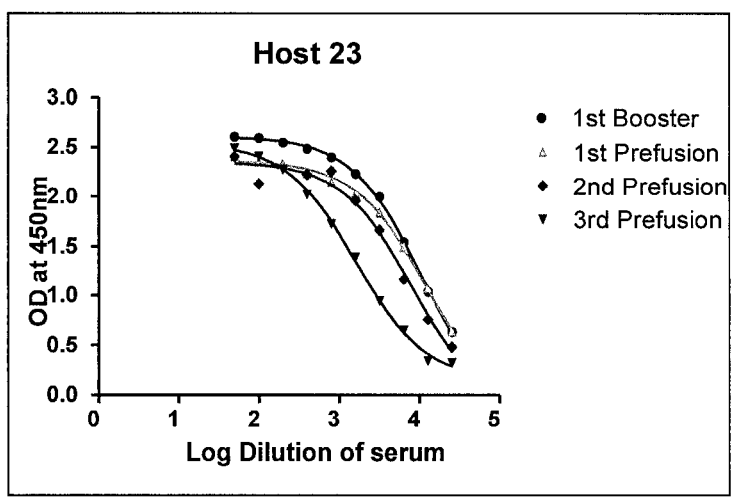
Figure 1D:
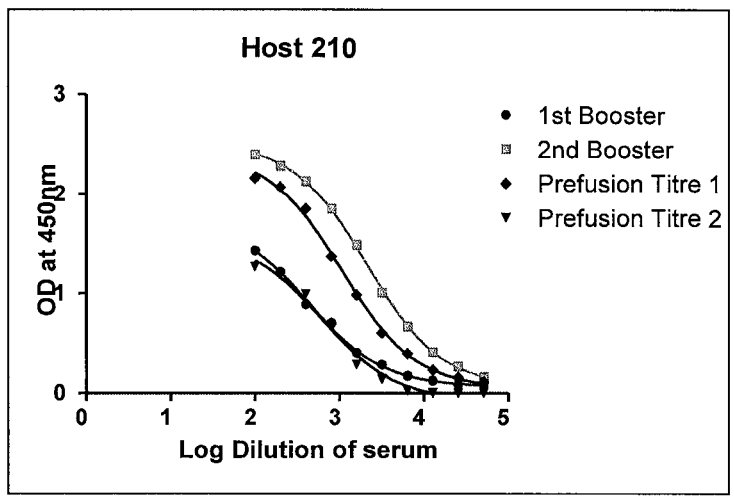
Figure 1E:
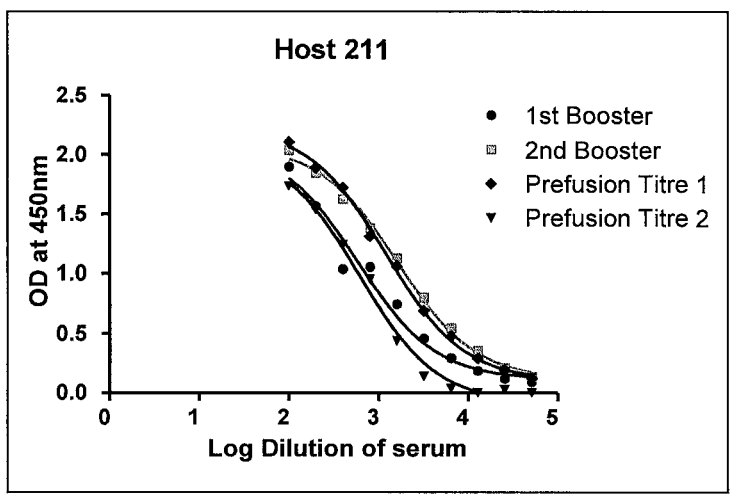
Figure 1F:
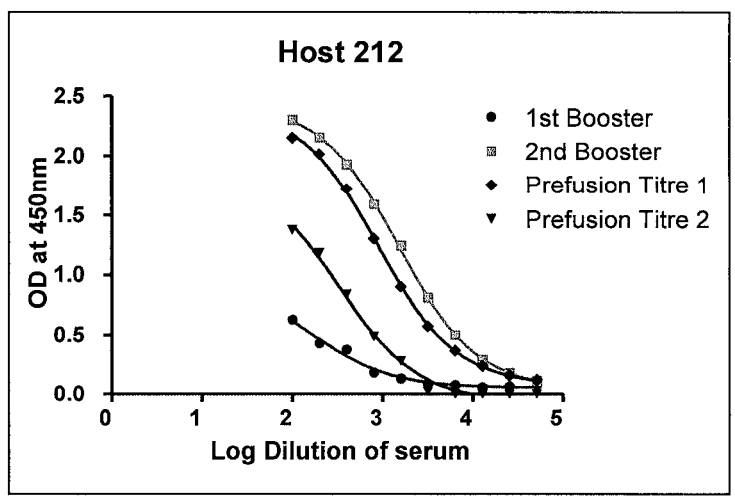

The invention relates to antibodies having high binding affinity to α-synuclein aggregates and low binding affinity to α-synuclein monomers. The antibodies have an increased affinity to bind to α-synuclein aggregates compared to monomeric α-synuclein forms.

In one embodiment, the invention relates to antibodies or fragments thereof having a high binding affinity for α-synuclein aggregates and low binding affinity for α-synuclein monomers.

Unless otherwise stated the term α-synuclein aggregates is intended to cover early soluble aggregates forms of α-synuclein (such as low and high molecular weight soluble oligomers, including protofibrils) and mature insoluble aggregates forms of α-synuclein (such as mature fibrils). In particular the antibodies and fragments thereof have high binding affinity to α-synuclein fibrils and high binding affinity to α-synuclein oligomers.

Having a high affinity for α-synuclein aggregates means that the antibodies or fragments exhibit a dissociation constant, Kd of less of than $10^{-7}$M for α-synuclein aggregates. Preferably the antibody exhibits a Kd of less than $10^{-8}$M, or less than $10^{-9}$M, or even more preferably a Kd of less than $10^{-10}$M, or even less than $10^{-11}$M. Preferably the α-synuclein is human α-synuclein.

Fibrils are insoluble higher molecular weight aggregated forms of α-synuclein.

Soluble oligomeric forms of α-synuclein come in a variety of sizes and morphologies and includes dimer, trimers, tetramers and multimers. Protofibrils are an intermediate step in the pathway to the formation of the α-synuclein fibrils from the monomeric forms. When the term oligomeric forms of α-synuclein is used this is also intended to include protofibrils.

A fragment thereof of the antibodies means active fragments thereof, i.e. fragments having the same characteristics that are used for the definition of an antibody according to the invention, namely high affinity for α-synuclein aggregates and low binding affinity to α-synuclein monomers. For convenience when the term antibody is used, fragments thereof exhibiting the same characteristic are also being considered.

Having a low binding affinity for α-synuclein monomers means that the binding of an antibody or fragment to α-synuclein monomers is at least 100 times less than the binding to α-synuclein aggregates, preferably about 500 less, or about a 1000 times lower binding affinity to α-synuclein monomers compared to α-synuclein aggregates. In one embodiment the antibody or fragment thereof has a dissociation constant, Kd, of more than $10^{-5}$M for monomeric α-synuclein.

In one embodiment the antibodies may have a higher affinity for α-synuclein fibrils than for oligomeric forms of α-synucleins.

The binding affinities of the antibodies can be determined by using a variety of methods recognised in the art including, isothermal calorimetry and surface plasmon resonance based approaches, for example as described in Example 6. Binding can also be evaluated using immunoassays such as ELISA or RIAs. Preferably the binding affinity is determined using surface plasmon resonance assays using a BIACore™ X-100.

In one embodiment the antibodies are conformational antibodies. The antibodies recognise conformational epitopes, i.e. the epitope the antibody recognises includes the tertiary structure of the aggregates of α-synuclein. In one embodiment the antibodies bind more strongly to the α-synuclein fibrils than to any of the linear peptide epitopes as described in Table 5. In particular the binding of the antibodies is at least 100 times higher to the α-synuclein fibrils than to the linear peptide epitopes as described in Table 5, preferably 500 times more, or preferably 1000 times more.

The antibodies of the invention may bind weakly to a linear epitope within the amino acid region 127-140 of α-synuclein. By binding weakly means that the binding affinity of the antibodies of the invention is at least 100 less to a linear epitope within the amino acid region 127-140 of α-synuclein than the binding affinity of the antibodies to α-synuclein aggregates, in particular at least 100 times less than to α-synuclein fibrils. Preferably the binding affinity to a linear epitope within the amino acid region 127-140 of α-synuclein is 1000 times less than to the binding affinity of the antibodies to α-synuclein aggregates. In one embodiment the antibodies do not recognise or bind to a linear epitope of α-synuclein.

In one embodiment the epitope recognised by the antibody comprises a C-terminal region of α-synuclein. By recognising an epitope comprising a C-terminal region of α-synuclein means that at least part of the epitope the antibody has the ability to bind to includes at least part of the C-terminal region of α-synuclein.

In one embodiment the antibodies of the invention can also bind to aggregated forms of phosphorylated α-synuclein. The antibodies exhibit low binding affinity to monomeric forms of phosphorylated α-synuclein as compared to aggregated forms of phosphorylated α-synuclein, e.g. the binding affinity of the antibodies is at least 100 times less, preferably 500 times less, more preferably 1000 times less to monomeric phosphorylated α-synuclein forms as compared to aggregated phosphorylated α-synuclein. Phosphorylation of the α-synuclein can occur at Ser129.

The antibodies of the invention also exhibit low binding affinity to other amyloid proteins including, β-synuclein, γ-synuclein monomers, IAPP (islet amyloid polypeptide), β-amyloid monomers, Tau and ABri, e.g. the binding affinity of the antibodies is at least 100 times less to one or more of these peptide/proteins than that to the α-synuclein aggregates.

In one embodiment the binding affinity of the α-synuclein aggregate antibodies of the invention is at least 100 times less, preferably 1000 less to β-synuclein than to α-synuclein aggregates. In particular the binding affinity of the antibodies is at least 100 times less, preferably 1000 less to β-synuclein than the binding affinity to α-synuclein fibrils.

In one embodiment the binding affinity of the α-synuclein aggregate antibodies of the invention is at least 100 times less, preferably 1000 less to γ-synuclein than to α-synuclein aggregates. In particular the binding affinities of the antibodies are at least 100 times less, preferably 1000 less to γ-synuclein than to α-synuclein fibrils.

A further embodiment of the invention provides antibodies comprising defined amino acid sequences of the CDR1-3 regions on the variable heavy (VH) and variable light (VL) chains.

In one embodiment of the invention an antibody comprises a variable heavy chain (VH), wherein the VH comprises the amino acid sequence as shown in SEQ ID NO:2, SEQ ID NO: 6, or SEQ ID NO: 10.

The antibody or fragment can comprise an immunoglobin light chain variable region (VL), wherein the VL comprises the amino acid sequence as shown in SEQ ID NO:4, SEQ ID NO: 8, or SEQ ID NO: 12.

In particular the antibody or fragment comprises an immunoglobin heavy chain variable region (VH) and an immunoglobin light chain variable region (VL), wherein:
the VH comprises the amino acid sequence as shown in SEQ ID NO:2 and the VL comprises the amino acid sequence as shown in SEQ ID NO:4;
the VH comprises the amino acid sequence as shown in SEQ ID NO:6 and the VL comprises the amino acid sequence as shown in SEQ ID NO: 8; or
the VH comprises the amino acid sequence as shown in SEQ ID NO:10 and the VL comprises the amino acid sequence as shown in SEQ ID NO: 12.

In one specific embodiment the antibody or fragment thereof can comprise a VH chain wherein:

the CDR1 region has the amino acid sequence of SEQ ID NO:16, SEQ ID NO:28, or SEQ ID NO: 40;
the CDR2 region has the amino acid sequence of SEQ ID NO:17, SEQ ID NO:29, or SEQ ID NO:41; and
the CDR3 region has the amino acid sequence of SEQ ID NO:18, SEQ ID NO:30, or SEQ ID NO: 42.

In particular the antibody or binding fragments thereof comprises a VH chain wherein the CDR1 region has the amino acid sequence of SEQ ID NO:16, the CDR2 region has the amino acid sequence of SEQ ID NO:17, and the CDR3 region has the amino acid sequence of SEQ ID NO:18.

In particular the antibody or binding fragments thereof comprises a VH chain wherein the CDR1 region has the amino acid sequence of SEQ ID NO:28, the CDR2 region has the amino acid sequence of SEQ ID NO:29, and the CDR3 region has the amino acid sequence of SEQ ID NO:30.

In particular the antibody or binding fragments thereof comprises a VH chain wherein the CDR1 region has the amino acid sequence of SEQ ID NO:40, the CDR2 region has the amino acid sequence of SEQ ID NO:41, and the CDR3 region has the amino acid sequence of SEQ ID NO:42.

In a further embodiment the antibody or fragment thereof comprises a VL chain wherein:
the CDR1 region has the amino acid sequence SEQ ID NO:22, SEQ ID NO:34, or SEQ ID NO: 46;
the CDR2 region has the amino acid sequence of SEQ ID NO:23, SEQ ID NO:35, or SEQ ID NO: 47; and
the CDR3 region has the amino acid sequence of SEQ ID NO:24, SEQ ID NO:36, or SEQ ID NO: 48.

In particular the antibody or fragment thereof comprises a VL chain wherein the CDR1 region has the amino acid sequence SEQ ID NO:22, the CDR2 region has the amino acid sequence of SEQ ID NO:23; and the CDR3 region has the amino acid sequence of SEQ ID NO:24.

In particular the antibody or fragment thereof comprises a VL chain wherein the CDR1 region has the amino acid sequence SEQ ID NO:34, the CDR2 region has the amino acid sequence of SEQ ID NO:35; and the CDR3 region has the amino acid sequence of SEQ ID NO:36.

In particular the antibody or fragment thereof comprises a VL chain wherein the CDR1 region has the amino acid sequence SEQ ID NO:46; the CDR2 region has the amino acid sequence of SEQ ID NO:47; and the CDR3 region has the amino acid sequence of SEQ ID NO:48.

In one embodiment the antibody or fragment thereof comprises:
a VH chain wherein the CDR1 region has the amino acid sequence of SEQ ID NO:16, the CDR2 region has the amino acid sequence of SEQ ID NO:17, and the CDR3 region has the amino acid sequence of SEQ ID NO:18; and
a VL chain wherein the CDR1 region has the amino acid sequence SEQ ID NO:22, the CDR2 region has the amino acid sequence of SEQ ID NO:23; and the CDR3 region has the amino acid sequence of SEQ ID NO:24.

In particular the antibody or binding fragments thereof comprises:
a VH chain wherein the CDR1 region has the amino acid sequence of SEQ ID NO:28, the CDR2 region has the amino acid sequence of SEQ ID NO:29, and the CDR3 region has the amino acid sequence of SEQ ID NO:30; and
a VL chain wherein the CDR1 region has the amino acid sequence SEQ ID NO:34; the CDR2 region has the amino acid sequence of SEQ ID NO:35; and the CDR3 region has the amino acid sequence of SEQ ID NO:36.

In particular the antibody or binding fragments thereof comprises:

a VH chain wherein the CDR1 region has the amino acid sequence of SEQ ID NO:40, the CDR2 region has the amino acid sequence of SEQ ID NO:41, and the CDR3 region has the amino acid sequence of SEQ ID NO:42; and a VL chain wherein the CDR1 region has the amino acid sequence SEQ ID NO:46; the CDR2 region has the amino acid sequence of SEQ ID NO:47; and the CDR3 region has the amino acid sequence of SEQ ID NO:48.

Thus in one embodiment an antibody or binding fragment thereof according to the invention is characterised by having six CDR sequences (VH-CDR1, VH-CDR2, VH-CDR3, VL-CDR1, VL-CDR2 and VL-CDR3) independently selected from each of the following respective groups of CDR sequences, in any combination, in Table A.

TABLE A

| VH-CDR1 SEQ ID NOs | VH-CDR2 SEQ ID NOs | VH-CDR3 SEQ ID NOs | VL-CDR1 SEQ ID NOs | VL-CDR2 SEQ ID NOs | VL-CDR3 SEQ ID NOs |
|---|---|---|---|---|---|
| 16 | 17 | 18 | 22 | 23 | 24 |
| 28 | 29 | 30 | 34 | 35 | 36 |
| 40 | 41 | 42 | 46 | 47 | 48 |

Further provided is an isolated antibody or antigen binding fragment thereof that specifically binds to human α-synuclein, comprising a VH and a VL, where the VL comprises a polypeptide sequence at least 90%, 95% or 100% identical to SEQ ID NO: 2 or SEQ ID NO:6 or SEQ ID NO:10. Also provided is an isolated antibody or antigen binding fragment thereof that specifically binds to human α-synuclein, comprising a VH and a VL, where the VL comprises a polypeptide sequence at least 90%, 95% or 100% identical to SEQ ID NO: 4 or SEQ ID NO:8 or SEQ ID NO:12.

Whether any particular polypeptide is at least 90% or 95% identical to another polypeptide can be determined using methods and computer programs/software known in the art. These variant polypeptides retain essentially the same properties of the polypeptides having the corresponding parent sequence. Such variants have conservative substitutions with respect to the reference compound, e.g. changes between amino acids of broadly similar molecular properties. For example amino acid substitutions leading to conservative substitutions or changes at "non-essential" amino acids may be made. Amino acid substitutions can include replacement of one or more amino acids with a naturally occurring or non-natural amino acid. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

The polypeptides may be fused in-frame or conjugated to a linker or other sequence. The Polypeptide may comprise a fusion protein for example comprising a portion encoding an α-synuclein antibody or fragment thereof and at least one heterologous portion Further provided are isolated polynucleotides encoding the antibodies or antigen binding fragments thereof, for example a nucleic acid which encodes for one or more CDRs, or a variable heavy chain or variable light chain region of the α-synuclein antibodies described herein. Nucleic acid includes DNA and RNA.

One aspect of the invention provides a polynucleotide encoding the VH chain of the α-synuclein antibody described herein. In particular one embodiment of the invention provides an isolated polynucleotide comprising a nucleic acid encoding the amino acid sequence of SEQ ID NO: 2; SEQ ID NO:6, or SEQ ID NO:10. A further embodiment provides a polynucleotide comprising the nucleic acid sequence of SEQ ID NO:1; SEQ ID NO:5 or SEQ ID NO:9.

Another aspect of the invention provides a polynucleotide encoding the VL chain of the α-synuclein antibody. In one embodiment the polynucleotide comprises a nucleic acid encoding the amino acid sequence of SEQ ID NO:4; SEQ ID NO:8, or SEQ ID NO:12. A further embodiment provides a polynucleotide comprising the nucleic acid sequence of SEQ ID NO:3; SEQ ID NO:7 or SEQ ID NO:11.

In one embodiment a polynucleotide encodes the CDR1, CDR2 and/or CDR3 region of the heavy chain of the α-synuclein antibodies. The polynucleotide can comprise the nucleic acid sequence of SEQ ID NO:13, SEQ ID NO:14, SEQ ID NO:15, SEQ ID NO:25, SEQ ID NO:26, SEQ ID NO:27, SEQ ID NO:37, SEQ ID NO: 38, and/or SEQ ID NO: 39.

Also provide d is a polynucleotide encoding the CDR1, CDR2 and/or CDR3 region of the light chain of the α-synuclein antibodies. The polynucleotide can comprise the nucleic acid sequence of SEQ ID NO:19, SEQ ID NO:20, SEQ ID NO:21, SEQ ID NO:31, SEQ ID NO:32, SEQ ID NO:33, SEQ ID NO:43, SEQ ID NO:44, and/or SEQ ID NO:45.

In one embodiment an antibody or binding fragment thereof according to the invention is characterised by having six CDR sequences (VH-CDR1, VH-CDR2 VH-CDR3, VL-CDR1, VL-CDR2 and VL-CDR3) each region encoded by a polynucleotide having a sequence independently selected from each of the following respective groups of CDR sequences, in any combination, from Table B:

TABLE B

| VH-CDR1 SEQ ID NOs | VH-CDR2 SEQ ID NOs | VH-CDR3 SEQ ID NOs | VL-CDR1 SEQ ID NOs | VL-CDR2 SEQ ID NOs | VL-CDR3 SEQ ID NOs |
|---|---|---|---|---|---|
| 13 | 14 | 15 | 19 | 20 | 21 |
| 25 | 26 | 27 | 31 | 32 | 33 |
| 37 | 38 | 39 | 43 | 44 | 45 |

Also provided is a polynucleotide comprising a nucleic acid sequence for the VH-CDR1, VH-CDR2 and VH-CDR3 regions, each independently selected from each of the respective groups of VH-CDR sequences, in any combination, from Table B:

Further provided is a polynucleotide comprising a nucleic acid sequence for the VL-CDR1, VL-CDR2 and CL-CDR3 regions, each independently selected from each of the respective groups of VL-CDR sequences, in any combination, from Table B Also provided are polynucleotide variants of the polynucleotide sequences defined herein. Polynucleotide variants may have substantial identity to a polynucleotide sequence encoding an α-synuclein antibody or fragment defined herein. Typically, polynucleotide variants will contain one or more substitutions, additions, deletions and/or insertions, preferably such that the binding affinity of the antibody encoded by the variant polynucleotide is not substantially diminished relative to an antibody encoded by a polynucleotide sequence specifically described herein. For example nucleotide substitutions leading to conservative substitutions or changes at "non-essential" amino acid residues in the encoded polypeptide may be made. Whether any particular polynucleotide is substantial identical to another can be determined using methods and computer programs/software known in the art.

The polynucleotides encoding at least the variable domain of the light and/or heavy chain can encode the variable domain of both immunoglobin chains or only one. One embodiment provides expression vectors comprising the polynucleotide.

A further embodiment relates to a host cell comprising the expression vector. Preferably the host cell is isolated. In one embodiment the host cell is a non-human cell. The expression vector can comprise nucleic acid sequences that direct and/or control expression of the inserted polynucleotide. Such nucleic acid sequences can include regulatory sequence, including promoter sequences, terminator sequences, polyadenylation sequences, and enhancer sequences. Systems for cloning and expression of a polypeptide in a variety of cells are well known.

Examples of antibodies according to the invention have been developed by traditional hybridoma techniques. The antibodies may be polyclonal or monoclonal. In a specific embodiment the antibodies are monoclonal.

Typically the antibody is a mammalian antibody, such as primate, human, rodent, rabbit, ovine, porcine or equine antibody. The antibody can be any class or isotype antibody, for example IgM or IgG. Preferably the antibody is IgG.

In another aspect of the invention the antibodies can be used as diagnostic tools for detecting the presence of α-synuclein aggregates in a sample. The antibodies may be used for monitoring and/or diagnosing a neurodegenerative disorder associated with α-synuclein in an individual.

These antibodies may be suitable as diagnostic tools for neurodegenerative disorders associated with α-synuclein, including but not limited to Parkinson's disease, dementia with Lewy bodies and other α-synuclein related neurodegenerative disorders.

In one embodiment the invention relates to a method of detecting α-synuclein aggregates comprising the steps of:
adding the antibody or fragment thereof to a biological sample; and
detecting the presence of a complex formed between α-synuclein aggregates and the antibody or fragment.

The detection of complexes indicates the presence of α-synuclein aggregates in the sample.

The method can further comprise the step of measuring the level of complex formed and comparing the levels to a reference level. The reference level will typically be calculated from a sample from an individual known not to have an α-synuclein pathology (a "normal individual") or from an earlier test of a sample taken from the same individual being tested.

The method can detect fibrils and oligomers of α-synuclein.

The method can be carried out in vitro on a tissue or biological fluid sample. The sample obtained from the individual to be tested, can for example be cerebrospinal fluid, (CSF), blood, urine, saliva, or brain, gut, colon, skin or salivary gland tissues. In particularly preferred methods the sample is a CSF sample. In another preferred method the sample is a brain tissue sample.

The sample is combined with the antibody for a time and under conditions effective to allow binding of the antibody to α-synuclein aggregates in the sample.

The sample may be processed prior to being assayed using standards methods. In one embodiment the tissue sample under goes no pre-treatment before testing with the antibody. By pre-treatment it is meant the tissue sample obtained is not subjected to any treatment such as, autoclaving, formic acid and/or proteinase K treatment.

Standard methods known in the art may be used to detect and/or measure the level of the complex formed between the antibodies and α-synuclein aggregates in the sample.

Analysis for the presence of α-synuclein can be conducted by a method such as radioimmunoassay, an enzyme-linked immunosorbant assay (ELISA), a sandwich immunoassay, a fluorescent immunoassay, a precipitation reaction, a gel immunodiffusion assay, an agglutination assay, a protein A immunoassay, an immunoelectrophoresis assay, an electrophoresis, western blotting. Other suitable techniques able to measure and/or detect the presence of α-synuclein in the sample to be tested can also be used.

In one embodiment the antibodies may be coated onto a surface, such as a microwell plate or diagnostic test strip, and the sample added to the antibody and allowed to combined under conditions effective to allow binding. The presence of the complex can then be detected.

In a preferred method an ELISA assay is used to detect and/or quantify the amount of α-synuclein aggregates. In one embodiment the invention is directed to a sandwich ELISA comprising adding the sample to be tested to a microplate, where the surface of the microplate has been coated with an antibody according to the invention; allowing any α-synuclein aggregates present in the sample to bind to the antibodies; and detecting the presence of any antibody/α-synuclein aggregate complexes. Detection can be carried out using labelled antibodies that bind α-synuclein.

The methods can be used for the diagnosis of neurodegenerative diseases and/or monitoring the progression of a neurodegenerative disease. The amount and/or size of any α-synuclein aggregates can be detected.

The neurodegenerative disease can include but is not limited to Parkinson's disease, dementia, Alzheimer's disease, Down's syndrome, multiple-system atrophy, psychosis, schizophrenia or Creutzfeldt-Jakob disease. The dementia may be dementia with Lewy bodies.

The invention also relates to a method of diagnosing a neurodegenerative disease associated with α-synuclein. The method comprises administering an antibody of the invention to an individual and detecting the presence or absence of α-synuclein aggregates. The presence or absence of a complex formed between the α-synuclein aggregates and the antibody can be detected.

The presence of α-synuclein aggregates indicates that the individual has a neurodegenerative disease and the absence of α-synuclein aggregates indicates that the subject does not have the neurodegenerative disease.

In one embodiment the method of diagnosing a neurodegenerative disease associated with α-synuclein comprises: adding an antibody of the invention to a sample from an individual; detecting the presence of a complex formed between the α-synuclein aggregates and the antibody; and determining whether or not the individual has a neurodegenerative disease associated with α-synuclein.

Determining whether or not the individual has a neurodegenerative disease can comprise comparing the levels of the complex formed in a sample with a reference level and determining whether the levels of complexes formed in the sample have decreased relative to a reference level.

The method can further comprise administering to the individual a therapeutically effective amount of an agent to treat the neurodegenerative disease.

In a further embodiment a method of monitoring the progress of a neurodegenerative disease associated with α-synuclein comprises: adding an antibody of the invention to a sample from an individual; detecting the presence of a complex formed between the α-synuclein aggregates and the antibody; and comparing the levels of the complex formed in a sample with a reference level.

The method can further comprise altering the treatment regime of the individual based on the comparison of the detected levels of complex with the reference level. The treatment regime can be altered by changing the drugs administered to treat the disease and/or changing the frequency and/or dose of the drug administered, depending on the progress of the disease. An increased level of the complex compared to a base line level will typically indicate that the individual has or is in the process of developing an α-synuclein pathology. The base line level will typically be calculated from a sample from an individual known not to have an α-synuclein pathology (a "normal individual") or from an earlier test of a sample taken from the same individual being tested.

A correlation has been shown to exist between CSF α-synuclein oligomers levels and disease severity. Detecting the presence and/or amount of the oligomers or fibrils in the sample can be used to follow the progression and or severity of a neurodegenerative disease, in particular for using the antibodies as a biomarker in Parkinson diseases and other diseases associated with α-synuclein pathologies.

In one embodiment of the invention the antibodies are used to diagnose whether an individual has Parkinson's disease. A CSF sample is taken from the patient. Antibodies are contacted with the sample in conditions effective to allow complexes to form between the antibodies and aggregated α-synuclein present in the sample. The presence of the antibody complexes can then be detected. The amount of complexes formed can be measured and compared to a reference level.

In one embodiment of the invention the antibodies can be used in an ELISA to measure aggregated α-synuclein in CFS. The antibodies can be used to measure aggregated α-synuclein in a sample with high sensitivity and specificity compared to ELISA using other antibodies. In particular an ELISA using the antibodies of the invention has a higher sensitivity and specificity to detect α-synuclein oligomers and protofibrils in CSF as compared to an ELISA using mAb 211 as a capture antibody and biotinylated 211 as a detection antibody.

The methods can be used to monitor the effectiveness of a therapeutic agent, by using the results of the analysis undertaken. An effective therapeutic agent can be determined as one that causes a decrease in the amount of α-synuclein aggregates present in a sample taken, as compared to a reference value. The reference value may reflect the amount of α-synuclein in the patient before treatment, or may represent a typical amount of α-synuclein to be found in untreated patients.

The antibodies may be labelled with a detectable label. The label will be one that allows detection of the antibody when bound to the α-synuclein aggregates. Detectable labels include, but are not limited to fluorescent labels, radioactive labels and contrast agents. Suitable radiolabels include those such as $F^{18}$, $I^{123}$, $In^{131}$, $C^{14}$, $H^3$, $Tc^{99m}$, $P^{32}$, $I^{125}$ and Gallium 68. Suitable fluorescent labels can include fluorescein and rhodamine. Suitable contrast agents include: rare earth ions such as gadolinium (Gd), dysprosium and iron, and magnetic agents. Other labels include nuclear magnetic resonance active labels, positron emitting isotopes detectable by a PET scanner, chemiluminescent and enzymatic markers.

The antibodies can be labelled by standard techniques.

In another aspect of the invention the antibodies can be used as an imaging agent. In particularly the antibodies can be used for detecting and localization and/or quantitation of α-synuclein aggregates in human and animal tissues.

The invention provides a method of imaging α-synuclein aggregates, comprising detecting the binding of the antibody to α-synuclein aggregates.

In one embodiment antibodies of the invention can be contacted with a sample and then the antibody in the sample that has bound to α-synuclein aggregates can be detected. The antibody is preferably a labelled antibody. The presence or absence of the α-synuclein aggregates may be detected in the brain in vivo using any suitable imaging techniques. In such in vivo methods, the method may further comprise administering the antibody to an individual and detecting the antibody.

Suitable imaging techniques include positron emission tomography (PET), gamma-scintigraphy, magnetic resonance imaging (MRI), functional magnetic resonance imaging (FMRI), magnetoencephalography (MEG), and single photon emission computerized tomography (SPECT).

The presence or absence of α-synuclein aggregates may also be detected in vitro, for example in tissue samples, such as a brain section. In such embodiments suitable imaging techniques may also include electron microscopy, confocal microscopy or light microscopy.

The number and/or size of α-synuclein aggregates present in the brain of an individual correlates with the progression of the α-synuclein associated disease. An increase in the size or number of α-synuclein aggregates indicates a progression of the disease, whilst a decrease in the size or number of α-synuclein aggregates indicates a regression of the disease.

The diagnostic methods can also be for veterinary use.

The invention also relates to a kit comprising an antibody according to the invention for carrying out the diagnostic methods. The antibody may be an intact immunoglobulin molecule or fragment thereof such as Fab, F(ab)2 or Fv fragment. The antibody may be labelled as described above. The kit can be for use in a method of determining whether an individual has a neurodegenerative disease.

The kit may additionally comprise one or more other reagents or instruments which enable any of the methods to be carried out. Such reagents or instruments including, but not limited to one or more of the following, suitable buffers, means to obtain a sample from an individual, a support comprising wells on which quantitative reactions can be done. The kit may optionally comprise instructions for carrying out the methods above.

In one embodiment of the invention the antibody and fragment thereof can be used as a medicament.

The invention relates to antibodies or fragments thereof for use in the treatment of a neurodegenerative disorder associated with α-synuclein in an individual.

The invention also relates to a method of treating a neurodegenerative disorder with α-synuclein pathology in an individual, comprising administering to the individual a therapeutically effective amount of the antibody or fragment thereof.

The neurodegenerative disorder can include but is not limited to Parkinson's disease, dementia, Alzheimer's disease, Down's syndrome, multiple-system atrophy, psychosis, schizophrenia or Creutzfeldt-Jakob disease. The dementia may be dementia with Lewy bodies.

α-Synuclein aggregation may be reduced or inhibited by the administration of an antibody or fragment thereof. The antibody may be administered to a sample comprising soluble synuclein species or directly to an individual.

The antibody may be administered directly to the site of α-synuclein aggregate deposit, e.g. a Lewy body, typically by injection into a blood vessel supplying the brain or into the brain itself.

An individual may be a human or non-human animal. The compositions and methods as herein described can also be used in veterinary practice.

The terms 'treatment' and "treating" and the like, is intended to include curing, relieving, reversing, alleviating, managing or delaying the onset, of the condition, or to reduce the risk of developing or worsening the condition. The terms are also intended to include palliative, prophylactic and preventative treatment of the condition.

In one embodiment of the invention a pharmaceutical composition comprises the antibody or fragment thereof and a pharmaceutically acceptable diluent or carrier.

In general, the nature of the carrier will depend on the particular mode of administration being employed. Pharmaceutical forms include solid, solutions and suspensions. Suitable pharmaceutical carriers include inert diluents or fillers, water and various organic solvents. Compositions may also include additional ingredients such as flavourings, binders & excipients.

Forms suitable for oral administration include tablets, capsules, pills, powders, sustained release formulations, solutions, and suspensions. Forms suitable for parental injection include sterile solutions, suspensions or emulsions.

Exemplary parenteral administration forms include suspensions or solutions in sterile aqueous solutions, for example aqueous propylene glycol or dextrose solutions. Such dosage forms can be suitably buffered, if desired.

Exemplary oral forms such as tablets may include: disintegrants such as starch, alginic acid and complex silicates; binding agents such as sucrose, gelatin and acacia; and lubricating agents such as magnesium stearate, sodium lauryl sulfate and talc. Solid compositions may also include soft and hard gelatin capsules. Preferred materials include lactose, milk sugar and high molecular weight polyethylene glycols.

Methods of preparing various pharmaceutical compositions are well known to those skilled in the art. Reference is made to 'Remington's Pharmaceutical Sciences'.

The invention also relates to the antibody and fragment in combination with one or more further therapeutic agents.

EXAMPLES

The following examples are provided for illustration and are not intended to limit the invention to these specific examples.

Example 1

Preparation α-synuclein Aggregates Antibodies
Preparation of α-synuclein Fibrils
Purified recombinant α-synuclein was used. Freshly prepared α-synuclein (50 μM) solution was incubated at 37° C. in a thermomixer (800 rpm) for 7 days for aggregation. The aggregation process of α-synuclein was monitored by Thioflavin-S (Th-S) binding assay. Once the aggregation was complete, the fibrils were aliquoted into small samples and stored at −80° C. until used.

Preparation of α-synuclein Oligomers
Freshly prepared α-synuclein solution was mixed with dopamine at 1:7 molar ratio (α-synuclein:dopamine) and incubated at 37° C. in a thermomixer (800 rpm) overnight. Next day the solution containing oligomers was aliquoted into small samples and stored at −80° C. until used.

Immunization
Balb/c female mice were used for sub-cutaneous immunization with α-synuclein. Each mouse received an initial immunization of 50 μg of the α-synuclein solution mixed with Freunds Complete Adjuvant (1:1 v/v) followed by booster immunization, 3 weeks interval, with 25 μg of α-synuclein mixed with Freunds Incomplete Adjuvant (1:1 v/v). On the $10^{th}$ day of each booster immunization, blood was collected from tail vein and serum was separated. ELISA was carried out to check the immune response of the hosts to α-synuclein.

ELISA to Check the Immune Response of the Hosts.
A 96 well clear maxisorp plate (NUNC) was coated with 100 μL per well (70 ng/well) for overnight incubation in PBS. The plate was then washed three times with PBST (PBS containing 0.05% Tween-20), and then incubated with blocking buffer (PBST containing 2.25% gelatin) for 1 h at room temperature. The plate was washed three times with PBST and 100 μl of serially diluted antiserum (1/100 followed by 10 dilutions) form the mice were added to the wells in duplicates and the plate was incubated at room temperature for 1 h. After the plate was washed PBST, 1:20000 diluted goat anti-mouse IgG-HRP (100 μl per well, Jackson Immunoresearch) was added to each well and incubated for 1 h at room temperature. The plate was then washed three times with PBST and incubated with 100 μl of TMB substrate (KPL, Gaitherburg, USA) until colour developed. The reaction was stopped by adding $H_2SO_4$ (0.6 N, 100 μl per well), and absorbance values at 450 nm were measured using a Victor X3 microtiter plate reader. The hosts that showed good immune response were then taken for fusion.

Titer values for the hosts immunized with α-synuclein fibrils (hosts 19 (FIG. 1A), 22 (FIG. 1B), and 23 (FIG. 1C)) and α-synuclein oligomers (hosts 210 (FIG. 1D), 211 (FIG. 1E) and 212 (FIG. 1F)) were taken and the results are shown in FIGS. 1A-1F and Table 1. The hosts were taken for fusion when the titer values came down to half of the previous response.

TABLE 1

| Immunogen | Host ID | $1^{st}$ Booster titer | $1^{st}$ Pre-fusion titer | $2^{nd}$ Pre-fusion titer | $3^{rd}$ Pre-fusion titer |
|---|---|---|---|---|---|
| α-synuclein fibrils | 19 | 8871 | 13461 | 6061 | 1923 |
|  | 22 | 4924 | 8543 | 1939 | 475 |
|  | 23 | 10514 | 11402 | 7905 | 1595 |
| α-synuclein oligomers | 210 | 430 | 2138 | 1059 | 614 |
|  | 211 | 578 | 1608 | 1205 | 604 |
|  | 212 | 155 | 1522 | 891 | 339 |

Mice immunized with α-synuclein fibrils showed a very high titer immediately after the first booster. Hence no further booster immunization was given to these hosts. Mice immunized with α-synuclein oligomers showed a satisfactory response after the second booster. Before taking the mice for fusion, pre-fusion titer (after 1 month rest) was carried out. Some hosts showed a high titer even after 2 months of rest owing to the high immunogenicity of the α-synuclein aggregates.

Fusion of Splenocytes with Sp2/O Myeloma Cells

The mice of the previous experiments were given a final intra-peritoneal immunization, 3 times the initial dose, in PBS. After 3 days, the mouse was sacrificed. The spleen was isolated aseptically and washed in IMDM (Gibco). Splenocytes were extracted, counted and fused with Sp2/0 myeloma cells using 50% PEG 4000 (Merck). The fused cells were re-suspended in IMDM growth media (IMDM containing 2 mM glutamax (Gibco), 1×Penstrep (100 U/ml penicillin and 100 μg/ml streptomycin; Sigma), 50 μg/ml Gentamycin (Sigma), 50 μM 2-mercaptoethanol (Sigma) and 20% fetal bovine serum, Hyclone) supplemented with HAT (1×, Sigma) and macrophages, 6×10$^5$ cells/plate (freshly isolated from 5-6 weeks old Balb/c mice). The cells were plated (200 μl/well) into 96-well tissue culture plates (Nunc) and grown at 37° C., 5% $CO_2$. After one week of incubation, the media from the plates were changed to freshly prepared IMDM growth media supplemented with HT (1×, Sigma). The hybridomas were allowed to grow until the media colour changes to yellow. The culture supernatant was used for screening of positive clones.

Screening for Positive Clones

A 96 well clear maxisorp plate (Nunc) was coated by overnight incubation with 100 μl per well (70 ng/well) of either α-synuclein fibrils or oligomers in PBS. The plate was then washed three times with PBST (PBS containing 0.05% Tween-20), and incubated with the blocking buffer (PBST containing 0.05% Tween 20) for 1 h at room temperature. Then the plate was washed with PBST before adding 100 μl/well of culture supernatant from the fusion plate. The plate was incubated at room temperature for 1 h. After the plate was washed with PBST (3×), 1:20000 diluted goat anti-mouse IgG-HRP (100 μl per well, Jackson Immunoresearch) was added to each well and incubated for 1 h at room temperature. The plate was then washed with PBST and incubated with 100 μl of TMB substrate (KPL, Gaitherburg, USA) until colour developed. The reaction was stopped by adding 100 μl $H_2SO_4$ (0.6 N), and the absorbance at 450 nm was measured using a Victor$^3$ 1420 multilabel microtiter plate reader. The positive clones were transferred to a 24 well plate and were screened again to identify the stable clones.

A total of 1100 positive clones were obtained from the initial screening and 57 positive clones (from mouse immunized with α-synuclein fibrils), and 43 clones (from mice immunized with α-synuclein oligomers) were selected for further characterization. The isotype of the positive clones were identified using isotyping kit (Sigma). IgG clones were selected, passaged multiple times to identify stable clones and taken for single cell cloning.

Isotyping

A 96 well clear maxisorp plate (Nunc) was coated by overnight incubation at 4° C. with 100 I/well of 1/1000 diluted anti-mouse heavy chain antibodies (Sigma, Isotyping Kit) in PBS, pH 7.4. The plate was then washed 3 times with PBST (PBS containing 0.05% Tween 20), and incubated with blocking buffer (PBS containing 2.5% gelatin and 0.05% Tween 20; 400 μl per well) for 1 h at room temperature. The plate was then washed 3 times with PBST, and 100 μl of culture supernatant from each clone was added to the wells. The plate was incubated at room temperature for 1 h, and after the plate was washed with PBST, 1:20000 diluted goat anti-mouse IgG-HRP (100 I/well) was added to each well and incubated for 1 h at room temperature. The plate was then washed with PBST and incubated with 100 μl/well of TMB substrate (KPL, Gaitherburg, USA) until the colour developed. The reaction was stopped by adding 100 μl/well of $H_2SO_4$ (0.6 N), and the absorbance at 450 nm were measured by Victor$^3$ 1420 multilabel microtiter plate reader. The IgG positive clones were transferred to a T-25 flask and taken for single cell cloning.

Isotypes of clones obtained from mice immunized with α-synuclein fibrils or oligomers is shown in Table 2.

TABLE 2

| Clones obtained from mice immunized with α-synuclein fibrils | | Clones obtained from mice immunized with -synuclein oligomers | |
|---|---|---|---|
| Clone Name | Isotype | Clone Name | Isotype |
| Syn-F1 | IgG1 | Syn-O1 | IgG2b |
| Syn-F2 | IgG2a | Syn-O2 | IgG1 |
| Syn-F3 | IgG2a | Syn-O3 | IgG1 |
| Syn-F4 | IgG1 | Syn-O4 | IgG1 |
| Syn-F5 | IgG1 | Syn-O5 | IgG1 |
| Syn-F6 | IgG2b | Syn-O6 | IgG1 |
| | | Syn-O7 | IgG1 |
| | | Syn-O8 | IgG1 |

From 100 clones identified and selected, 33 parental clones were found to be IgG isotype. Remaining clones were either IgM or a mixture of IgG and IgM isotypes. The IgM or mixed isotype clones were frozen and not taken for further characterization. The IgG clones were passaged at least 3 times and 14 stable clones were selected. 10 clones were found to be IgG1, 2 clones were IgG2a and 2 were found to be of IgG2b isotype.

Single Cell Cloning

Cells were collected from T-25 flask of positive hybridoma clones. The cells were counted, diluted in IMDM and -100 cells were taken and added to 20 ml of growth media. Growth medium was IMDM (Gibco) supplemented with glutamax (2 mM, Gibco), Penstrep (Sigma), 50 μg/ml Gentamycin (Sigma), 50 μM beta-ME (Sigma), 20% fetal bovine serum (Hyclone) and macrophages (6000 cells/well) freshly isolated from young BALB/c. The cells were mixed and plated (200 μl/well) in a 96 well tissue culture plate. The plate was incubated at 37° C., 5% $CO_2$. The hybridomas were allowed to grow, wells containing single cells were marked, until they grew confluent. The culture supernatant from the wells showing single colony was taken for screening by ELISA and the cells from positive wells were transferred to 24 well plates, screened again before transferring to T-25 flask. The culture supernatant from T-25 flask was screened at least thrice to select stable clones.

Single cell clones obtained from each clones were transferred to 24 well plate, and further checked for stability. At least two single cell clones from each parental clone were transferred to T-25 flask for further characterization.

Example 2

Screening the specificity of hybridoma to α-synuclein aggregates by Dot Blot 50 ng (5 μl in PBS) of α-synuclein fibrils (F), oligomers (0) or monomers (M) were spotted onto a nitrocellulose membrane and dried at room temperature for 30 minutes. The membranes were blocked with 5% skimmed milk in PBST (PBS containing 0.05% Tween 20) for 1 h at room temperature. The membranes were then washed 3 times with PBST before probing with culture supernatant 1:1 diluted in PBST and incubated for 2 h at room temperature. The Syn-1 antibody was used as control. After the membranes were washed with PBST, 1:20000 diluted goat anti-mouse IgG-HRP was added and incubated for 1 h at room temperature. The membranes were then washed with PBST followed by 2 times with PBS. The membranes were developed with Super signal West pico Chemiluminescent substrate (Pierce).

Figure 2:
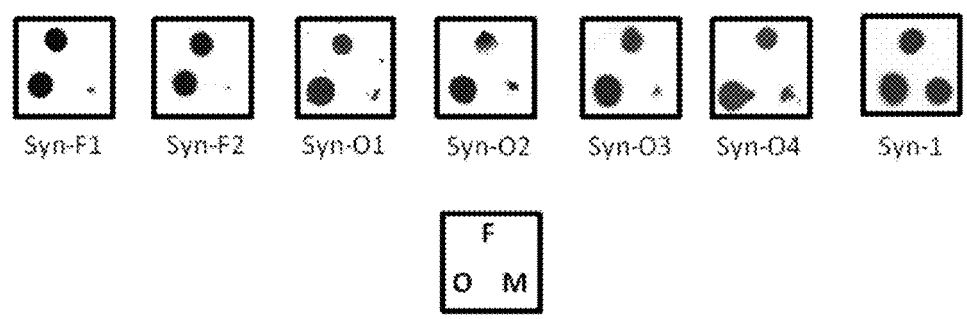
FIG. 2 shows the results of the dot plots for screening the specificity of the hybridomas to α-synuclein aggregates, (fibrils (F), oligomers (0) and monomers (M)) as described in Example 2.
Figure 3A:
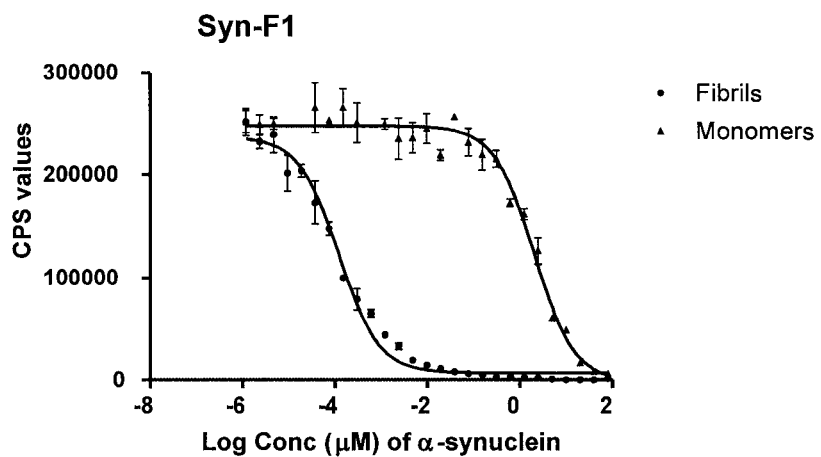
FIGS. 3A-3G show the results of the inhibition ELISA using the antibodies Syn-F1 (FIG. 3A), Syn-F2 (FIG. 3B), Syn-O1 (FIG. 3C), Syn-O2 (FIG. 3D), Syn-O3 (FIG. 3E) and Syn-O4 (FIG. 3F), and Syn-1 antibody (BD Bioscience) (FIG. 3G) as a control as described in Example 4.
Figure 3B:
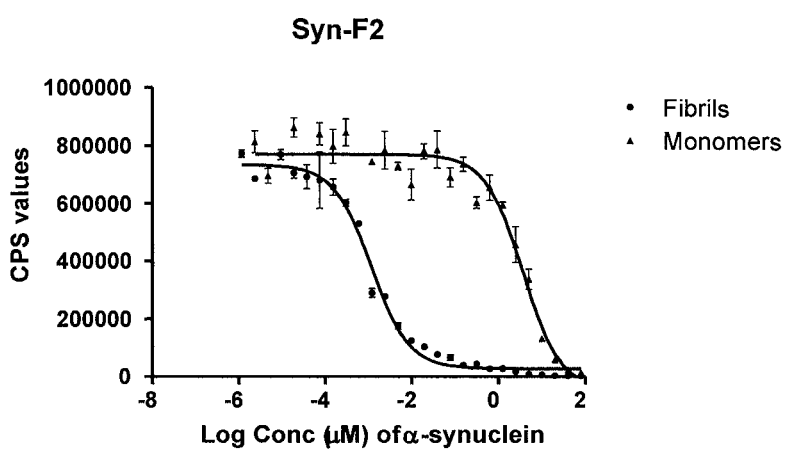
Figure 3C:
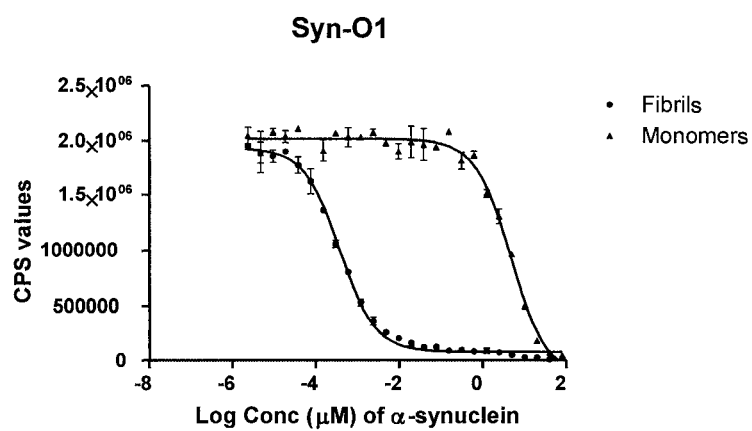
Figure 3D:
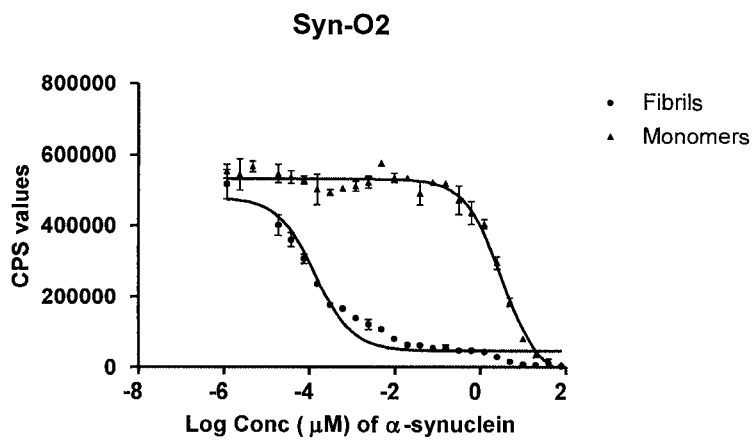
Figure 3E:
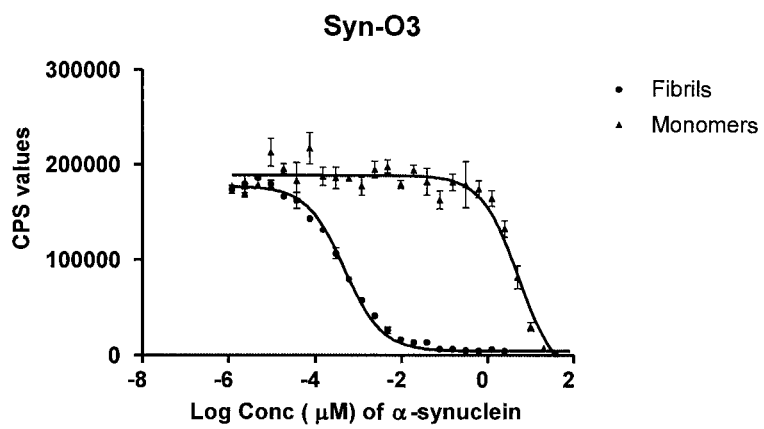
Figure 3F:
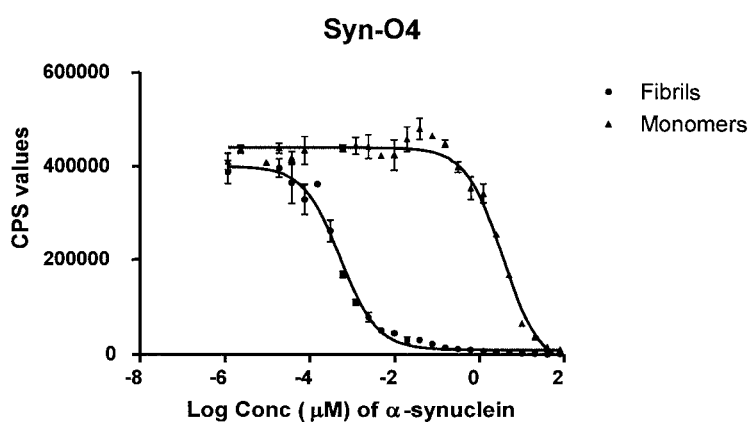
Figure 3G:
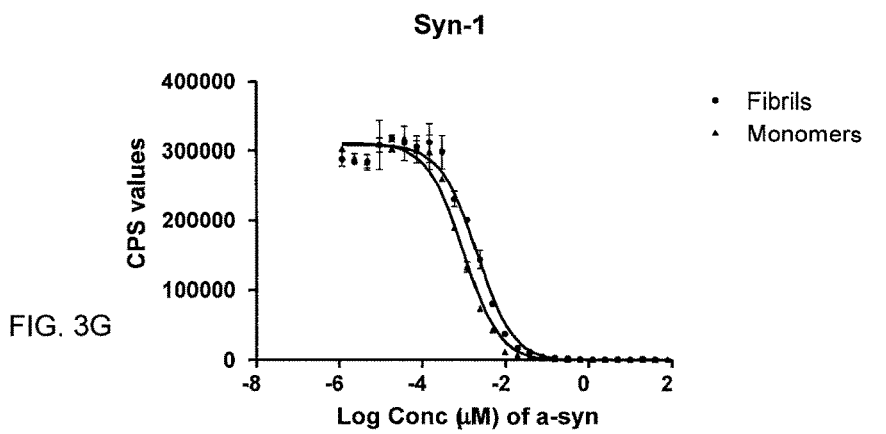

The rest of the dot blots are shown in FIG. 2. Out of 278 clones tested by dot blot, 45 clones were found to be stable and out of that 14 clones were specific for α-synuclein aggregates.

Example 3

Mass Culture and Purification of Monoclonal Antibody

Six clones identified to be specific for α-synuclein aggregates were taken for mass culture. These clones were Syn-F1, Syn-F2, Syn-O1, Syn-O2, Syn-O3 and Syn-O4. The growth media was CDM4mAb (Hyclone) supplemented with 2 mM glutamax (Gibco), Penstrep (Sigma), 50 µg/ml Gentamycin (Sigma) and 50 µM beta-ME (Sigma). Once the cells were confluent and the media colour changed to yellow, the culture supernatnants were collected and stored at −20° C. until used. Monoclonal antibodies were purified from the culture supernatants using Protein G-Agarose affinity chromatography. Protein G-Agarose column was prepared and equilibrated with 20 bed volumes of 20 mM Phosphate buffer pH 7.2. The culture supernatant (200 ml) was centrifuged at 1500 rpm for 10 min at 4° C. The supernatants were collected and passed through the column, 5-6 times, keeping the flow rate to ~1 ml/minute. The column was then washed with 15 bed volumes of 20 mM Phosphate buffer pH 7.2 to remove the proteins. The bound antibody was eluted as 500 µl fractions using elution buffer (50 mM Glycine pH 2.5) into 1.5 ml centrifuge tubes containing 50 µl of neutralization buffer (1M Tris pH 8.0). The purified antibody was finally dialyzed against PBS. Monoclonal antibody purified from different batch was pooled together and the concentration was determined by BCA assay. These monoclonal antibodies were lyophilized and stored as 100 µg aliquots at −20° C. until used.

Example 4

Characterization of Purified Antibody
Inhibition ELISA

A 384 well black maxisorp plate (NUNC) was coated with 50 µl per well (1.4 µg/ml) of α-synuclein fibrils in PBS pH 7.4 by overnight incubation at 4° C. The plate was washed 4× with PBST (PBS with 0.05% Tween) and blocked with blocking buffer (2.25% gelatin in PBS with 0.05% Tween) for 1 h at room temperature. In 0.6 ml siliconized tubes serial double dilutions of the α-synuclein fibrils, oligomers or monomers were made in blocking buffer (starting from 80 µM followed by 18 serial double dilution). To each tube equal volume of 20 ng/ml of the purified monoclonal antibodies (Syn-F1, Syn-F2, Syn-O1, Syn-O2, Syn-O3, Syn-O4) or Syn-1 (BD Bioscience), used as a control, were added, to give a final concentration of 10 ng/ml, and incubated the tubes by mixing for 2.5 h at room temperature. The preincubated solution was then added to the ELISA plates and incubated for 10 minutes at room temperature. After washing the plates with PBST (4×), 1/15000 diluted goat anti-mouse IgG-HRP conjugate (Dako) was added and the plates were incubated for 1 h at room temperature. The plates were washed with PBST and 50 µl of substrate (SuperSignal ELISA Femto Maximum Sensitivity Substrate, Thermo Scientific) was added and immediately read the plate using Victor X3 microtiter plate reader. Taking the log dilution of the α-synuclein concentration on x-axis and the CPS values on the y-axis, graphs were plotted.

Results for the comparison of binding affinity of mAbs by inhibition ELISA can be found in FIGS. 3A-3G and Table 3.

TABLE 3

| mAbs | IC 50 (µM) Fibrils | IC 50 (µM) Monomers | Fold Affinity to Fibrils |
|---|---|---|---|
| Syn-F1 | 0.00012 | 2.083 | 16558 |
| Syn-F2 | 0.00118 | 3.707 | 3141 |
| Syn-O1 | 0.00037 | 4.793 | 12737 |
| Syn-O2 | 0.00012 | 3.283 | 27312 |
| Syn-O3 | 0.00047 | 5.329 | 11129 |
| Syn-O4 | 0.00052 | 3.605 | 6932 |
| Syn-1 | 0.00210 | 0.001 | 0.476 |

All the monoclonal antibodies, Syn-F1, Syn-F2, Syn-O1, Syn-O2, Syn-O3 and Syn-O4, were found to be specific for α-synuclein fibrils.

Examples 5

Testing the Cross Reactivity of the Antibodies—Dot Blot

A) To test the cross-reactivity with amyloid fibrils formed by different proteins 50 ng (in 5 µl PBS, pH 7.4) of various amyloid proteins and peptides, fibrils (F) and monomers (M) from α-synuclein, Tau, A-beta, IAPP and ABri were spotted onto a nitrocellulose membrane and dried at room temperature for 30 min. The membranes were blocked with 5% skimmed milk in PBST (PBS containing 0.05% Tween) and incubated for 1 h at room temperature. After washing the membranes 3× with PBST, the membranes were incubated (50 ng/ml in PBST) with monoclonal antibodies, Syn-F1, Syn-F2, Syn-O1, Syn-O2, Syn-O3, Syn-O4, or control antibodies, Syn-1 (BD Bioscience) for a-synuclein, 5E2 (Gift from Dr. D. Walsh, Harvard Medical School) for Tau, 82E1 (IBL) for A-beta, R10/99 (Santa Cruz Biotechnology) for IAPP and Rabbit anti-ABri antiserum for Abri, for 2h at room temperature. The membranes were washed and incubated with either 1/20000 diluted goat anti-mouse IgG-HRP (Jackson ImmunoResearch) or 1/10000 diluted goat anti-rabbit IgG-HRP (Jackson Immunoresearch) for 1h at room temperature. The blots were then developed with Super signal West Pico chemiluminescent substrate.

Figure 4:
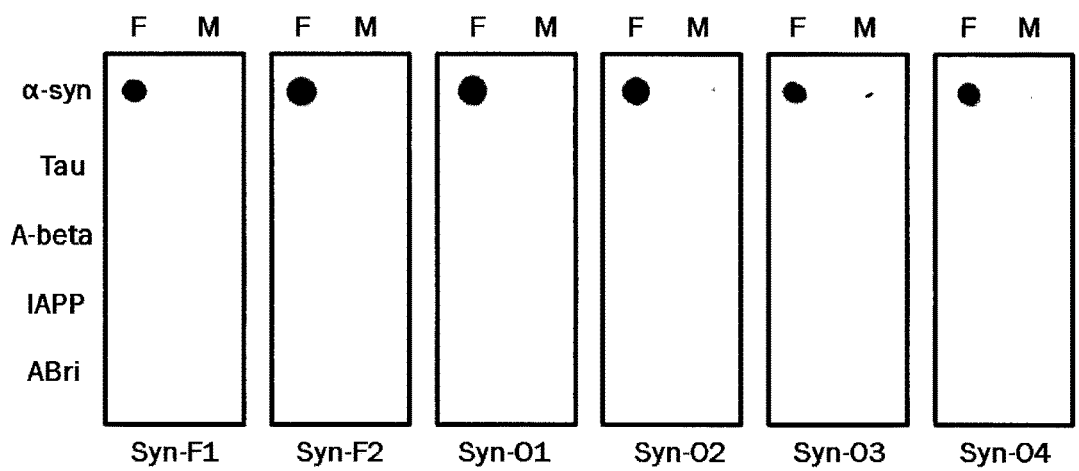
FIG. 4 shows the results of the cross reactivity of the antibodies Syn-F1, Syn-F2, Syn-O1, Syn-O2, Syn-O3 and Syn-O4 and Syn-1 with amyloid fibrils formed by different proteins as described in Example 5 (A).
Figure 4:
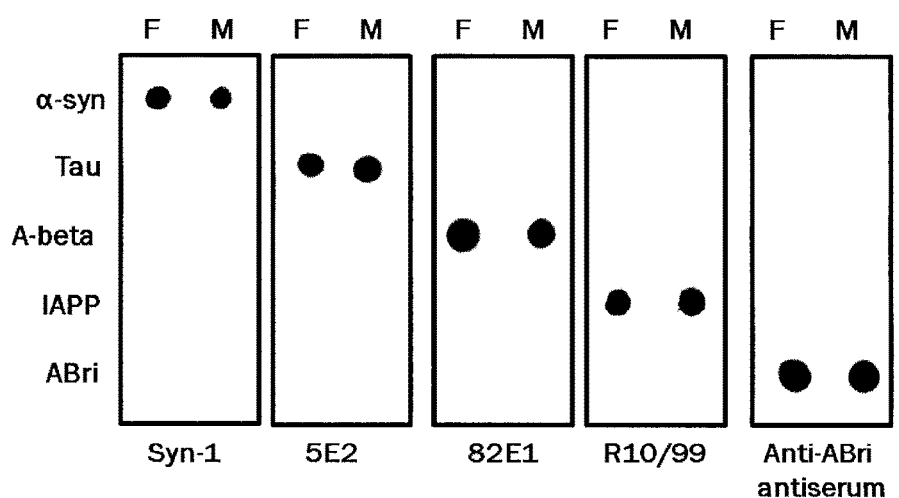

The results of the cross-reactivity with amyloid fibrils formed by different proteins can be seen in FIG. 4. The monoclonal antibodies according to the invention were found to be specific for α-synuclein amyloid fibrils and did not cross-react with other amyloid fibrils or monomers.

B) To test the cross reactivity of the conformational monoclonal antibodies, of the invention to amyloid fibrils formed by β- and γ-synuclein. 50 ng of the fibrils (F) and monomers (M) from α-, β- and γ-synuclein were spotted onto a nitrocellulose membrane. The membranes were blocked with 5% skimmed milk in PBST for 1 h and and then probed with our monoclonal antibodies (Syn-F1, Syn-F2, Syn-O1, Syn-O2, Syn-O3, Syn-O4) or control antibodies, Syn-1 (BD Bioscience) for α-synuclein, Anti-Beta-synuclein (Santa Cruz Biotechnology) for beta-synuclein and C-20 (Santa Cruz Biotechnology) for gamma-synuclein for 2h at room temperature. The membranes were washed and incubated with either 1/20000 diluted goat anti-mouse IgG-HRP conjugate (Jackson Immunoresearch) or 1/300000 diluted chicken anti-goat IgG-HRP conjugate (Santa Cruz Biotechnology) for 1 hour at room temperature. The blots were developed with Super signal West Pico chemiluminescent substrate.

Figure 5:
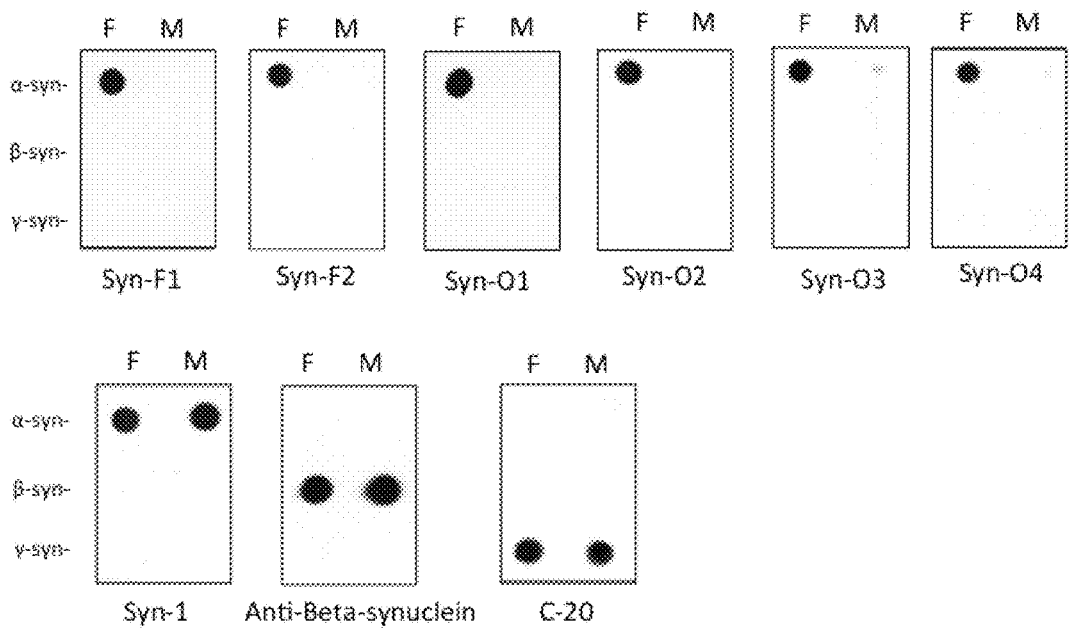
FIG. 5 shows the cross reactivity of the antibodies Syn-F1, Syn-F2, Syn-O1, Syn-O2, Syn-O3 and Syn-O4 and Syn-1 with amyloid fibrils formed by 13- and γ-synuclein as described in Example 5 (B).

The results of the cross-reactivity with amyloid fibrils formed by β-synuclein or γ-synuclein can be seen in FIG. 5. The monoclonal antibodies according to the invention were found to be specific to α-synuclein fibrils and did not react to either β- or γ-synuclein in the fibril or monomeric form.

C) To test the cross reactivity of our conformational monoclonal antibodies to different fragments of α-synuclein. 50 ng of the fibrils (F) and monomers (M) from the full-length α-synuclein (1-140) and of the peptide fragments, α-synuclein (1-122), NAC (61-95) and NAC (61-78) were spotted onto a nitrocellulose membrane. The membranes were blocked with 5% skimmed milk in PBST for 1 h and probed with our monoclonal antibodies (Syn-F1, Syn-F2, Syn-O1, Syn-O2, Syn-O3, Syn-O4) and control antibodies, Syn-1 (BD Bioscience) for α-synuclein, and 5C2 (Santa Cruz Biotechnology) for 2h at room temperature. The membranes were washed before incubating with either 1/20000 diluted goat anti-mouse IgG-HRP conjugate (Jackson Immunoresearch) or 1/300000 diluted chicken anti-goat IgG-HRP conjugate (Santa Cruz Biotechnology) for 1 h at room temperature. The blots were then developed with Super signal West Pico chemiluminescent substrate.

Figure 6:
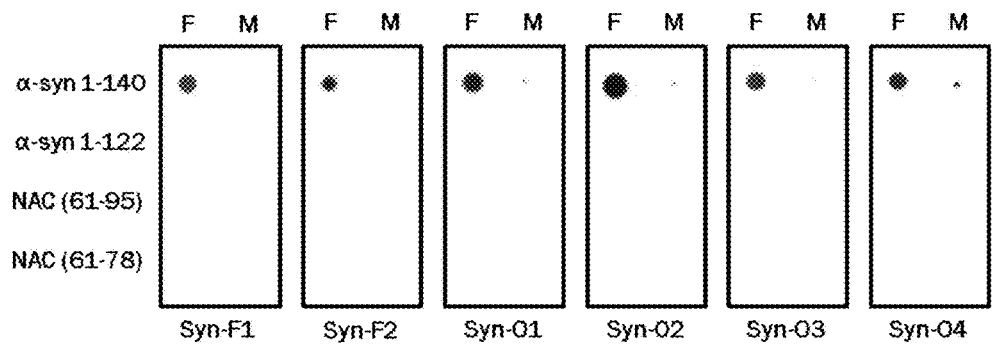
FIG. 6 shows cross reactivity of the antibodies Syn-F1, Syn-F2, Syn-O1, Syn-O2, Syn-O3 and Syn-O4 and Syn-1 with amyloid fibrils formed by α-synuclein peptides NAC (61-98), NAC (61-75) and truncated α-synuclein (1-122) as described in Example 5 (C).
Figure 6:
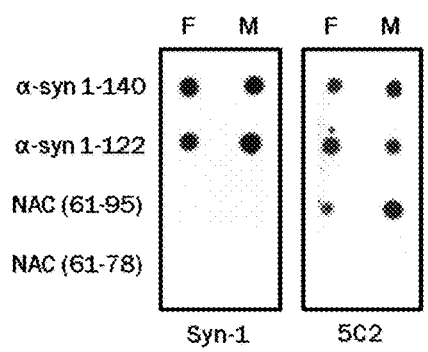
Figure 7A:
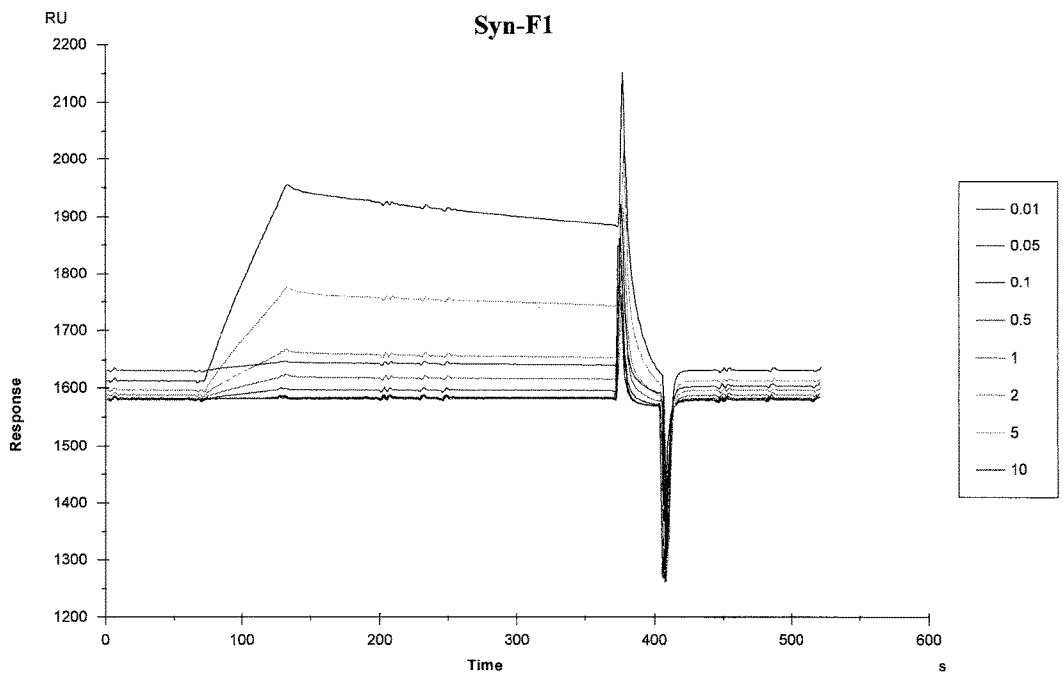
FIGS. 7A-7G show the sensogram results for the mAbs Syn-F1 (FIG. 7A), Syn-F2 (FIG. 7B), Syn-O1 (FIG. 7C), Syn-O2 (FIG. 7D), Syn-O3 (FIG. 7E) and Syn-O4 (FIG. 7F) and mAb211 (Santa Cruz Biotechnology) (FIG. 7G) using Biacore as described in Example 6.
Figure 7B:
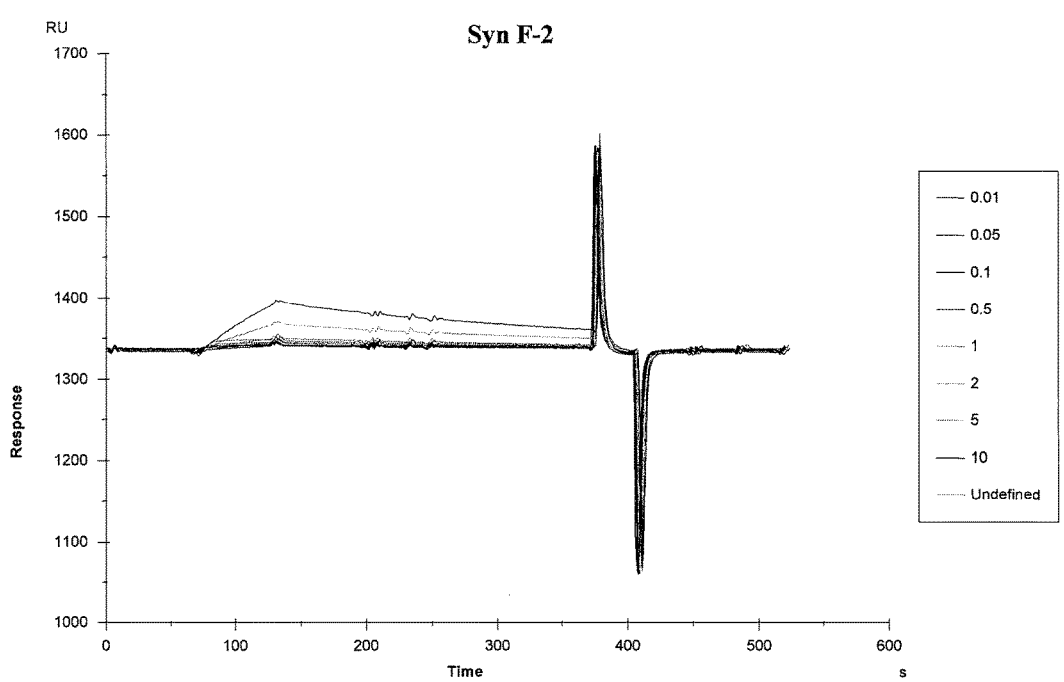
Figure 7C:
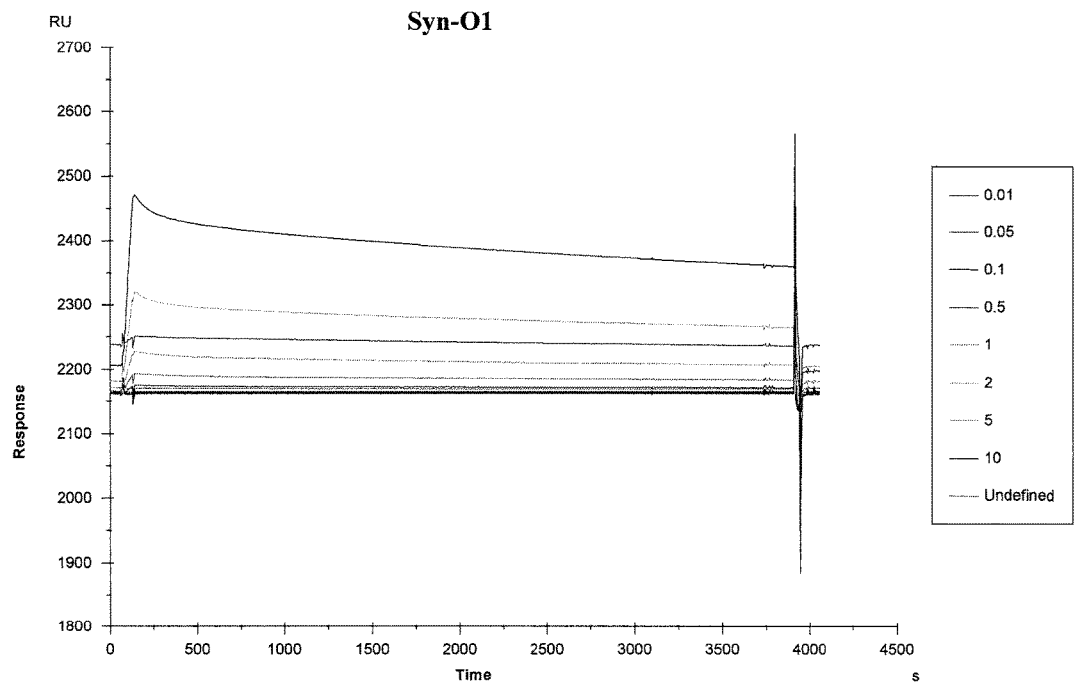
Figure 7D:
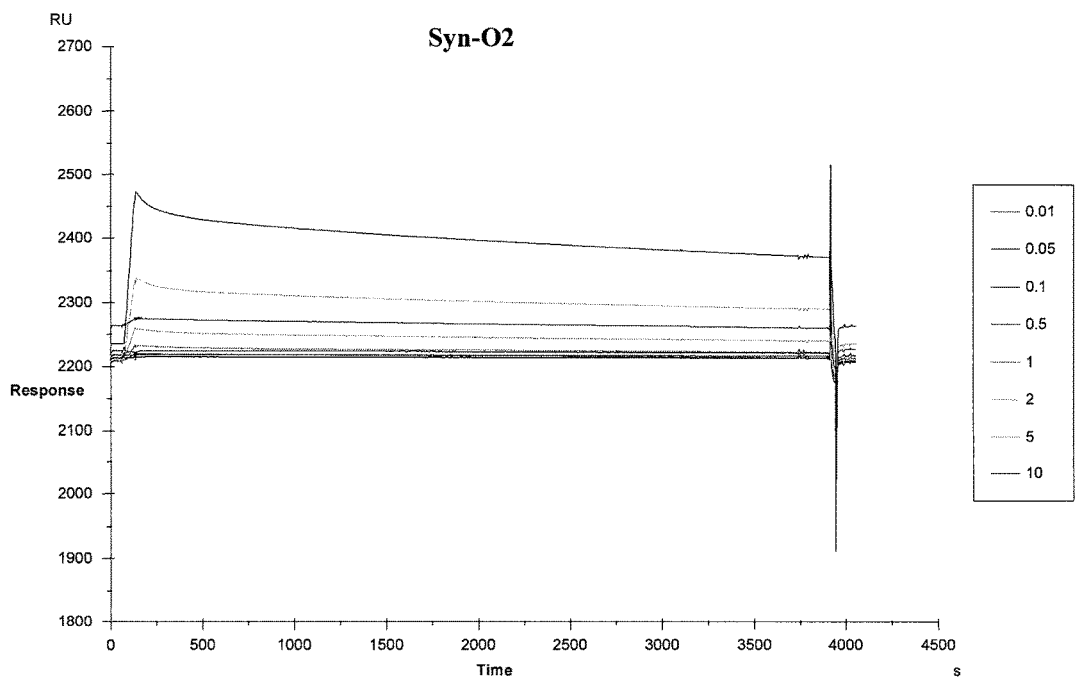
Figure 7E:
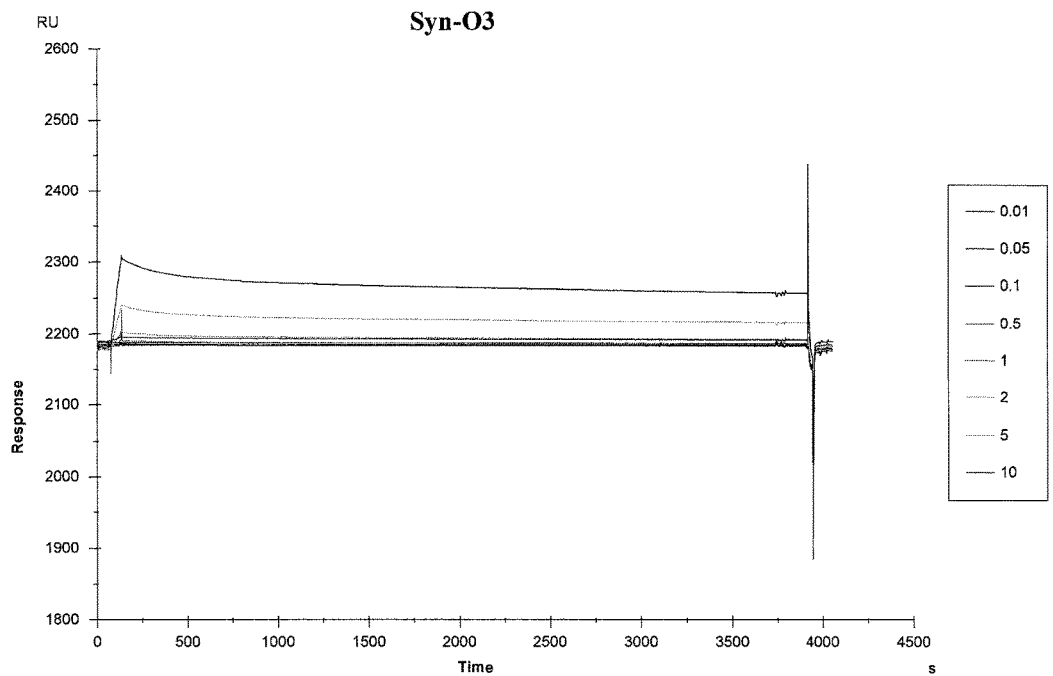
Figure 7F:
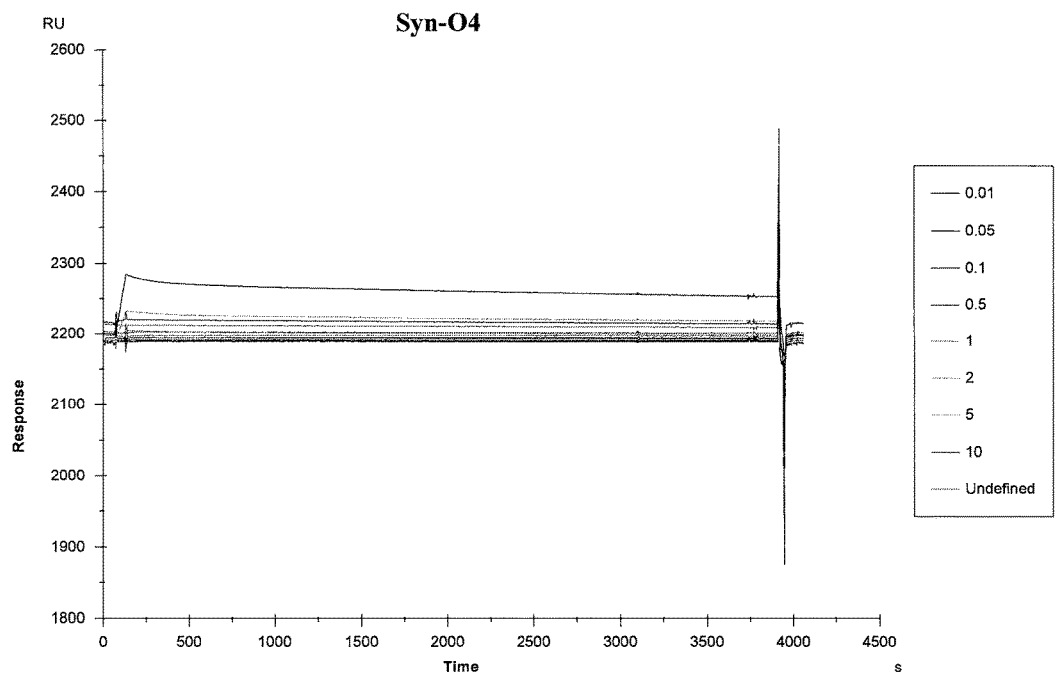
Figure 7G:
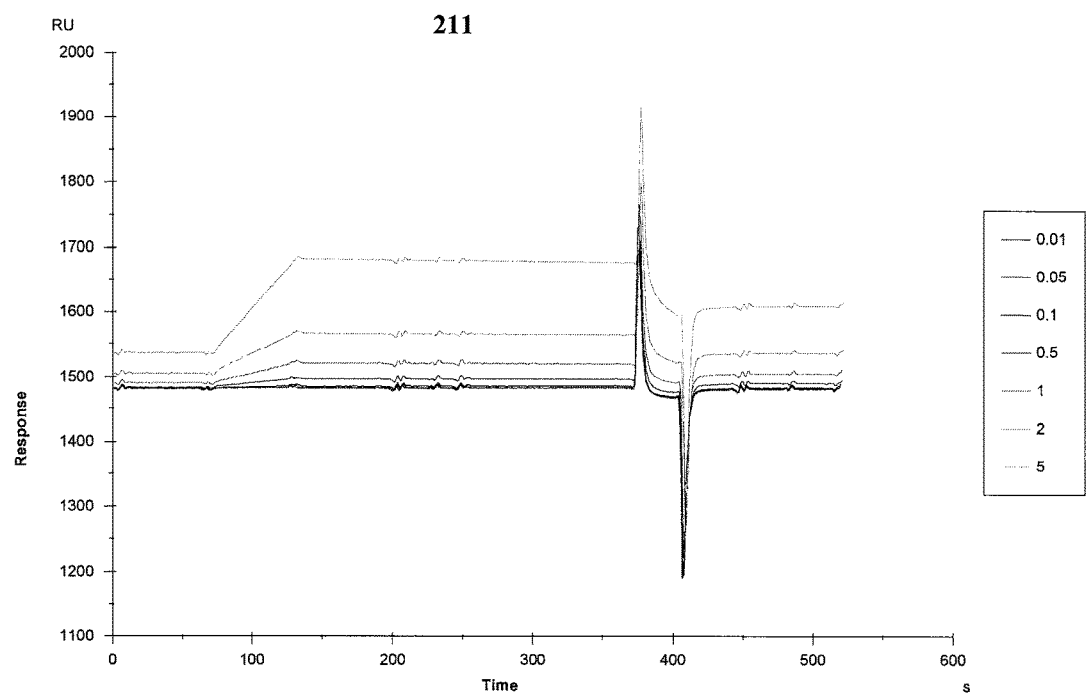
Figure 9A:
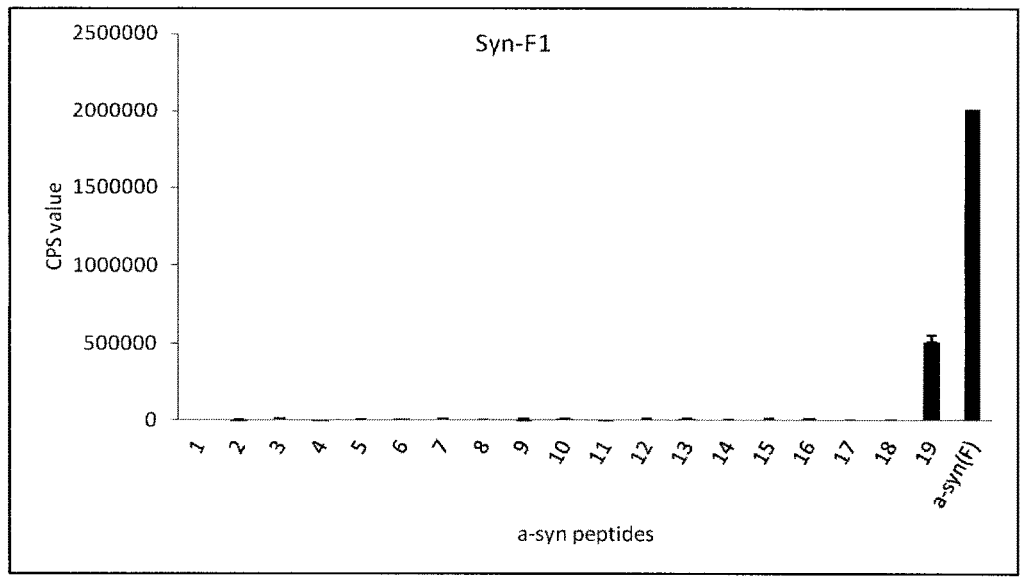
FIGS. 9A-9L show the results of the Pepscan screening by ELISA as described in Example 7. The plates were probed with the monoclonal antibodies of the invention Syn-F1 (FIG. 9A), Syn-F2 (FIG. 9B), Syn-O1 (FIG. 9C), Syn-O2 (FIG. 9D), Syn-O3 (FIG. 9E) and Syn-O4 (FIG. 9F), or with the control antibodies Syn 211 (FIG. 9G), N-19 (FIG. 9H), FL-140 (FIG. 9I), Syn-1 (FIG. 9J), 3B6 (FIG. 9K) and 5C2 (FIG. 9L).
Figure 9B:
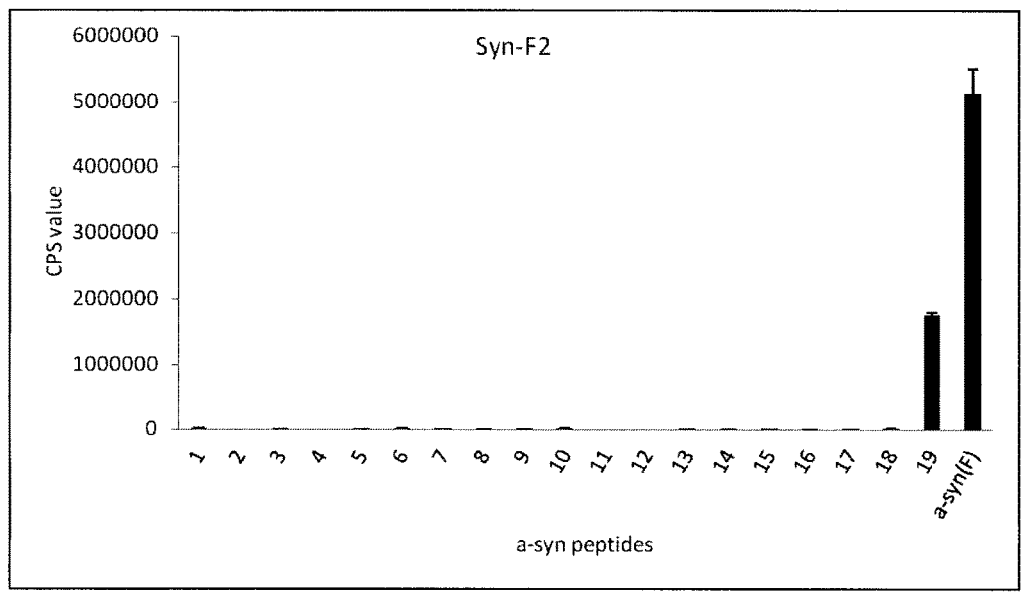
Figure 9C:
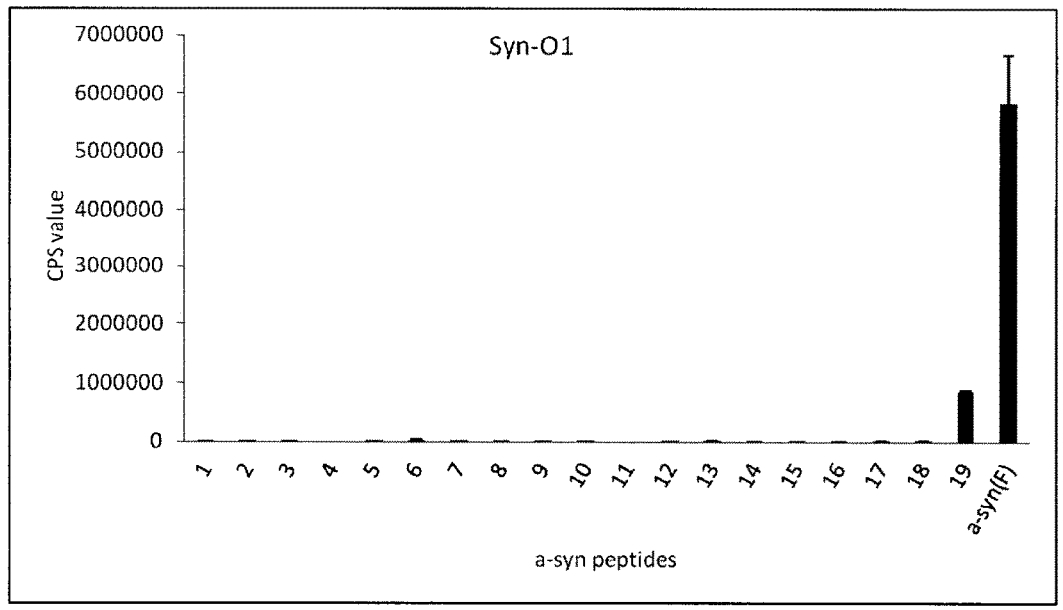
Figure 9D:
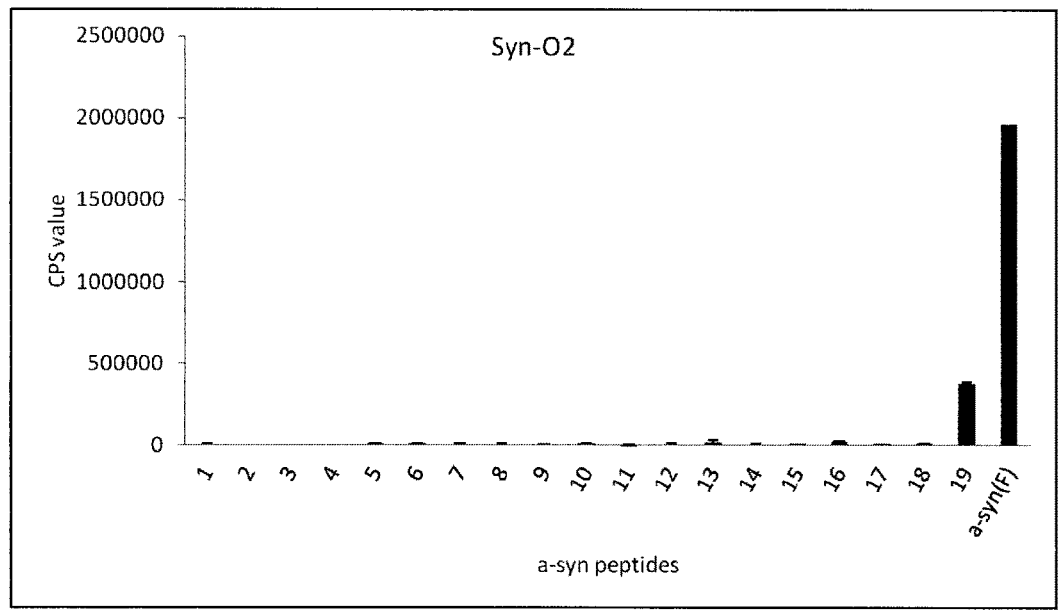
Figure 9E:
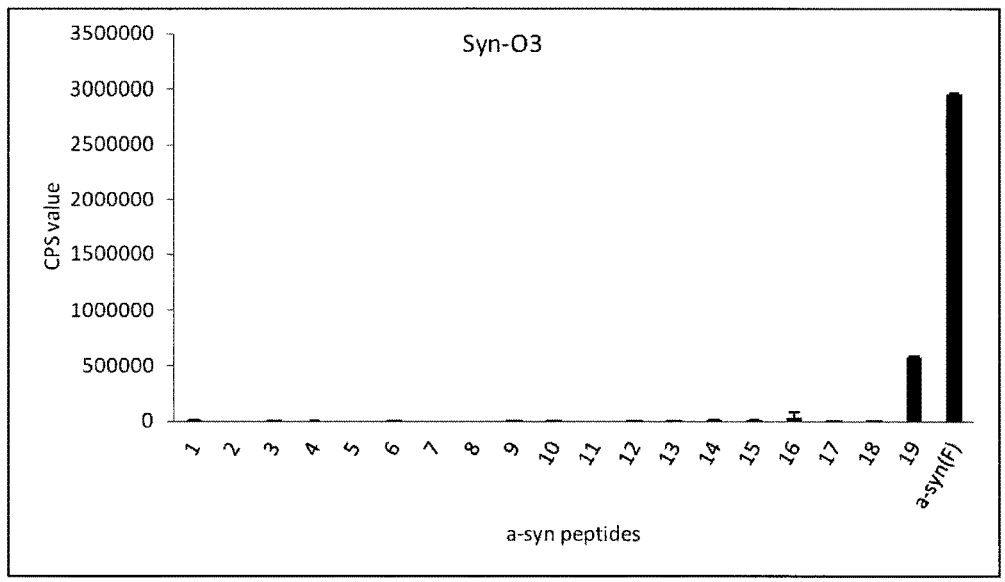
Figure 9F:
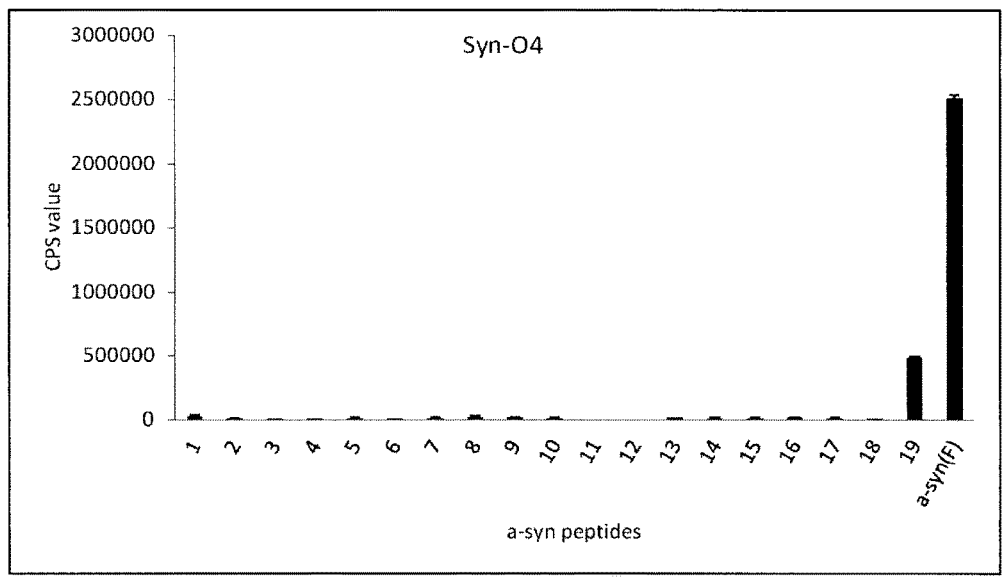
Figure 9G:
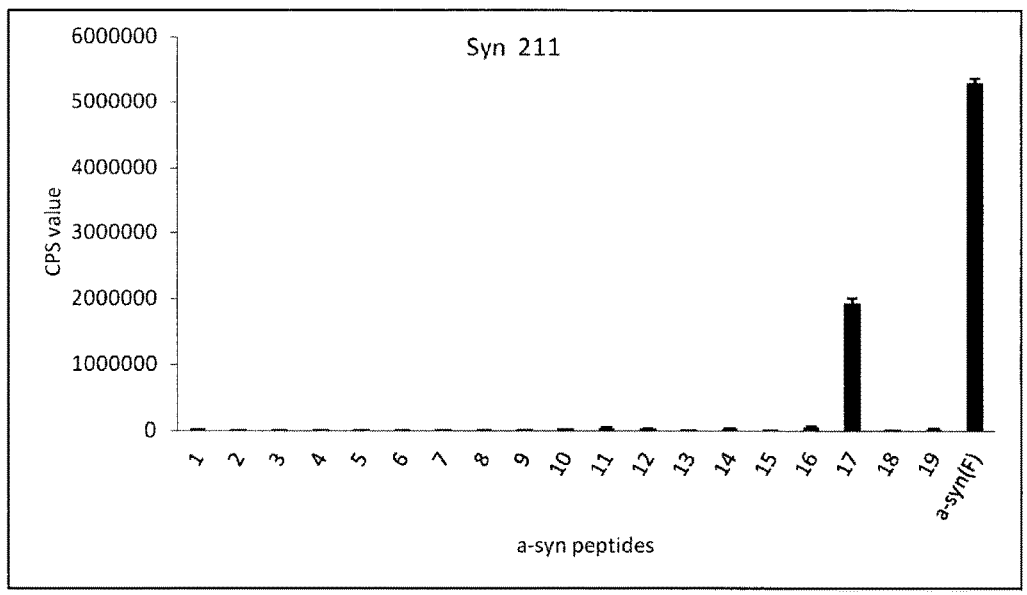
Figure 9H:
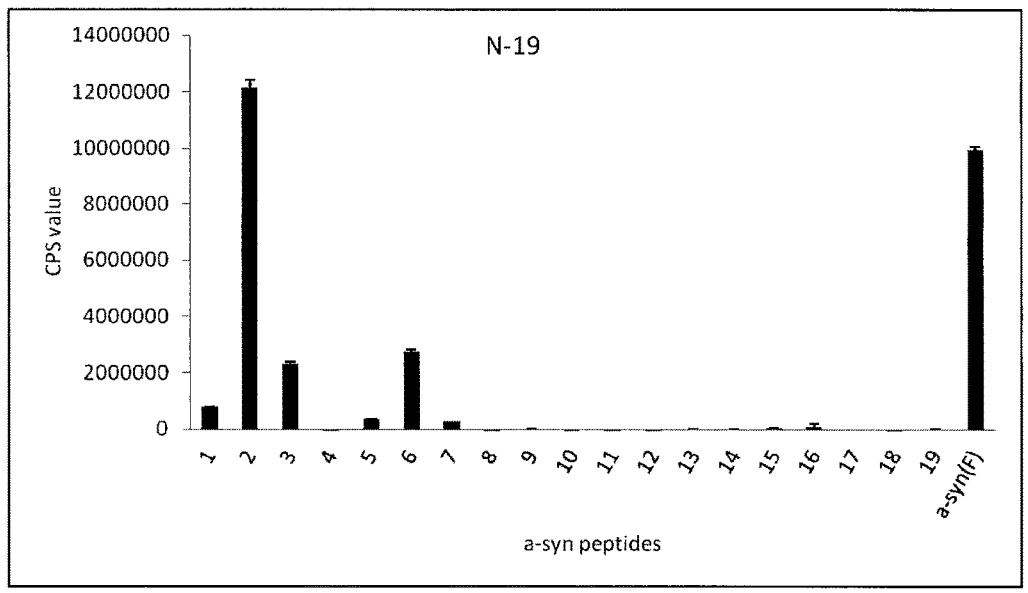
Figure 9I:
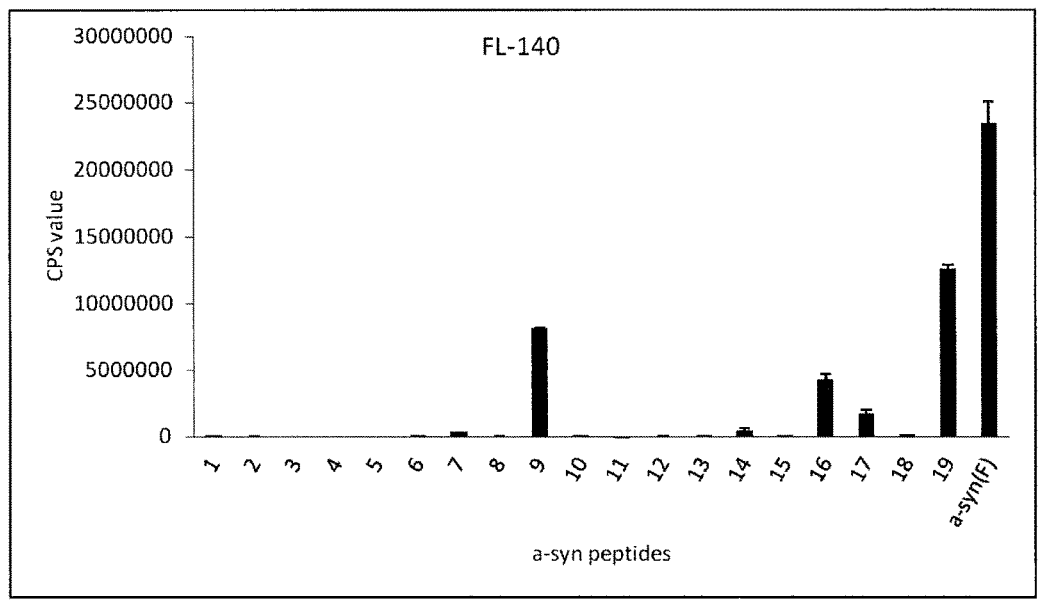
Figure 9J:
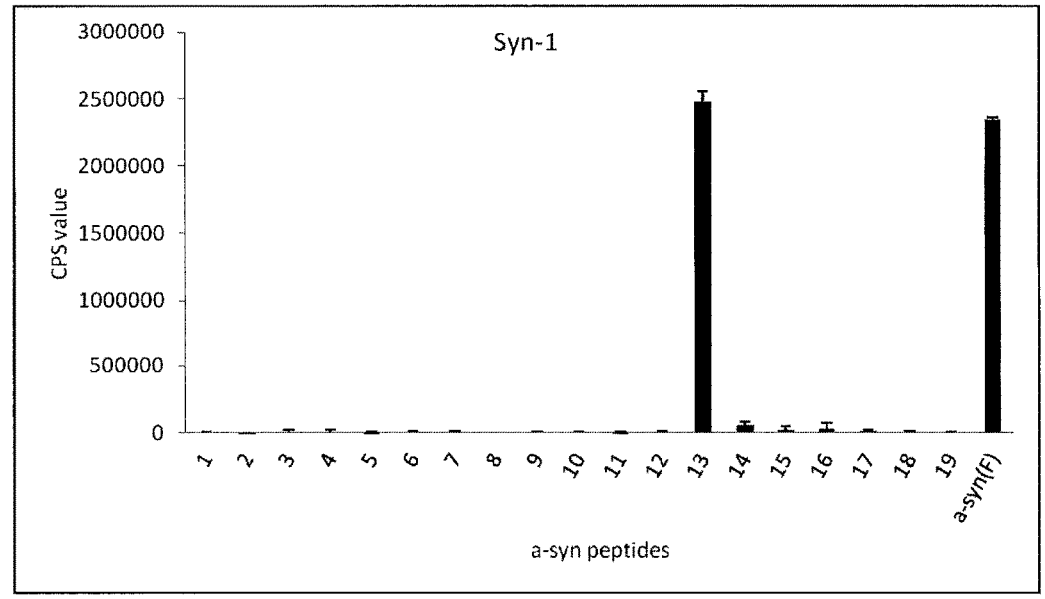
Figure 9K:
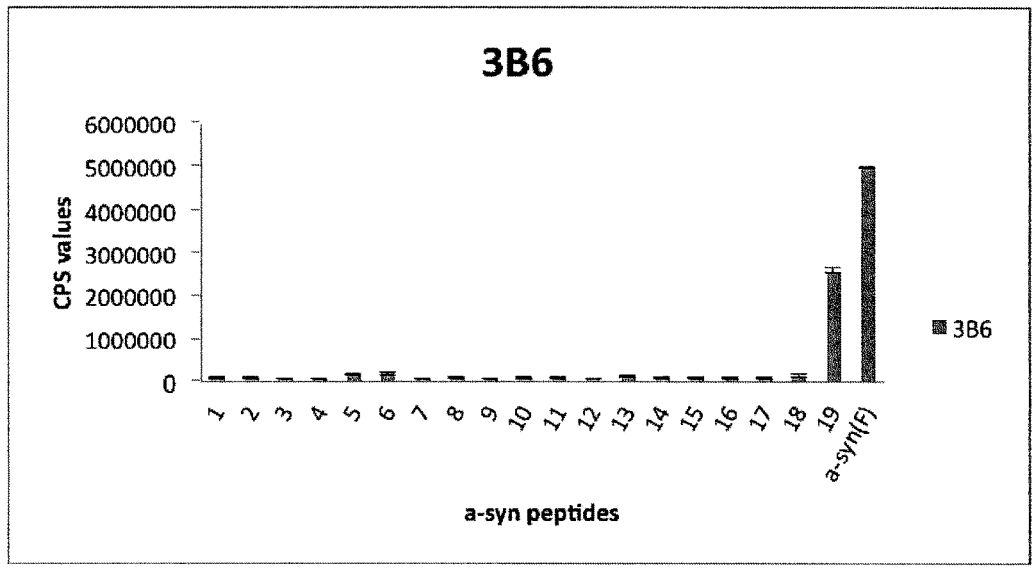
Figure 9L:
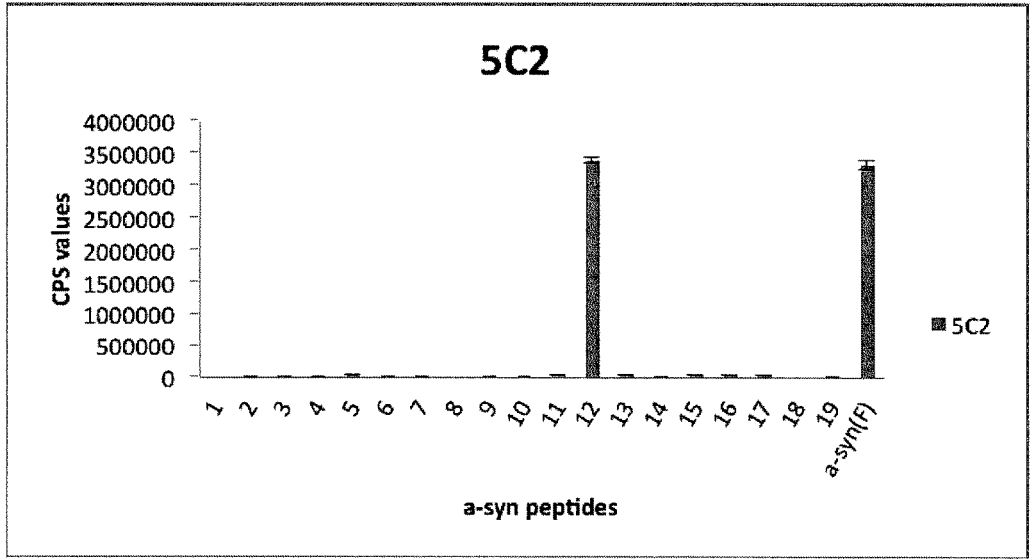

The results of the cross-reactivity with amyloid fibrils formed by different fragments of α-synuclein can be seen in FIG. 6. The monoclonal antibodies according to the invention did not react with amyloid fibrils formed by any of the truncated α-synuclein (1-122), NAC region (61-95) or NAC (61-78) but reacted only to the fibrils formed by the full length α-synuclein (1-140) suggesting that a part of epitope may be in the C-terminal region of α-synuclein. The non-reactivity of our mAbs to α-synuclein monomers also suggests that the epitope recognized by our mAb's may be conformation specific.

Example 6

Determination of Kinetic Constants.
Biacore Analysis
The kinetic constants for the interaction between our mAb's and -synuclein fibrils were determined by surface plasmin resonance measurements using the BIAcore X 100 instrument. Alpha-synuclein fibrils were immobilized to a CM5 sensor chop activated with N-hydroxy succinimide (NHS) and N ethyl-N (dimethylaminopropyl) carbofiimide (EDC) by injecting 35 µl of 120 µg/ml-synuclein fibrils in 10 mM Sodium acetate buffer, pH 4.5. The association rate constant was obtained by injecting eight different concentrations of the mAbs (Syn-F1, Syn-F2, Syn-O1, Syn-O2, Syn-O3, Syn-O4 and mAb 211 (Santa Cruz Biotechnology)) ranging from 0.01 to 10 nM in HBS running buffer (10 mM hepes, 0.15 m NaCl, 3.4 mM EDTA and 0.005% surfactant P20; pH 7.4) at a flow rate of 10 µl/min. The dissociation rate was measured at flow rate of 40 µl/min. The sensor chip was regenerated using 100 mM NaHCO3 pH. 9.6. Sensograms were analysed with the BOA evaluation software.

The results showing the comparison of mAbs by Biacore can be seen in FIGS. 7A-7G and Table 4. Monoclonal antibodies have a Kd of less than 10-8 were found. mAb Syn-O1 was found to be having the highest affinity of KD15.9 pM. The lowest affinity among the 6 mAbs were found to be for Syn-F2 with 2.6 nM.

TABLE 4

| mAb | ka (1/Ms) | kd (1/s) | KD (M) |
|---|---|---|---|
| Syn-F1 | 1.230E+7 | 0.001564 | 1.272E-10 |
| Syn-F2 | 1.256E+6 | 0.003377 | 2.688E-9 |
| Syn-O1 | 5.857E+6 | 9.360E-5 | 1.598E-11 |
| Syn-O2 | 1.314E+7 | 0.001274 | 9.694E-11 |
| Syn-O3 | 2.217E+6 | 3.789E-4 | 1.709E-10 |
| Syn-O4 | 7.236E+6 | 9.964E-4 | 1.377E-10 |
| mAb 211 | 1.648E+5 | 4.220E-4 | 2.560E-9 |

Example 7

Epitope Mapping for the mAbs
In order to find out if the mAbs of the invention detect linear or conformational epitopes, affinity of the antibodies was tested against a peptide library covering α-synuclein sequence. Peptides of 14 amino acid long, with 7 amino acid overlap, covering the human α-synuclein sequence (see Table 5) were synthesized (Shanghai Hanhong Chemical Co., China). The peptides were dissolved in either autoclaved water or DMSO to give a final concentration of 1 mg/ml.

TABLE 5

| Peptide No. | Sequence no. | Peptide Sequence |
|---|---|---|
| 1 | 1-14 | H-MDVFMKGLSKAKEG-OH |
| 2 | 8-21 | H-LSKAKEGVVAAAEK-OH |
| 3 | 15-28 | H-VVAAAEKTKQGVAE-OH |
| 4 | 22-35 | H-TKEQGVAEAAGKTKE-OH |
| 5 | 29-42 | H-AAGKTKEGVLYVGS-OH |
| 6 | 36-49 | H-GVLYVGSKTKEGVV-OH |
| 7 | 43-56 | H-KTKEGVVHGVATVA-OH |
| 8 | 50-63 | H-HGVATVAEKTKEQV-OH |
| 9 | 57-70 | H-EKTKEQVTNVGGAV-OH |
| 10 | 64-77 | H-TNVGGAVVTGVTAV-OH |
| 11 | 71-84 | H-VTGVTAVAQKTVEG-OH |
| 12 | 78-91 | H-AQKTVEGAGSIAAA-OH |
| 13 | 85-98 | H-AGSIAAATGFVKKD-OH |
| 14 | 92-105 | H-TGFVKKDQLGKNEE-OH |
| 15 | 99-112 | H-QLGKNEEGAPQEGI-OH |
| 16 | 106-119 | H-GAPQEGILEDMPVD-OH |
| 17 | 113-126 | H-LEDMPVDPDNEAYE-OH |
| 18 | 120-133 | H-PDNEAYEMPSEEGY-OH |
| 19 | 127-140 | H-MPSEEGYQDYEPEA-OH |

Figure 8:
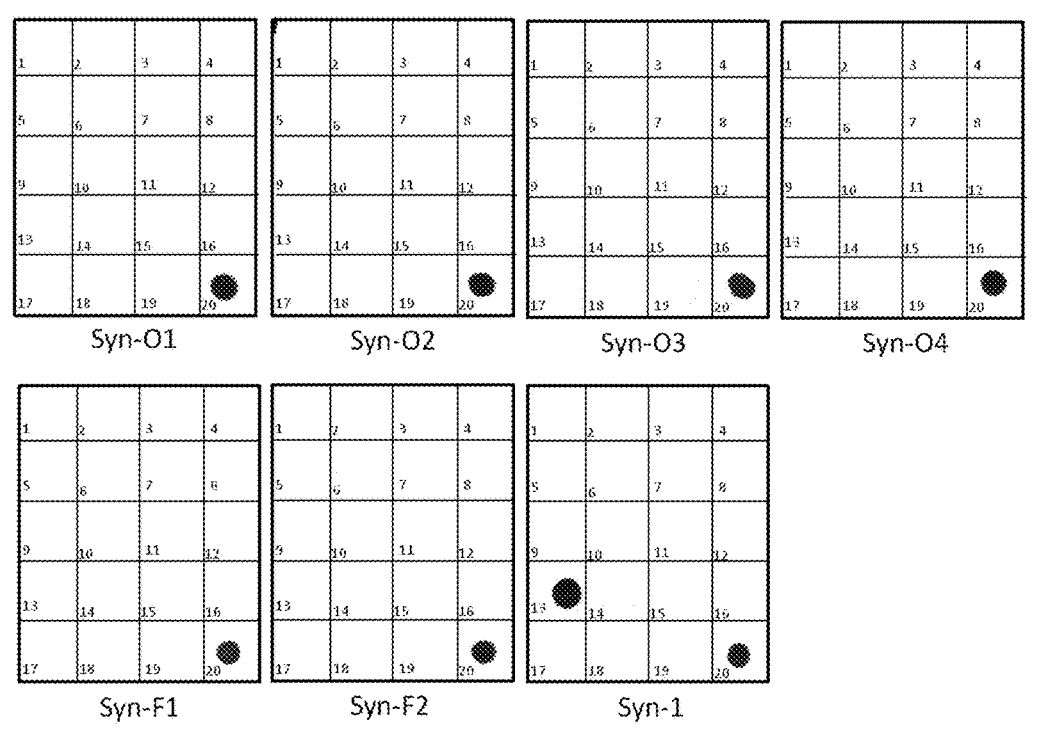

Pepscan by Dot Blot
Nitrocellulose membrane was pretreated with 0.1% EDC (1-Ethyl-3-[3-dimethylaminopropyl] carbodiimide hydrochloride), in PBS, for 10 min at room temperature and air-dried. 200 ng (in 5 µl PBS, pH 7.4) of the peptides 1-19 (α-synuclein peptide library, table 5) and 50 ng of the α-synuclein fibrils (spot 20) were spotted onto the membrane.- After air-drying the membranes were blocked with 5% skimmed milk in PBST and incubated for 1 h at room temperature. The membranes were washed three times with PBST before incubating (50 ng/ml in PBST) with Syn-F1, Syn-F2, Syn-O1, Syn-O2, Syn-O3, Syn-O4 or Syn-1 monoclonal antibodies and incubated for 2h at room temperature. The membranes were washed with PBST and incubated with 1:20000 diluted (in PBST) goat anti-mouse IgG-HRP (Jackson immunoResearch). The blots were developed using Super signal West Pico chemiluminescent substrate (Thermo Scientific). The results of the pepscan be seen in FIG. 8.

The pepscan results using dot blot suggested that the mAbs, Syn-O1, Syn-O2, Syn-O3, Syn-O4, Syn-F1, or Syn-F2, do not recognize a linear epitope.

Pepscan by ELISA

To confirm the pepscan results using dot blot the mAbs were also tested by Pepscan using ELISA. A 384 well black maxisorp plate (NUNC) was coated with 50 μl (500 ng/well) of peptides (α-synuclein peptides 1-19 as detailed in Table 5) in 0.2 M NaHCO$_3$, pH 9.6 and 50 μl (100 ng/well) α-synuclein fibrils in PBS pH 7.4 by overnight incubation at 37° C. allowing for complete drying. The plate was washed three times with PBST and blocked with 100 μl of blocking buffer (2.25% gelatin in PBST) for 1 h at room temperature. After washing the plate three times with PBST, 50 μl (100 ng/ml) of the mAbs (Syn-F1, Syn-F2, Syn-O1, Syn-O2, Syn-O3 and Syn-O4), and the control antibodies (50 μl (100 ng/ml) of Syn-1 (Mouse anti-α-synuclein; BD Bioscience), 50 μl (100 ng/ml) of N-19 (Goat anti-α-synuclein; Santa Cruz Biotechnology), 50 μl (100 ng/ml) of 211 (Mouse anti-α-synuclein; Santa Cruz Biotechnology), 50 μl (200 ng/ml) of FL-140 (Rabbit anti-α-synuclein; Santa Cruz Biotechnology), 50 μl (1 g/ml) of 5C2 (Mouse anti-α-synuclein; Santa Cruz Biotechnology) and 50 μl (1 μg/ml) of 3B6 (Mouse anti-α/β-synuclein; Santa Cruz Biotechnology) were added and incubated for 1 h at room temperature. The plate was washed with PBST and either goat anti-mouse IgG-HRP conjugate (1/20000; Jackson ImmunoResearch) or goat anti-rabbit IgG-HRP (1/5000; Jackson Immunoresearch) conjugate or diluted chicken anti-goat IgG-HRP conjugate (1/20000) were added and incubated the plates for 1 h at room temperature. The plate was washed with PBST and 50 μl of substrate (SuperSignal ELISA Femto Maximum Sensitivity Substrate, Thermo Scientific) was added and immediately read the plate using Victor X3 microtiter plate reader. After the ELISA signals were measured, the plate was also exposed onto X-ray film to develop the spots.

Figure 10A:
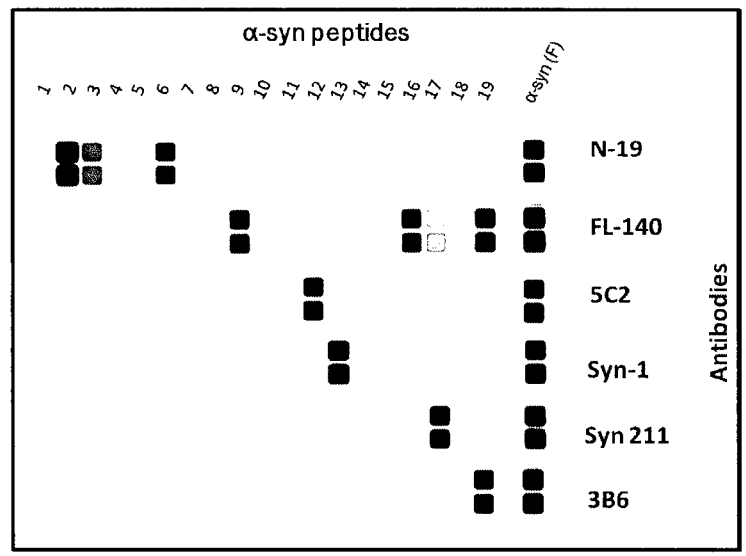
FIGS. 10A and 10B show the plots for the X-ray film placed over the plate of the Pepscan ELISA as described in Example 7. The plot for control antibodies, N-19, FL-140, 5C2, Syn-1, Syn-211, 3B6 is shown in FIG. 10A. The antibodies of the invention, Syn-F1, Syn-F2, Syn-O1, Syn-O2, Syn-O3 and Syn-O4 are shown in FIG. 10B.
Figure 10B:
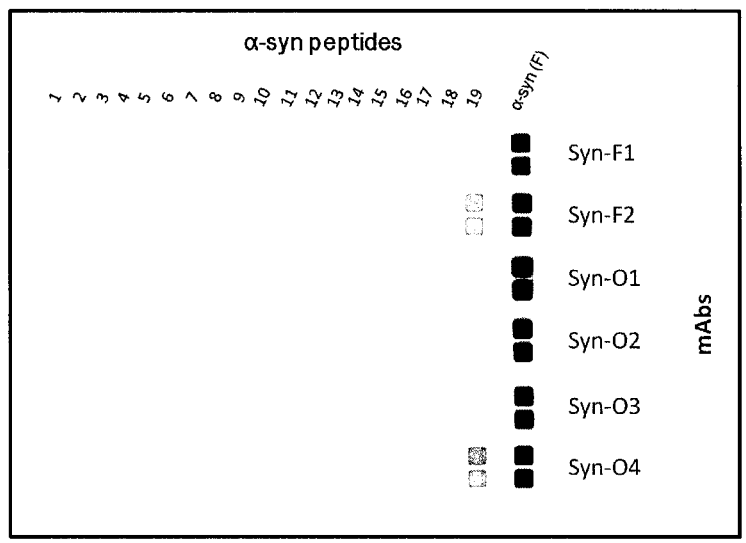
Figure 11A:
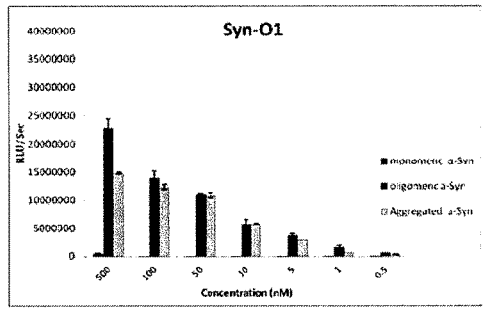
FIGS. 11A-11G show the results of the sandwich ELISA for the detection of α-synuclein aggregates as described in Example 8. The antibodies Syn-F1 (FIG. 11E), Syn-F2 (FIG. 11E), Syn-O1 (FIG. 11A), Syn-O2 (FIG. 11B), Syn-O3 (FIG. 11C) and Syn-O4 (FIG. 11D), and Syn-1 (FIG. 11G) antibody was used as the capturing antibody, FL-140 was used as the detection antibody.
Figure 11B:
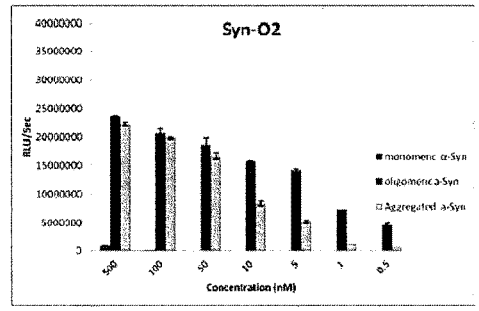
Figure 11C:
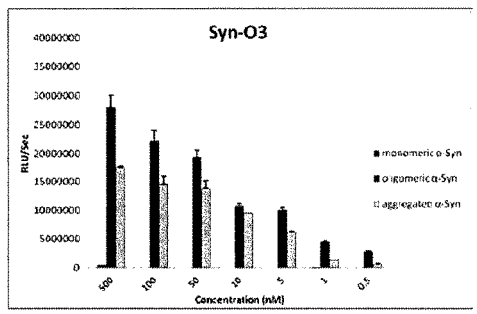
Figure 11D:
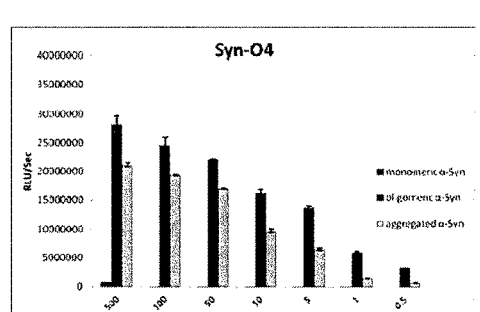
Figure 11E:
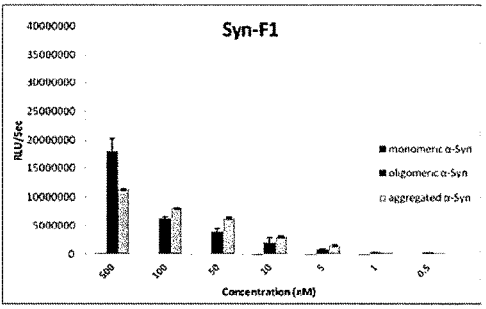
Figure 11F:
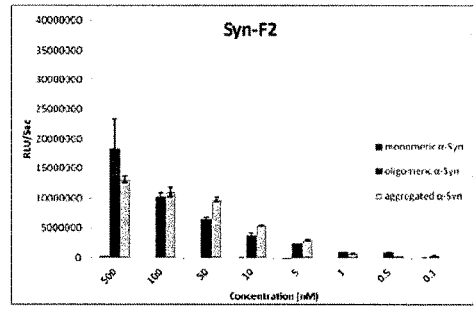
Figure 11G:
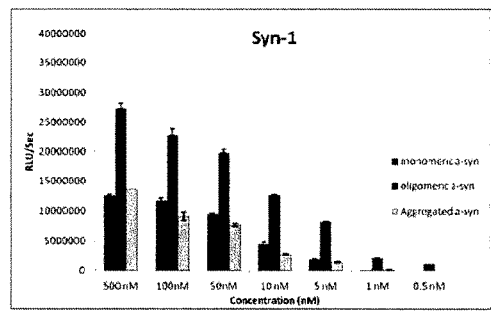

The results of the Pepscan screening by ELISA can be seen in FIGS. 9A-9L and FIGS. 10A and 10B (control antibodies, FIG. 10A, antibodies of the invention, FIG. 10B). The pepscan method by ELISA also showed that the antibodies did not react to any of the peptides but reacted slightly with the C-terminal peptide (127-140) suggesting an involvement of the C-terminal region in forming the conformational epitope.

Example 8

Sandwich ELISA to Detect Alpha-synuclein Aggregates

The 384 well ELISA black microplate (Nunc Maxisorb, NUNC, Denmark) was coated by overnight incubation at 4° C. with 0.1 μg/ml of one of our conformational monoclonal antibodies (Syn-F1, Syn-F2, Syn-O1, Syn-O2, Syn-O3 or Syn-O4) (50 μl/well), in 200 mM NaHCO$_3$, pH 9.6.

The plate was washed four times with PBS containing 0.05% Tween-20 (PBST), and incubated with 100 μl/well of blocking buffer (PBST containing 2.5% gelatin and 1 BSA) for 2 h at 37° C.

The plate was washed four times with PBST and 50 μl of various concentrations (10, 5, 1, 0.5, 0.1, and 0.05 nM in PBS) of monomeric, oligomeric or aggregated α-synuclein were added. The plate was then incubated at 37° C. for 2.5 h.

After washing four times with PBST, 50 μl of FL-140 (rabbit polyclonal antibody, Santa Cruz Biotechnology) diluted to 1:1000 in blocking buffer was added, and incubated at 37° C. for 2 h.

After the wells were washed 4 times with PBST and 50 μl/well of Goat anti Rabbit IgG HRP (Jackson ImmunoResearch) diluted 1:10,000 in blocking buffer were added and incubated for 1.5 h at 37° C.

The plate was washed 4 times with PBST, and bound HRP activity was assayed by chemiluminescent reaction using an enhanced chemiluminescent substrate (SuperSignal ELISA Femto, Pierce Biotechnology), after which chemiluminescence in relative light units was immediately measured with a PerkinElmer microplate reader.

To confirm that the conformational mAbs detected only the aggregated forms of α-synuclein and not the monomeric forms of α-synuclein, a further ELISA assay as described above was carried out as a control using Syn-1 as the capture antibody.

The results are shown in FIGS. 11A-11G. The results shows that the confirmation mAbs Syn-F1 (FIG. 11E), Syn-F2 (FIG. 11F), Syn-O1 (FIG. 11A), Syn-O2 (FIG. 11B), Syn-O3 (FIG. 11C), and Syn-O4 (FIG. 11D), react to both oligomeric and aggregated forms of α-synuclein. Syn-1 (FIG. 11G) reacts to both monomeric and the aggregated forms of α-synuclein.

Whilst the ELISA shows no detection of the monomeric form of α-synuclein and detection of both the oligomeric and fibril forms of α-synuclein by all the mAbs, the results of the ELISA showed that for Syn-F1 and Syn-F2 there was some specificity towards α-synuclein fibrils over oligomeric forms of α-synucleins.

Example 9

Sandwich ELISA to Detect Aggregated Phosphorylated Ser129-alpha-synuclein (β-S129-α-Syn The 384 well ELISA black microplate (Nunc Maxisorb, NUNC, Denmark) was coated by overnight incubation at 4° C. with 0.1 μg/ml of one of our conformational monoclonal antibodies (Syn-F2, Syn-O2) (50 μl/well), in 200 mM NaHCO$_3$, pH 9.6.

The plate was washed four times with PBS containing 0.05% Tween-20 (PBST), and incubated with 100 μl/well of blocking buffer (PBST containing 2.5% gelatin and 1 BSA) for 2 h at 37° C.

The plate was washed four times with PBST and 50 μl of various concentrations (1, 0.5, 0.1, 0.05, 0.01, 0.005 nM in PBS) of monomeric p-S129-α-syn or aggregated p-S129-α-syn were added. The plate was then incubated at 37° C. for 2.5 h.

After washing four times with PBST, 50 μl of rabbit anti-p-S129-α-synuclein (Epitomics) diluted to 1:1000 in blocking buffer was added, and incubated at 37° C. for 2 h.

After the wells were washed 4 times with PBST and 50 μl/well of Goat anti Rabbit IgG HRP (Jackson ImmunoResearch) diluted 1:10,000 in blocking buffer were added and incubated for 1.5 h at 37° C.

The plate was washed 4 times with PBST, and bound HRP activity was assayed by chemiluminescent reaction using an enhanced chemiluminescent substrate (SuperSignal ELISA Femto, Pierce Biotechnology), after which chemiluminescence in relative light units was immediately measured with a PerkinElmer microplate reader.

To confirm that the conformational mAbs detected only the aggregated forms of α-synuclein and not the monomeric form of α-synuclein, a further ELISA assay as described above was carried out as a control using Syn-1 as the capture antibody.

Figure 12A:
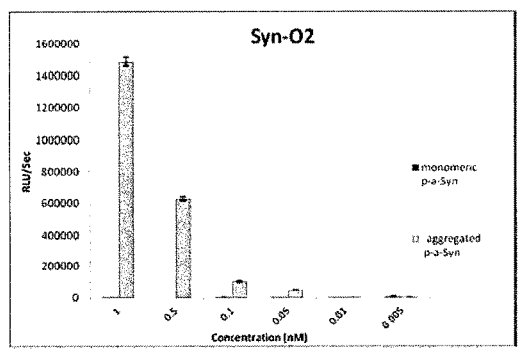
FIGS. 12A-12C show the results of the sandwich ELISA for the detection of phosphorylated Ser129-α-synuclein aggregates as described in Example 9. Antibodies Syn-O2 (FIG. 12A) and Syn-F2 (FIG. 12B), and Syn-1 (FIG. 12C) were used as the capturing antibody and rabbit anti-p-S129-α-synuclein was used as the detection antibody.
Figure 12B:
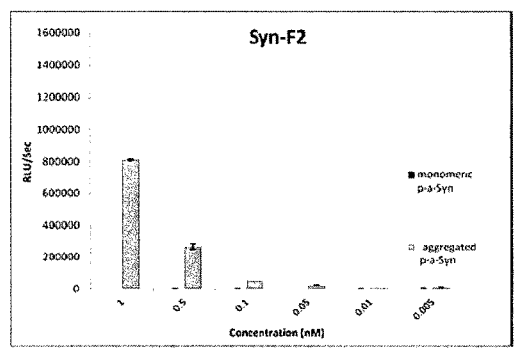
Figure 12C:
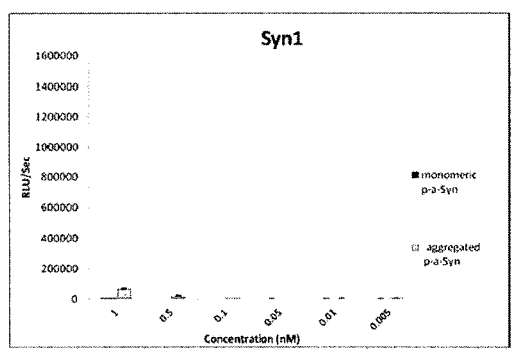

The results can be seen in FIGS. 12A-12C. The results shows that the confirmation mAbs Syn-F2 (FIG. 12B) and Syn-O2 (FIG. 12A), react to aggregated phosphorylated α-synuclein forms. Syn-1 (FIG. 12C) showed a similar but in both cases low reaction to both monomeric and the aggregated forms of phoshorylated S129 α-synuclein.

The aggregation and phosphorylation of synuclein is thought to play a critical role in PD pathogenesis. Therefore detection of phosphorylated or non-phosphorylated forms of α-synuclein in biological fluids can be used as a potential biological marked for PD.

An ELISA assay has been developed that can specifically detect the aggregated forms of α-synuclein and does not detect the monomeric forms of α-synuclein. The assay uses the antibodies Syn-F1, Syn-F2, Syn-O1, Syn-O2, Syn-O3, or Syn-O4 as the capture antibodies, followed by detection with antibodies such as FL-140 (a rabbit polyclonal antibody raised against full length α-synuclein, Santa Cruz Biotechnology) for aggregated α-synuclein, or a rabbit anti-p-S129-α-synuclein (Epitomics) for aggregates of p-S129-α-synuclein.

Example 10

Immunohistochemistry

The mAbs were tested using peroxidase immunohistochemistry in brain sections from Parkinson's disease case. Syn-F1 and Syn-O2 were used at 1 in 10000 (0.1 μg/ml) dilution whereas Syn-F2, Syn-O1, Syn-O3 and Syn-O4 were used at 1 in 5000 (0.2 μg/ml) dilution. A mouse negative control slide was also processed simultaneously, where all immunohistochemical steps were included but the primary antibody was omitted.

Results

Figure 13:
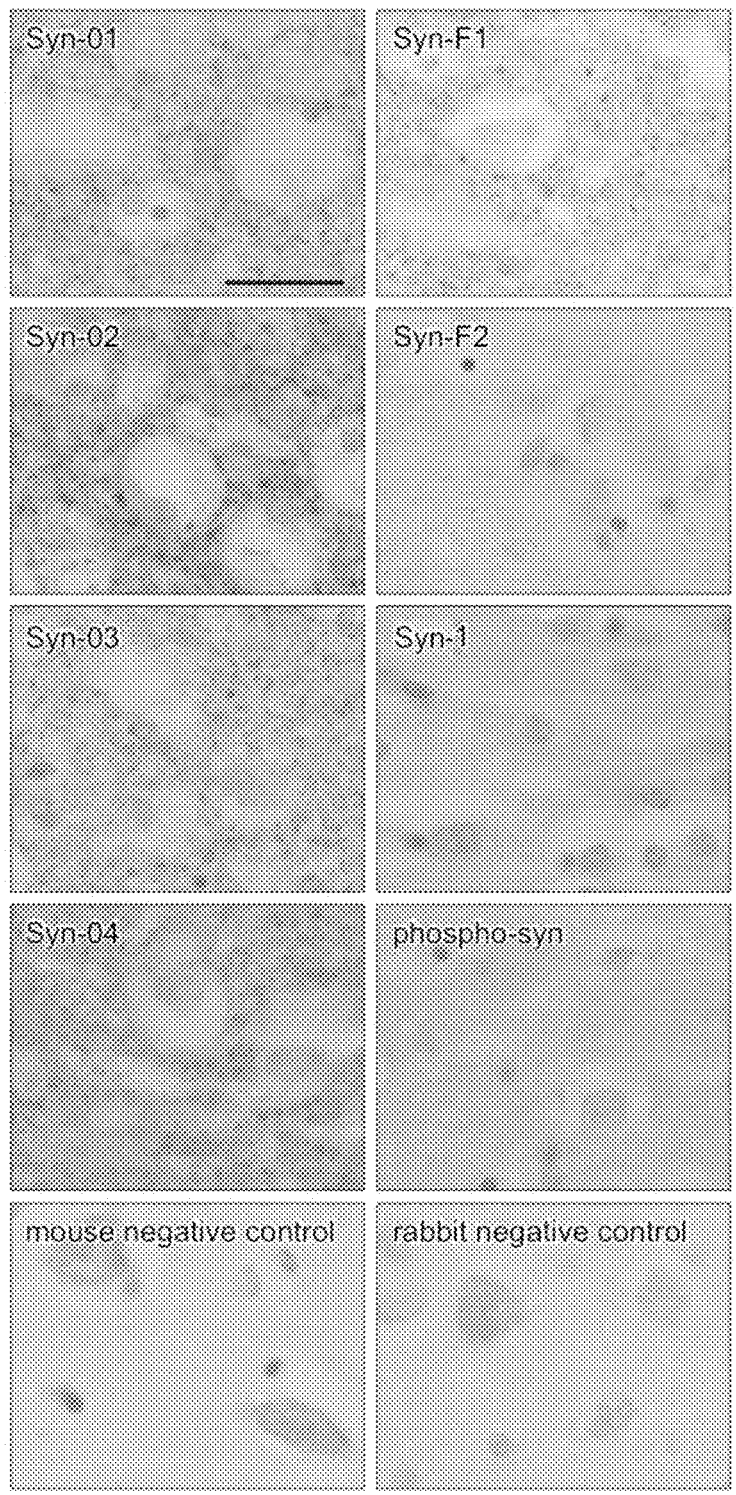
FIG. 13 shows the immunhistochemical analysis of tissues from control cases from subjects without Parkinson diseases as described in Example 10.
Figure 14:
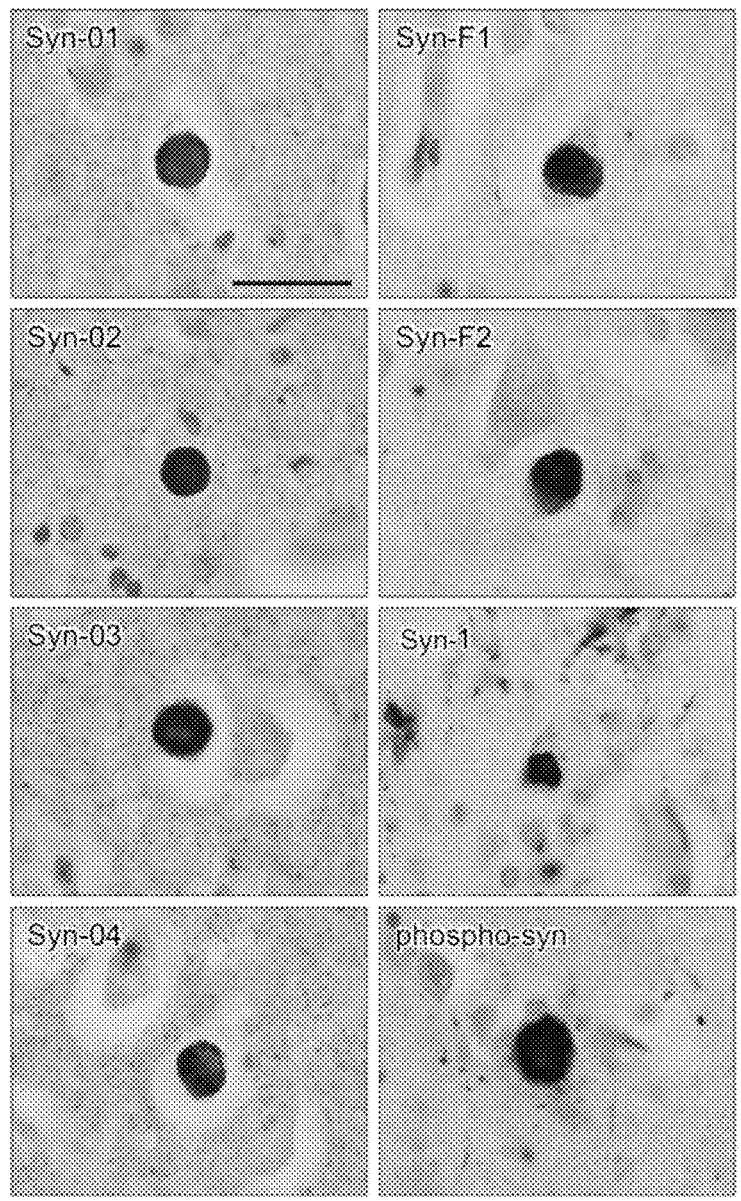
FIG. 14 shows the immunhistochemical analysis of tissues from Parkinson's disease cases as described in Example 10.
Figure 15:
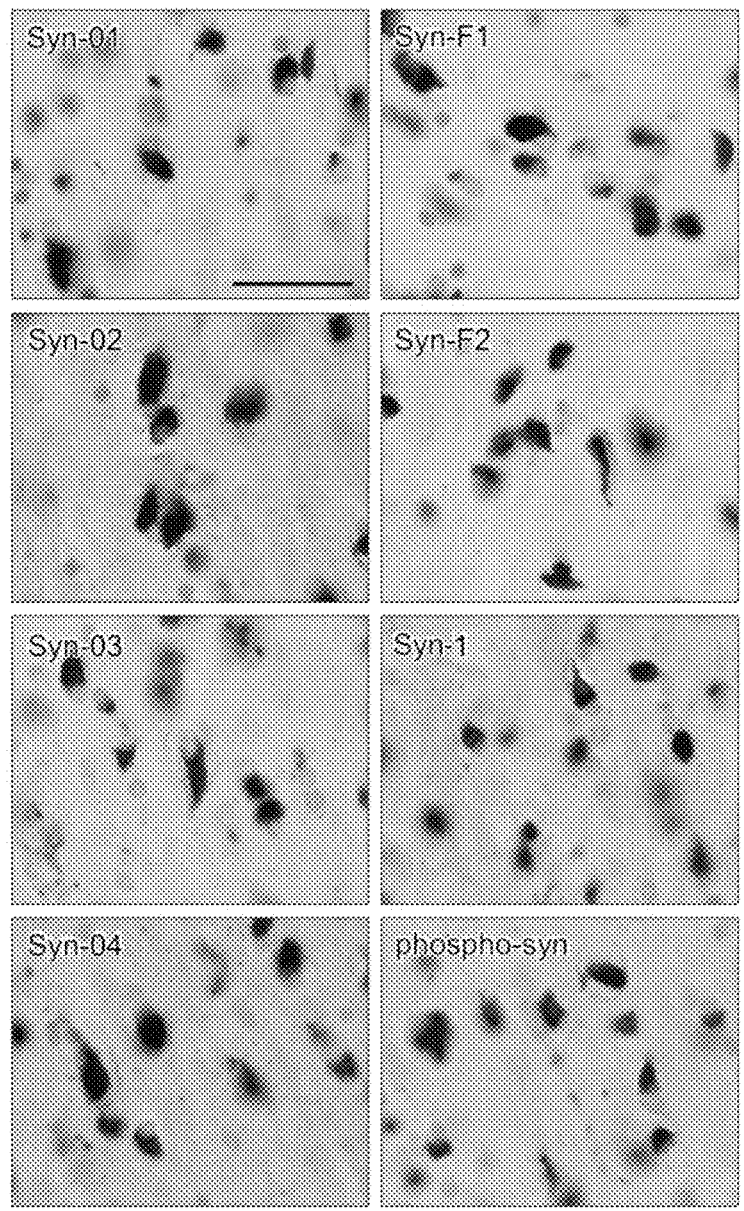
FIG. 15 shows the immunhistochemical analysis of tissues from multiple system atrophy cases as described in Example 10.

The mAbs have been worked up using peroxidase immunohistochemistry in a Parkinson's disease (PD) and Multisystem atrophy (MSA) cases. All antibodies produced intense immunostaining in Lewy bodies and Lewy neuritis in PD brains (FIG. 14), and glial cytoplasmic inclusions in white matter oligodendrocytes of multiple system atrophy brains (FIG. 15). A mouse negative control slide was also processed and did not produce any immunoreactivity in the section (FIG. 13).

In the control cases (FIG. 13) the images show sections immunostained for our mAbs and the commercially available mouse monoclonal anti-α-synuclein antibody (Syn-1) or mouse monoclonal anti-phosphorylated Ser129 α-synuclein (phospho-syn) in the anterior cingulate cortex from a control case. A mouse and rabbit negative control slide were also processed simultaneously. All sections were counterstained with Cresyl violet (blue) to visualise cell nuclei and membranes. The same adjustments to brightness were applied to all images. Scale bar represents 20 μm (applies to all panels).

In the Parkinson's disease case (FIG. 14) images shows Lewy bodies immunoreactive for our mAbs and the commercially available mouse monoclonal anti-α-synuclein antibody (Syn-1) or mouse monoclonal anti-phosphorylated Ser129 α-synuclein antibody (phospho-syn) in the anterior cingulate cortex from a Parkinson's disease case. All sections were counterstained with Cresyl violet (blue) to visualize cell nuclei and membranes. The same adjustments to brightness were applied to all images. Scale bar represents 20 μm (applies to all panels).

In the Multiple system atrophy case (FIG. 15) images show glial-cell inclusions immunoreactive for our mAbs and commercially available mouse monoclonal anti-α-synuclein antibody (Syn-1) or mouse monoclonal anti-phosphorylated Ser129 α-synuclein antibody (phospho-syn) in the putamen from an MSA case. Sections were counterstained with Cresyl violet (blue) to visualise cell nuclei and membranes. The same adjustments to brightness were applied to all images. Scale bar represents 20 μm (applies to all panels).

Example 11

Brain tissues samples from patients known to have neurodegenerative disorders were tested with the Syn-O2 antibody. The antibody was used at a 1 in 5000 (0.2 μg/ml) dilution. The antibodies produced intense staining in all patient samples.

Figure 16A:
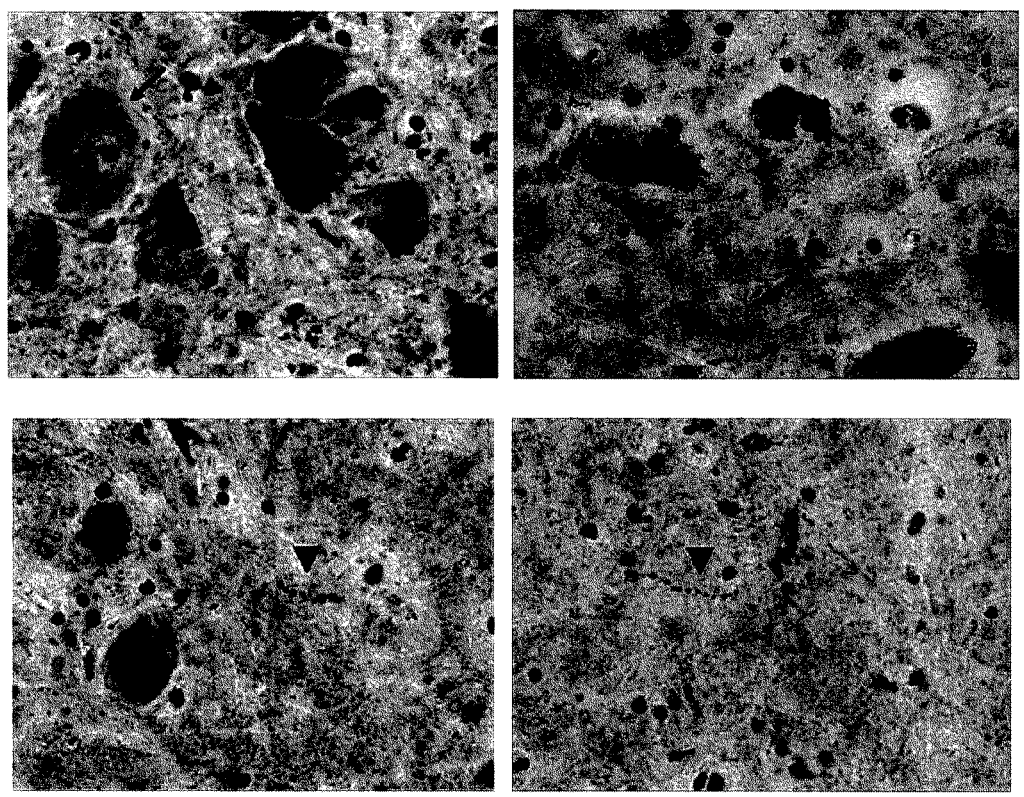
FIGS. 16A-16C show the results of Syn-O2 staining in tissues samples from a Parkin carrier PD patient (FIG. 16A), a progressive DLB patient (FIG. 16B) and a classical PD patient (FIG. 16C) as described in Example 11.

Patient A was known to have autosomal recessive early-onset Parkinsonism with heterozygous missense mutation in combination with heterozygous exon deletion in parkin gene. As shown in FIG. 16A oligomeric α-synuclein was observed in synapses and cellular processes (arrowheads). Very small aggregates were visible within the cytoplasm of the few neuromelanin-containing neurons (arrow).

Figure 16B:
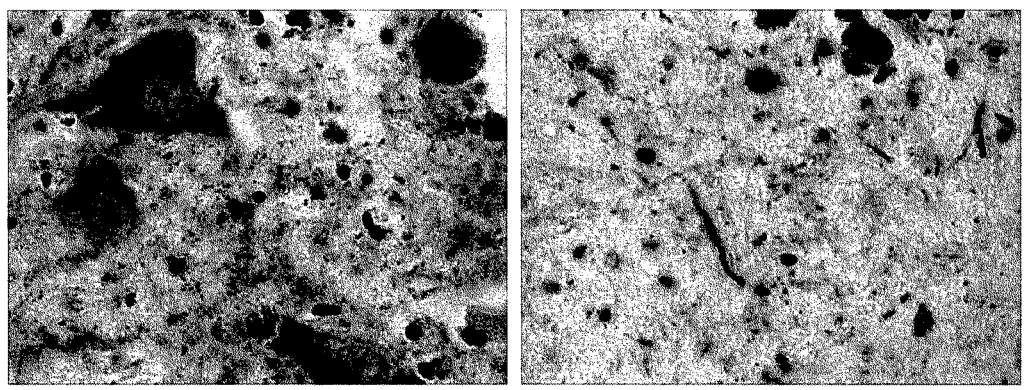

Patient B was aprogressive DLB patent. As shown in FIG. 16B oligomeric α-synuclein immunoreactivity was observed in synapses, Lewy neurite-like structures and extracellular aggregates.

Figure 16C:
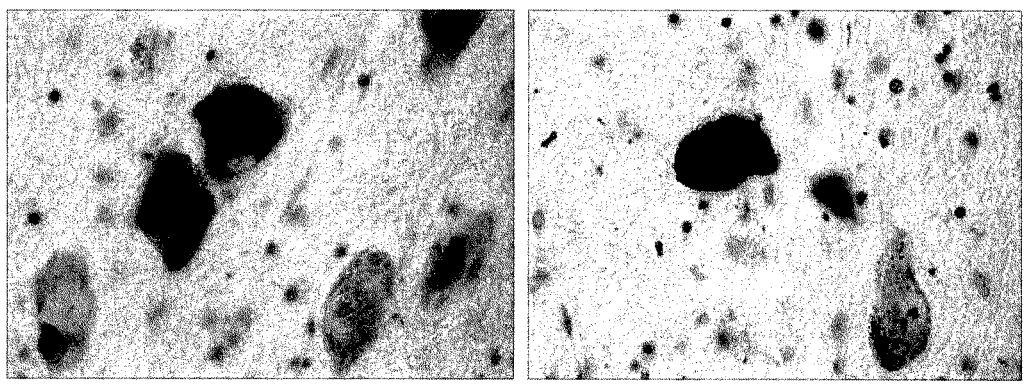
Figure 17:
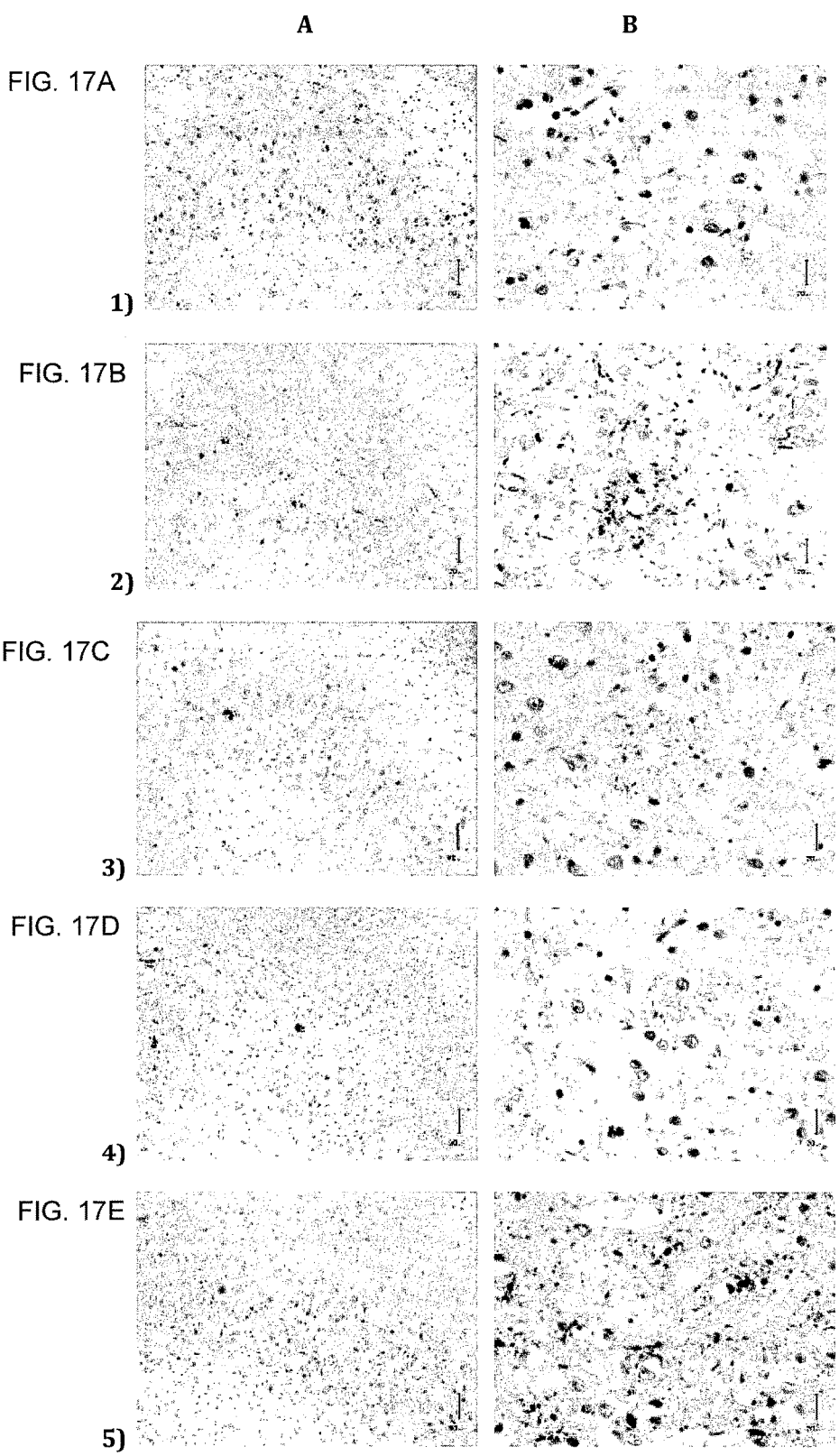
FIGS. 17A-17E show the results of staining with the Syn-F2 antibodies of treatments of brain sections from the CA2 region of hippocampus (A), and the Entorhinal cortex neutries (B) as described in Example 12. The sections underwent the following treatment: 1) no pre-treatment (FIG. 17A), 2) autoclaving at 120° C. for 10 minutes in citrate buffer (FIG. 17B), 3) formic acid for 15 mins (FIG. 17C) or 4) 20 μg/ml proteinase K treatment (FIG. 17D). A control 5) with the Syn-1 antibody was carried out on tissues samples which had been treated with formic acid for 15 mins (FIG. 17E).

Patient C has late-onset idiopathic Parkinson. As shown in FIG. 16C oligomeric α-synuclein immunoreactivity was observed in Lewy body-like intracytoplasmic inclusions and Lewy neurites.

These results shows that antibodies of the invention can be used to diagnosis neurodegenerative diseases associated with α-synuclein.

Example 12

Different sections of brain tissues samples (CA2 region of hippocampus, Entorhinal cortex superficial layers 1-3, Entorhinal cortex superficial layers 4-6, Entorhinal cortex neutries) were tested with the Syn-O1, Syn-O2, Syn-O3 Syn-O4, Syn-F1 and Syn-F2 antibodies. The antibodies were used at a 1 in 5000 dilution. The brain samples went under 1 of four treatments 1) no pretreatment, 2) autoclaving at 120° C. for 10 minutes in citrate buffer, 3) formic acid for 15 mins or 4) 20 μg/ml proteinase K treatment.

Incubation was overnight at 4° C. Detection was with Histostain HP kit with Romulin as Chromogen. A control antibody, Syn-1, was used at a dilution of 1:1000. The tissues samples tested with the control antibody were pretreated with Formic acid for 15 mins.

The results showed that the antibodies worked even without pretreatment of the brain tissues. However the antibodies are picked up better with pretreatment. Protein K treated samples showed the better results. Proteinase K treatment is known to enhance the immunoreactivity of abnormal synuclein (i.e. intracytoplasmic aggregates) and to decrease diffuse synaptic staining. The results for the control antibody and the syn-F2 antibody in the CA2 region of hippocampus (A), and the Entorhinal cortex neutries (B) are shown in FIGS. 17A-17E.

Example 13

The polynucleotide and amino acid sequences of the variable regions of the heavy chain and light chain for the six antibody clones Syn-F1, Syn-F2, Syn-O1, Syn-O2, Syn-O3 and Syn-O4 was determined.

RNA was extracted from the hybridoma clones Syn-F1, Syn-F2, Syn-O1, Syn-O2, Syn-O3 and Syn-O4 using TRIzol® Plus RNA purification System (Invitrogen) according to the technical manual. The isolated Total RNA was analysed by argose gel electrophoresis.

Total RNA was reversed transcribed into cDNA using isotype-specific anti-sense primers or universal primers using the SuperScript™ III First-strand synthesis System according to the technical manual. The antibody fragments of VH and VL were amplified according to the standard operating procedure of RACE of GenScript.

The amplified antibody fragments were cloned into a cloning vector using standard molecule cloning techniques. Colony PCR screening was performed to identify clones with inserts of correct sizes. No less than five single clones with inserts of the correct size were sequenced for each antibody fragment.

The DNA sequences were determined for each VH and VL region, and the corresponding amino acid sequences were determined. The leader sequence, the framework regions (FR1, FR2, FR3 and FR4) and the complementarity determining regions (CDR1, CDR2 and CDR3) were determined for each heavy and light chain variable region. The results are shown in Table 6. The CDR1, CDR2 and CDR3 polynucleotide and amino acid sequences are shown in SEQ ID NOs:13-48.

The DNA sequences encoding VH and VL regions of Syn-F1 are provided in SEQ ID NO: 1 and 3 respectively. The VH and VL amino acid sequences of Syn-F1 are provided in SEQ ID NO: 2 and 4. The CDR1, CDR2, and CDR3 regions of the VH region of Syn-F1 are set forth in SEQ ID NO: 13, 14 and 15 respectively. The corresponding amino acid sequences are set forth in SEQ ID NO: 16, 17 and 18. The CDR1, CDR2, and CDR3 regions of the VL region of Syn-F1 are set forth in SEQ ID NO: 19, 20 and 21 respectively. The corresponding amino acid sequences are set forth in SEQ ID NO: 22, 23, and 24.

The DNA sequences encoding VH and VL regions of Syn-F2 are provided in SEQ ID NO: 5 and 7 respectively. The VH and VL amino acid sequences of Syn-F2 are provided in SEQ ID NO: 6 and 8. The CDR1, CDR2, and CDR3 regions of the VH region of Syn-F2 are set forth in SEQ ID NO: 25, 26 and 27 respectively. The corresponding amino acid sequences are set forth in SEQ ID NO: 28, 29 and 30. The CDR1, CDR2, and CDR3 regions of the VL region of Syn-F1 are set forth in SEQ ID NO: 31, 32 and 33 respectively. The corresponding amino acid sequences are set forth in SEQ ID NO: 34, 35 and 36.

The DNA sequences encoding VH and VL regions of Syn-O1, Syn-O2, Syn-O3 and Syn-O4 are provided in SEQ ID NO: 9 and 11 respectively. The VH and VL amino acid sequences of Syn-O1, Syn-O2, Syn-O3 and Syn-O4 are provided in SEQ ID NO: 10 and 12. The CDR1, CDR2, and CDR3 regions of the VH regions of Syn-O1, Syn-O2, Syn-O3 and Syn-O4 are set forth in SEQ ID NO: 37, 38 and 39 respectively. The corresponding amino acid sequences are set forth in SEQ ID NO: 40, 41 and 42. The CDR1, CDR2, and CDR3 regions of the VL regions of Syn-O1, Syn-O2, Syn-O3 and Syn-O4 are set forth in SEQ ID NO: 43, 44 and 45 respectively. The corresponding amino acid sequences are set forth in SEQ ID NO: 46, 47 and 48.

It was found that sequences of the VH and VL regions from Syn-O1, Syn-O2, Syn-O3 and Syn-O4 were the same.

TABLE 6

| ANTIBODY | SEQ ID NO: | SEQUENCE (Leader-FR1-CDR1-FR2-CDR2-FR3-CDR3-FR4) |
|---|---|---|
| SYN-F1 (VH) | 1 | ATGGACTCCAGGCTCAATTTAGTTTTCCTTGTCCTTA TTTTAAAAGGTGTCCAGTGT GATGTGCAGCTGGTGGA GTCTGGGGGAGACTTAGTGCAGCCTGGAGGGTCCCGG AAACTCTCCTGTGCAGCCTCT GGATTCACTTTCAGTAG CTTTGGAATGCACTGGGTTCGTCAGGCTCCAGAGAAGG GGCTGGAGTGGGTCGCA TACATTAATAGTGGCAGTAGT ACCATCTACTATGCAGACACAGTGAAGGGC CGATTCAC CATCTCCAGAGACAATCCCAAGAACACCCTGTTCCTGC AGATGACCAGTCTAAGGTCTGAGGACACGGCCATGTAT TACTGTGCAA GGGGAAATAACCCTGGGACGGGATATTA CTATTCTATGGACTAC TGGGGTCAGGGAACCTCAGTCA CCGTCTCCTCA |
| SYN-F1 (VH) | 2 | MDSRLNLVFLVLILKGVQC DVQLVESGGDLVQPGGSRKLSCAAS GFTFSSFGMH WVRQAPEKGLEWVA YINSGSSTIYYADTVKG RFTISRDNPKNTLFLQMTSLRSEDTAMYYCAR GNNPGTGYYY SMDY WGQGTSVTVSS |
| SYN-F1 (VL) | 3 | ATGATGAGTCCTGCCCAGTTCCTGTTTCTGTTAGTGCTCT GGA TTCAGGAAACCAACGGTG ATGTTGTGATGACCCAGACTCCAC TCACTTTGTCGGTTACCATTGGACAACCAGCCTCTATCTCT TGC AAGTCAAGTCAGAGCCTCTTATATAGTAATGGAAAAA CCTATTTGAATTGGTTATTACAGAGGCCAGGCCAGTCTCC AAAGCGCCTAATCTAT CTGGTGTCTAAACTGGACTCTGGA GTCCCTGACAGGTTCACTGGCAGTGGATCAGGAACAGATT |

TABLE 6-continued

| ANTIBODY | SEQ ID NO: | SEQUENCE (Leader-FR1-CDR1-FR2-CDR2-FR3-CDR3-FR4) |
|---|---|---|
| | | TTACACTGAAAATCAGCAGAGTGGAGGCTGAGGATTTGGG AGTTTATTACTGC<u>GTGCAAGGTACACATTTTCCCACG</u>TTCG GAGTGGGGACCAAGCTGGAAATAAAA |
| SYN-F1 (VL) | 4 | *MMSPAQFLFLLVLWIQETNG* DVVMTQTPLTLSVTIGQPASISC <u>KSSQSLLYSNGKTYLN</u>WLLQRPGQSPKRLIY<u>LVSKLDS</u>GVPD RF TGSGSGTDFTLKISRVEAEDLGVYYC<u>VQGTHFPT</u>FGVGTKLE IK |
| SYN-F2 (VH) | 5 | *ATGGACTCCAGGCTCAATTTAGTTTTCCTTGTCCTTATTTT AAAAGGTGTCCAGTGT* GATGTGCAGCTGGTGGAGTCTGGGGGAGGCT TAGTGCAGCCTGGAGGGTCCCGGAAACTCTCCTGTGCAG CCTCT<u>GGATTCACTTTCAGTAGCTTTGGAATGCAC</u>TGGGT TCGTCAGGCTCCAGAGAAGGGGCTGGAGTGGGTCGCA<u>TA CATTAGTAGTGGCAGTAGTACCATCTACTATGCAGACACA GTGAAGGGC</u>CGATTCACCATCTCCAGAGACAATCCCAAGA ACACCCTGTTCCTGCAAATGACCAGTCTAAGGTCTGAGGA CACGGCCATGTATTACTGTGCAAGA<u>GGAAATAACCCTGGG ACGGGATATTACTATGCTATGGACTAC</u>TGGGGTCAAGGAA CCTCAGTCACCGTCTCCTCA |
| SYN-F2 (VH) | 6 | *MDSRLNLVFLVLILKGVQC* DVQLVESGGGLVQPGGSRKLSCAAS <u>GFTFSSFGMH</u>WVRQAPEKGLEWVA<u>YISSGSSTIYYADTVKG</u> RFTISRDNPKNTLFLQMTSLRSEDTAMYYCAR<u>GNNPGTGYY YAMDY</u>WGQGTSVTVSS |
| SYN-F2 (VL) | 7 | *ATGATGAGTCCTGCCCAGTTCCTGTTTCTGTTAGTGCTCT GGATTCAGGAAACCAACGGT* GATGTTGTGATGACCCAGACTCCACTCA CTTTGTCGGTTACCATTGGACAACAGCCTCTATCTCTTGC <u>AAGTCAAGTCAGAGCCTCTTATATAGTAATGGAAAAACCTA TTTGA</u>ATTGGTTATTACAGAGGCCAGGCCAGTCTCCAAAG CGCCTAATCTAT<u>CTGGTGTCTAAACTGGACTCT</u>GGAGTCC CTGACAGGTTCACTGGCAGTGGATCAGGAACAGATTTTAC ACTGAAAATCAGCAGAGTGGAGGCTGAGGATTTGGGAGT TTATTACTGC<u>GTGCAAGGTACACATTTTCCCACG</u>TTCGGA GGGGGGACCAAGCTGGAAATAAAA |
| SYN-F2 (VL) | 8 | *MMSPAQFLFLLVLWIQETNG* DVVMTQTPLTLSVTIGQPASISC<u>KS SQSLLYSNGKTYLN</u>WLLQRPGQSPKRLIY<u>LVSKLDS</u>GVPDRF TGSGSGTDFTLKISRVEAEDLGVYYC<u>VQGTHFPT</u>FGGGTKL EIK |
| SYN-O1 (VH) | 9 | *ATGGTGTTGGGGCTTAAGTGGGTTTTCTTTGTTGTTTTTA TCAAGGTGTGCATTGT* GAGGTGCAGCTTGTTGAGTCTGGTGGAGGATT GGTGCAGCCTAAAGGATCATTGAAACTCTCATGTGCCGCC TCT<u>GGTTTCACCTTCAATACCTATGCCATGCAC</u>TGGGTCC GCCAGGCTCCAGGAAAGGGTTTGGAATGGGTTGCT<u>CGCA TAAGAAGTAAAAGTAGTAATTATGCAACATATTATGCCGAC TCAGTGAAAGAC</u>AGATTCACCATCTCCAGAGATGATTCAC AAAGCATGCTCTATCTGCAAATGAACAACCTGAAAACTGA GGACACAGCCATGTATTACTGTGTGAGA<u>CCCCTTAAGTGG TACTTCGATGTC</u>TGGGGCACAGGGACCACGGTCACCGTC TCCTCA |
| SYN-O1 (VH) | 10 | *MVLGLKWVFFVVFYQGVHC* EVQLVESGGGLVQPKGSLKLSCAAS <u>GFTFNTYAMH</u>WVRQAPGKGLEWVA<u>RIRSKSSNYATYYADS VKD</u>RFTISRDDSQSMLYLQMNNLKTEDTAMYYCVR<u>PLKVVYF DV</u>WGTGTTVTVSS |
| SYN-O1 (VL) | 11 | *ATGGATTTTCAAGTGCAGATTTTCAGCTTCCTGCTAATCAG TGCCTCAGTATCCAGAGGA* CAAATTGTTCTCACCCAGTCTCCAGCAAT CTTGTCTGCATCTCCAGGGGAGAAGGTCACCATGACCTGC <u>AGTGCCAGCTCAACTGTTAATTACATGCAC</u>TGGTACCAGC AGAAGTCAGGCACCTCCCCCAAAATATGGATTTAT<u>GACAC ATCCAAACTGGCTTCT</u>GGAGTCCCTGCTCGCTTCAGTGGC AGTGGGTCTGGGACCTCTTACTCTCTCACAATCAGCAGCA |

TABLE 6-continued

| ANTIBODY | SEQ ID NO: | SEQUENCE (Leader-FR1-CDR1-FR2-CDR2-FR3-CDR3-FR4) |
|---|---|---|
| | | TGGAGGCTGAAGATGCTGCCACTTATTACTGC<u>CAGCAGTG</u><br><u>GAATAGTAACCCACCCACG</u>TTCGGTGCTGGGACCAAGCT<br>GGAGCTGAAA |
| SYN-01 (VL) | 12 | MDFQVQIFSFLLISASVSRG<br>QIVLTQSPAILSASPGEKVTMTCSAS<br><u>STVNYMH</u>WYQQKSGTSPKIWIY<u>DTSKLAS</u>GVPARFSGSGS<br>WTSYSLTISSMEAEDAATYYC<u>QQWNSNPPT</u>FGAGTKLELK |
| SYN-02 (VH) | 9 | *ATGGTGTTGGGGCTTAAGTGGGTTTTCTTTGTTGTTTTTA*<br>*TCAAGGTGTGCATTGT*<br>GAGGTGCAGCTTGTTGAGTCTGGTGGAGGATT<br>GGTGCAGCCTAAAGGATCATTGAAACTCTCATGTGCCGCC<br>TCTGGTTTCACCTTCAATACCTATGCCATGCACTGGGTCC<br>GCCAGGCTCCAGGAAAGGGTTTGGAATGGGTTGCT<u>CGCA</u><br><u>TAAGAAGTAAAAGTAGTAATTATGCAACATATTATGCCGAC</u><br><u>TCAGTGAAAGAC</u>AGATTCACCATCTCCAGAGATGATTCAC<br>AAAGCATGCTCTATCTGCAAATGAACAACCTGAAAACTGA<br>GGACACAGCCATGTATTACTGTGTGAGA<u>CCCCTTAAGTGG</u><br><u>TACTTCGATGTC</u>TGGGGCACAGGGACCACGGTCACCGTC<br>TCCTCA |
| SYN-02 (VH) | 10 | *MVLGLKWVFFVVFYQGVHC*<br>EVQLVESGGGLVQPKGSLKLSCAAS<br><u>GFTFNTYAMH</u>WVRQAPGKGLEWVA<u>RIRSKSSNYATYYADS</u><br><u>VKD</u>RFTISRDDSQSMLYLQMNNLKTEDTAMYYCVR<u>PLKWYF</u><br><u>DV</u>WGTGTTVTVSS |
| SYN-02 (VL) | 11 | *ATGGATTTTCAAGTGCAGATTTTCAGCTTCCTGCTAATCAG*<br>*TGCCTCAGTATCCAGAGGA*CAAATTGTTCTCACCCAGTCT<br>CCAGCAA<br>TCTTGTCTGCATCTCCAGGGGAGAAGGTCACCATGACCTG<br>C<u>AGTGCCAGCTCAACTGTTAATTACATGCAC</u>TGGTACCAG<br>CAGAAGTCAGGCACCTCCCCCAAAATATGGATTTAT<u>GACA</u><br><u>CATCCAAACTGGCTTCT</u>GGAGTCCCTGCTCGCTTCAGTGG<br>CAGTGGGTCTTGGACCTCTTACTCTCTCACAATCAGCAGC<br>ATGGAGGCTGAAGATGCTGCCACTTATTACTGC<u>CAGCAGT</u><br><u>GGAATAGTAACCCACCCACG</u>TTCGGTGCTGGGACCAAGC<br>TGGAGCTGAAA |
| SYN-02 (VL) | 12 | *MDFQVQIFSFLLISASVSRG*QIVLTQSPAILSASPGEKVTMTC<br><u>SASSTVNYMH</u>WYQQKSGTSPKIWIY<u>DTSKLAS</u>GVPARFSGS<br>GSVVTSYSLTISSMEAEDAATYYC<u>QQWNSNPPT</u>FGAGTKLEL<br>K |
| Syn-03 (VH) | 9 | *ATGGTGTTGGGGCTTAAGTGGGTTTTCTTTGTTGTTTTTA*<br>*TCAAGGTGTGCATTGT*<br>GAGGTGCAGCTTGTTGAGTCTGGTGGAGGATT<br>GGTGCAGCCTAAAGGATCATTGAAACTCTCATGTGCCGCC<br>TCT<u>GGTTTCACCTTCAATACCTATGCCATGCAC</u>TGGGTCC<br>GCCAGGCTCCAGGAAAGGGTTTGGAATGGGTTGCT<u>CGCA</u><br><u>TAAGAAGTAAAAGTAGTAATTATGCAACATATTATGCCGAC</u><br><u>TCAGTGA AAGAC</u>AGATTCACCATCTCCAGAGATGATTCAC<br>AAAGCATGCTCTATCTGCAAATGAACAACCTGAAAACTGA<br>GGACACAGCCATGTATTACTGTGTGAGA<u>CCCCTTAAGTGG</u><br><u>TACTTCGATGTC</u>TGGGGCACAGGGACCACGGTCACCGTC<br>TCCTCA |
| SYN-03 (VH) | 10 | *MVLGLKWVFFVVFYQGVHC*<br>EVQLVESGGGLVQPKGSLKLSCAAS<br><u>GFTFNTYAMH</u>WVRQAPGKGLEWVA<u>RIRSKSSNYATYYADS</u><br><u>VKD</u>RFTISRDDSQSMLYLQMNNLKTEDTAMYYCVR<u>PLKWYF</u><br><u>DV</u>WGTGTTVTVSS |
| SYN-03 (VL) | 11 | *ATGGATTTTCAAGTGCAGATTTTCAGCTTCCTGCTAATCAG*<br>*TGCCTCAGTATCCAGAGGA*<br>CAAATTGTTCTCACCCAGTCTCCAGCAAT<br>CTTGTCTGCATCTCCAGGGGAGAAGGTCACCATGACCTGC<br><u>AGTGCCAGCTCAACTGTTAATTACATGCAC</u>TGGTACCAGC<br>AGAAGTCAGGCACCTCCCCCAAAATATGGATTTAT<u>GACAC</u><br><u>ATCCAAACTGGCTTCT</u>GGAGTCCCTGCTCGCTTCAGTGGC<br>AGTGGGTCTTGGACCTCTTACTCTCTCACAATCAGCAGCA<br>TGGAGGCTGAAGATGCTGCCACTTATTACTGC<u>CAGCAGTG</u><br><u>GAATAGTAACCCACCCACG</u>TTCGGTGCTGGGACCAAGCT<br>GGAGCTGAAA |

TABLE 6-continued

| ANTIBODY | SEQ ID NO: | SEQUENCE (Leader-FR1-CDR1-FR2-CDR2-FR3-CDR3-FR4) |
|---|---|---|
| SYN-03 (VL) | 12 | *MDFQVQIFSFLLISASVSRG* <br> QIVLTQSPAILSASPGEKVTMTC<u>SASS</u> <br> <u>TVNYMH</u>WYQQKSGTSPKIWIY<u>DTSKLAS</u>GVPARFSGSGSW <br> TSYSLTISSMEAEDAATYYC<u>QQWNSNPPT</u>FGAGTKLELK |
| Syn-04 (VH) | 9 | *ATGGTGTTGGGGCTTAAGTGGGTTTTCTTTGTTGTTTTTA* <br> *TCAAGGTGTGCATTGT* <br> GAGGTGCAGCTTGTTGAGTCTGGTGGAGGATT <br> GGTGCAGCCTAAAGGATCATTGAAACTCTCATGTGCCGCC <br> TCTGGTTTCACCTTCAATACCTATGCCATGCACTGGGTCC <br> GCCAGGCTCCAGGAAAGGGTTTGGAATGGGTTGCT<u>CGCA</u> <br> <u>TAAGAAGTAAAAGTAGTAATTATGCAACATATTATGCCGAC</u> <br> <u>TCAGTGAAAGAC</u>AGATTCACCATCTCCAGAGATGATTCAC <br> AAAGCATGCTCTATCTGCAAATGAACAACCTGAAAACTGA <br> GGACACAGCCATGTATTACTGTGTGAGA<u>CCCCTTAAGTGG</u> <br> <u>TACTTCGATGTC</u>TGGGGCACAGGGACCACGGTCACCGTC <br> TCCTCA |
| SYN-04 (VH) | 10 | *MVLGLKWVFFVVFYQGVHC* <br> EVQLVESGGGLVQPKGSLKLSCAAS <br> <u>GFTFNTYAMH</u>WVRQAPGKGLEWVA<u>RIRSKSSNYATYYADS</u> <br> <u>VK</u>DRFTISRDDSQSMLYLQMNNLKTEDTAMYYCVR<u>PLKWYF</u> <br> <u>DV</u>WGTGTTVTVSS |
| SYN-04 (VL) | 11 | *ATGGATTTTCAAGTGCAGATTTTCAGCTTCCTGCTAATCAG* <br> *TGCCTCAGTATCCAGAGGA* <br> CAAATTGTTCTCACCCAGTCTCCAGCAAT <br> CTTGTCTGCATCTCCAGGGGAGAAGGTCACCATGACCTGC <br> <u>AGTGCCAGCTCAACTGTTAATTACATGCAC</u>TGGTACCAGC <br> AGAAGTCAGGCACCTCCCCCAAAATATGGATTTAT<u>GACAC</u> <br> <u>ATCCAAACTGGCTTCT</u>GGAGTCCCTGCTCGCTTCAGTGGC <br> AGTGGGTCTTGGACCTCTTACTCTCTCACAATCAGCAGCA <br> TGGAGGCTGAAGATGCTGCCACTTATTACTGC<u>CAGCAGTG</u> <br> <u>GAATAGTAACCCACCCACG</u>TTCGGTGCTGGGACCAAGCT <br> GGAGCTGAAA |
| SYN-04 (VL) | 12 | *MDFQVQIFSFLLISASVSRG* <br> QIVLTQSPAILSASPGEKVTMTC<u>SASS</u> <br> <u>TVNYMH</u>WYQQKSGTSPKIWIY<u>DTSKLAS</u>GVPARFSGSGSW <br> TSYSLTISSMEAEDAATYYC<u>QQWNSNPPT</u>FGAGTKLELK |

The leader sequences are italicised and the CRD regions are underlined.

Example 14

Co-aggregation of α-synuclein in BiFC Culture System

In order to establish the BiFC (bimolecular fluorescence complementation) culture system, SH-SY5Y cells were transfected using electroporation with GN-link-α Syn (V1S) or α SynGC (SV2) (kind gifts from Dr. Pamela McLean, Massachusetts General Hospital, Charlestown, Mass.). Transfected cells were selected with 600 μg/ml G418 (Invitrogen, Carlsbad, Calif.) for 2-3 weeks until colonies emerged. The stable cell lines were maintained with 200 μg/ml G418.

The SV2 cells, stably overexpressing human α-synuclein fused with C-terminal fragment of venus fluorescence protein were co-cultured with V1S stable cell lines overexpressing N-terminal venus fragment tagged α-synuclein in the presence of either 1 μg/ml normal mouse IgG or a α-synuclein antibody (274, Syn-O1, Syn-O2, Syn-F1, Syn-F2, B11D12, F7A11). After 3 days of incubation, the BiFC fluorescence was analyzed with an Olympus (Tokyo, Japan) FV1000 confocal laser scanning microscope.

Figure 18:
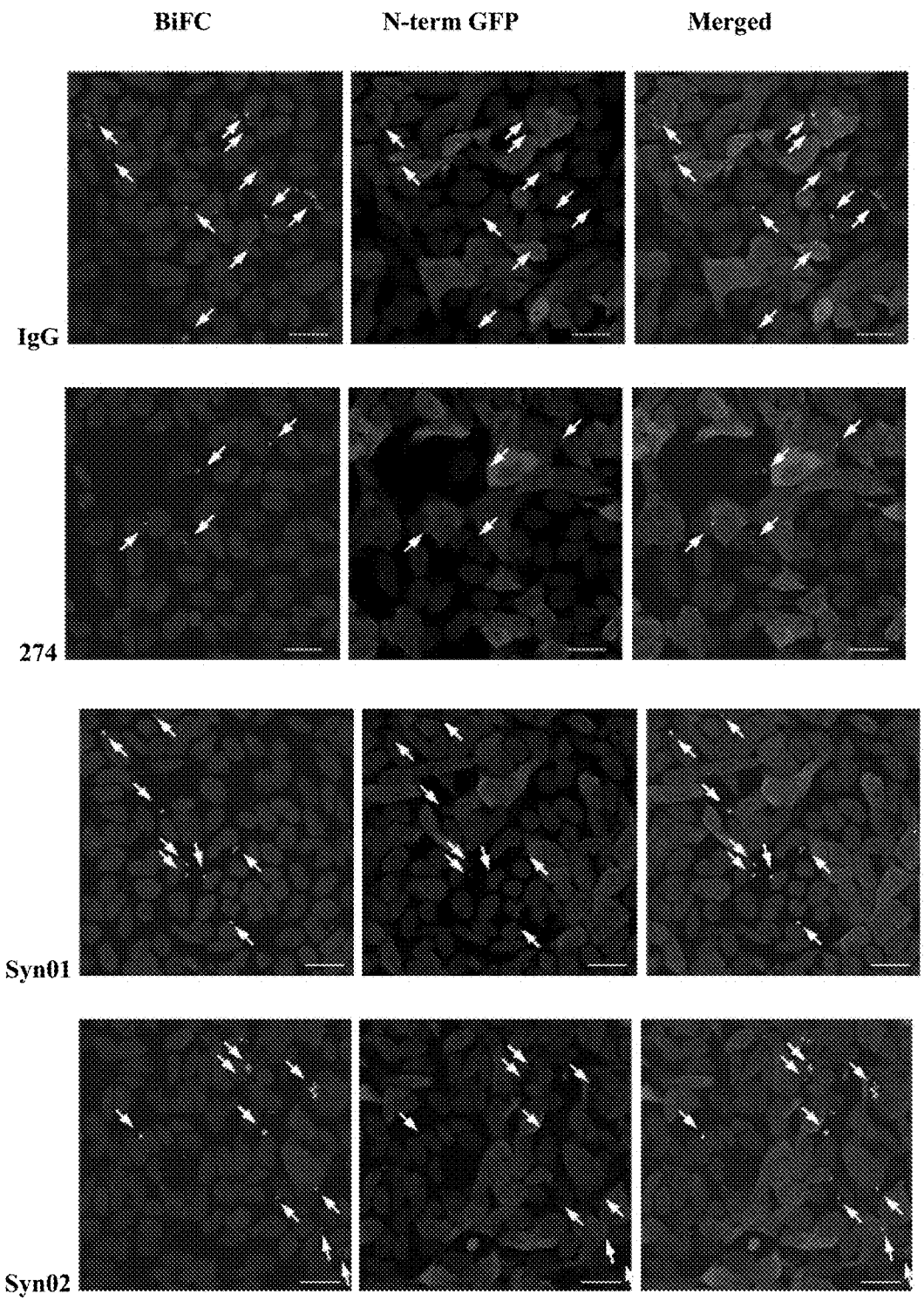
FIG. 18 shows the images obtained showing formation of punct (arrowheads) by BiFC fluorescence analysis as described in Example 14.
Figure 18:
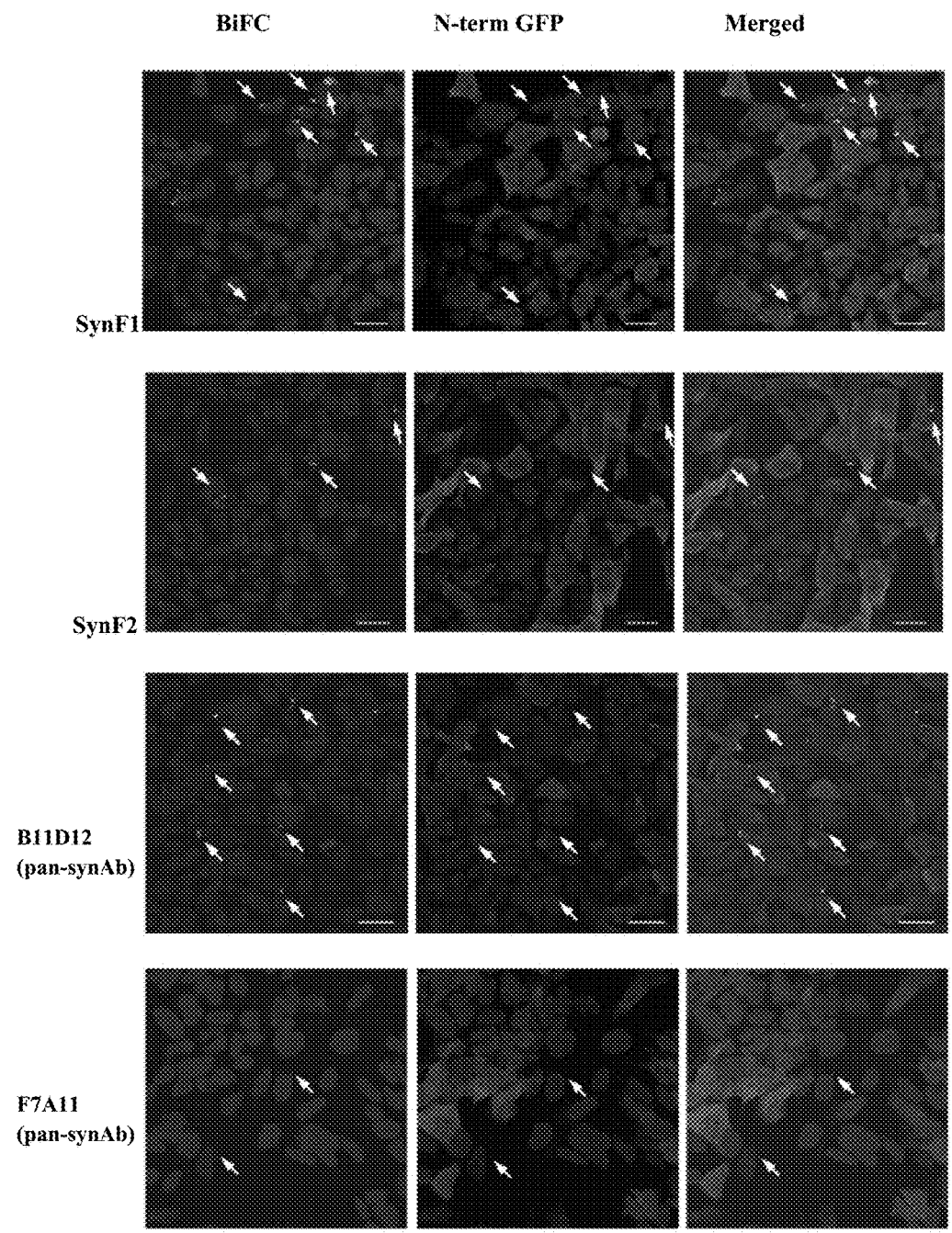
Figures 19, 20:
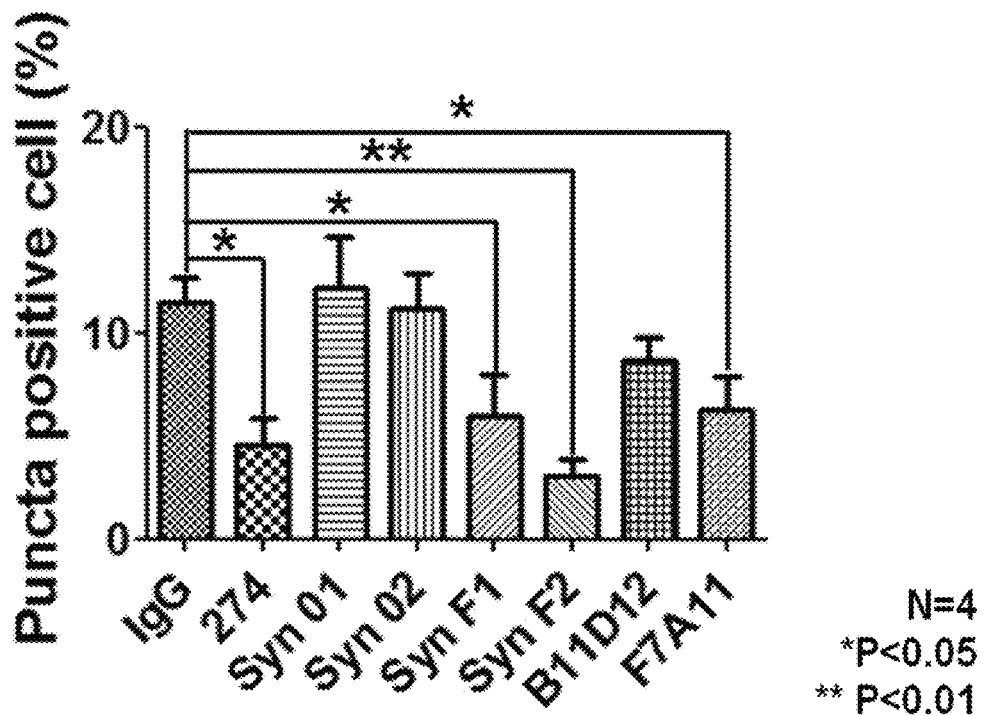
FIG. 19 shows the % of puncta positive cells of each tested antibody as described in Example 14.
FIG. 20 shows the wild-type sequence of human α-synuclein.

Punct formation was observed in cells (arrowheads). The number of cells containing puncta formation were counted and the ratio of punct positive cells was calculated. The results are shown in FIGS. 18 and 19. The graph indicates the percentage of cells containing α-synuclein aggregates. The specific examples and embodiments described herein are exemplary only in nature and are not intending to be limiting of the invention. Further embodiments and examples, and advantages thereof, will be apparent to one of ordinary skill in the art in view of this specification and are within the scope of the claimed invention.

The invention claimed is:

1. A polynucleotide that encodes an amino acid sequence comprising SEQ ID NO:17, SEQ ID NO:18, SEQ ID NO:24, SEQ ID NO:30, SEQ ID NO:36, SEQ ID NO:42, and/or SEQ ID NO:46.

2. The polynucleotide of claim 1 that encodes an amino acid sequence comprising:
SEQ ID NO: 16, SEQ ID NO:28, or SEQ ID NO:40;
SEQ ID NO:17, SEQ ID NO:29, or SEQ ID NO:41; and
SEQ ID NO:18, SEQ ID NO:30, or SEQ ID NO:42.

3. The polynucleotide of claim 1 that encodes an amino acid sequence comprising:
SEQ ID NO:22, SEQ ID NO:34, or SEQ ID NO:46;
SEQ ID NO:23, SEQ ID NO:35, or SEQ ID NO:47; and
SEQ ID NO:24, SEQ ID NO:36, or SEQ ID NO:48.

4. The polynucleotide of claim 1 that encodes an amino acid sequence comprising SEQ ID NO:2, SEQ ID NO:4, SEQ ID NO:6, SEQ ID NO:8, SEQ ID NO:10 or SEQ ID NO:12.

5. The polynucleotide of claim 1 that encodes SEQ ID NO:2, SEQ ID NO:6, or SEQ ID NO:10 and encodes SEQ ID NO:4, SEQ ID NO:8, or SEQ ID NO:12.

6. The polynucleotide of claim 1 that comprises a nucleic acid sequence comprising SEQ ID NO:14, SEQ ID NO:15, SEQ ID NO:21, SEQ ID NO:27, SEQ ID NO:33, SEQ ID NO:38, SEQ ID NO:39, and/or SEQ ID NO:43.

7. The polynucleotide of claim 1 that comprises a nucleic acid sequence comprising:
SEQ ID NO: 13, SEQ ID NO:25, or SEQ ID NO:37;
SEQ ID NO:14, SEQ ID NO:26, or SEQ ID NO:38; and
SEQ ID NO:15, SEQ ID NO:27, or SEQ ID NO:39.

8. The polynucleotide of claim 1 that comprises a nucleic acid sequence comprising:
SEQ ID NO:19, SEQ ID NO:31, or SEQ ID NO:43;
SEQ ID NO:20, SEQ ID NO:32, or SEQ ID NO:44; and
SEQ ID NO:21, SEQ ID NO:33, or SEQ ID NO:45.

9. The polynucleotide of claim 1 that comprises a nucleic acid sequence comprising SEQ ID NO: 13, SEQ ID NO:14, SEQ ID NO:15, SEQ ID NO:19, SEQ ID NO:20 and SEQ ID NO:21.

10. The polynucleotide of claim 1 that comprises a nucleic acid sequence comprising SEQ ID NO:25, SEQ ID NO:26, SEQ ID NO:27, SEQ ID NO:31, SEQ ID NO:32 and SEQ ID NO:33.

11. The polynucleotide of claim 1 that comprises a nucleic acid sequence comprising SEQ ID NO:37, SEQ ID NO:38, SEQ ID NO:39, SEQ ID NO:43, SEQ ID NO:44 and SEQ ID NO:45.

12. The polynucleotide of claim 1 that comprises a nucleic acid sequence comprising SEQ ID NO:1; SEQ ID NO:3, SEQ ID NO:5, SEQ ID NO:7, SEQ ID NO:9 or SEQ ID NO:11.

13. The polynucleotide of claim 1 that comprises a nucleic acid sequence comprising SEQ ID NO:1; SEQ ID NO:5, or SEQ ID NO:9 and SEQ ID NO:3, SEQ ID NO:7, or SEQ ID NO:11.

14. A vector comprising the polynucleotide of claim 1.

15. The vector of claim 14 that further comprises a promoter sequence, a terminator sequence, a polyadenylation sequence and or an enhancer sequence.

16. An isolated host cell that comprises the polynucleotide of claim 1 or the vector of claim 15.

* * * * *

SEQUENCE LISTING

<160> NUMBER OF SEQ ID NOS: 49

<210> SEQ ID NO 1
<211> LENGTH: 426
<212> TYPE: DNA

```
<213> ORGANISM: Homo sapiens
<220> FEATURE:
<221> NAME/KEY: misc_feature
<222> LOCATION: (1)..(57)
<223> OTHER INFORMATION: Leader
<220> FEATURE:
<221> NAME/KEY: misc_feature
<222> LOCATION: (58)..(132)
<223> OTHER INFORMATION: FR1
<220> FEATURE:
<221> NAME/KEY: misc_feature
<222> LOCATION: (123)..(162)
<223> OTHER INFORMATION: CDR1
<220> FEATURE:
<221> NAME/KEY: misc_feature
<222> LOCATION: (163)..(204)
<223> OTHER INFORMATION: FR2
<220> FEATURE:
<221> NAME/KEY: misc_feature
<222> LOCATION: (205)..(255)
<223> OTHER INFORMATION: CDR2
<220> FEATURE:
<221> NAME/KEY: misc_feature
<222> LOCATION: (256)..(351)
<223> OTHER INFORMATION: FR3
<220> FEATURE:
<221> NAME/KEY: misc_feature
<222> LOCATION: (352)..(393)
<223> OTHER INFORMATION: CDR3
<220> FEATURE:
<221> NAME/KEY: misc_feature
<222> LOCATION: (394)..(426)
<223> OTHER INFORMATION: FR4

<400> SEQUENCE: 1
atggactcca ggctcaattt agttttcctt gtccttattt taaaaggtgt ccagtgtgat      60
gtgcagctgg tggagtctgg gggagactta gtgcagcctg agggtcccg gaaactctcc     120 tgtgcagcct ctggattcac tttcagtagc tttggaatgc actgggttcg tcaggctcca     180
gagaaggggc tggagtgggt cgcatacatt aatagtggca gtagtaccat ctactatgca     240
gacacagtga aggccgatt caccatctcc agagacaatc ccaagaacac cctgttcctg      300
cagatgacca gtctaaggtc tgaggacacg gccatgtatt actgtgcaag ggaaataac      360 cctgggacgg gatattacta ttctatggac tactggggtc agggaaccct agtcaccgtc     420
tcctca                                                                 426

<210> SEQ ID NO 2
<211> LENGTH: 142
<212> TYPE: PRT
<213> ORGANISM: Homo sapiens

<400> SEQUENCE: 2

Met Asp Ser Arg Leu Asn Leu Val Phe Leu Val Leu Ile Leu Lys Gly
1               5                   10                  15

Val Gln Cys Asp Val Gln Leu Val Glu Ser Gly Gly Asp Leu Val Gln
            20                  25                  30

Pro Gly Gly Ser Arg Lys Leu Ser Cys Ala Ala Ser Gly Phe Thr Phe
        35                  40                  45

Ser Ser Phe Gly Met His Trp Val Arg Gln Ala Pro Glu Lys Gly Leu
    50                  55                  60

Glu Trp Val Ala Tyr Ile Asn Ser Gly Ser Ser Thr Ile Tyr Tyr Ala
65                  70                  75                  80

Asp Thr Val Lys Gly Arg Phe Thr Ile Ser Arg Asp Asn Pro Lys Asn
                85                  90                  95

Thr Leu Phe Leu Gln Met Thr Ser Leu Arg Ser Glu Asp Thr Ala Met
```

```
                100              105                110
Tyr Tyr Cys Ala Arg Gly Asn Asn Pro Gly Thr Gly Tyr Tyr Tyr Ser
            115                  120                125

Met Asp Tyr Trp Gly Gln Gly Thr Ser Val Thr Val Ser Ser
        130                 135                 140
```

<210> SEQ ID NO 3
<211> LENGTH: 393
<212> TYPE: DNA
<213> ORGANISM: Homo sapiens
<220> FEATURE:
<221> NAME/KEY: misc_feature
<222> LOCATION: (1)..(60)
<223> OTHER INFORMATION: Leader
<220> FEATURE:
<221> NAME/KEY: misc_feature
<222> LOCATION: (61)..(129)
<223> OTHER INFORMATION: FR1
<220> FEATURE:
<221> NAME/KEY: misc_feature
<222> LOCATION: (130)..(177)
<223> OTHER INFORMATION: CDR1
<220> FEATURE:
<221> NAME/KEY: misc_feature
<222> LOCATION: (178)..(222)
<223> OTHER INFORMATION: FR2
<220> FEATURE:
<221> NAME/KEY: misc_feature
<222> LOCATION: (223)..(243)
<223> OTHER INFORMATION: CDR2
<220> FEATURE:
<221> NAME/KEY: misc_feature
<222> LOCATION: (244)..(339)
<223> OTHER INFORMATION: FR3
<220> FEATURE:
<221> NAME/KEY: misc_feature
<222> LOCATION: (340)..(363)
<223> OTHER INFORMATION: CDR3
<220> FEATURE:
<221> NAME/KEY: misc_feature
<222> LOCATION: (364)..(393)
<223> OTHER INFORMATION: FR4

<400> SEQUENCE: 3

```
atgatgagtc ctgcccagtt cctgtttctg ttagtgctct ggattcagga aaccaacggt      60
gatgttgtga tgacccagac tccactcact ttgtcggtta ccattggaca accagcctct     120
atctcttgca gtcaagtca gagcctctta tatagtaatg aaaaaccta tttgaattgg       180 ttattacaga ggccaggcca gtctccaaag cgcctaatct atctggtgtc taaactggac     240
tctggagtcc ctgacaggtt cactggcagt ggatcaggaa cagattttac actgaaaatc     300
agcagagtgg aggctgagga tttgggagtt tattactgcg tgcaaggtac acatttccc      360 acgttcggag tggggaccaa gctggaaata aaa                                  393
```

<210> SEQ ID NO 4
<211> LENGTH: 131
<212> TYPE: PRT
<213> ORGANISM: Homo sapiens

<400> SEQUENCE: 4

```
Met Met Ser Pro Ala Gln Phe Leu Phe Leu Leu Val Leu Trp Ile Gln
1               5                   10                  15

Glu Thr Asn Gly Asp Val Val Met Thr Gln Thr Pro Leu Thr Leu Ser
            20                  25                  30

Val Thr Ile Gly Gln Pro Ala Ser Ile Ser Cys Lys Ser Ser Gln Ser
        35                  40                  45
```

Leu Leu Tyr Ser Asn Gly Lys Thr Tyr Leu Asn Trp Leu Leu Gln Arg
    50                  55                  60

Pro Gly Gln Ser Pro Lys Arg Leu Ile Tyr Leu Val Ser Lys Leu Asp
65                  70                  75                  80

Ser Gly Val Pro Asp Arg Phe Thr Gly Ser Gly Ser Gly Thr Asp Phe
                85                  90                  95

Thr Leu Lys Ile Ser Arg Val Glu Ala Glu Asp Leu Gly Val Tyr Tyr
            100                 105                 110

Cys Val Gln Gly Thr His Phe Pro Thr Phe Gly Val Gly Thr Lys Leu
            115                 120                 125

Glu Ile Lys
    130

<210> SEQ ID NO 5
<211> LENGTH: 426
<212> TYPE: DNA
<213> ORGANISM: Homo sapiens
<220> FEATURE:
<221> NAME/KEY: misc_feature
<222> LOCATION: (1)..(57)
<223> OTHER INFORMATION: Leader
<220> FEATURE:
<221> NAME/KEY: misc_feature
<222> LOCATION: (58)..(132)
<223> OTHER INFORMATION: FR1
<220> FEATURE:
<221> NAME/KEY: misc_feature
<222> LOCATION: (133)..(162)
<223> OTHER INFORMATION: CDR1
<220> FEATURE:
<221> NAME/KEY: misc_feature
<222> LOCATION: (163)..(204)
<223> OTHER INFORMATION: FR2
<220> FEATURE:
<221> NAME/KEY: misc_feature
<222> LOCATION: (205)..(255)
<223> OTHER INFORMATION: CDR2
<220> FEATURE:
<221> NAME/KEY: misc_feature
<222> LOCATION: (256)..(351)
<223> OTHER INFORMATION: FR3
<220> FEATURE:
<221> NAME/KEY: misc_feature
<222> LOCATION: (352)..(393)
<223> OTHER INFORMATION: CDR3
<220> FEATURE:
<221> NAME/KEY: misc_feature
<222> LOCATION: (394)..(426)
<223> OTHER INFORMATION: FR4

<400> SEQUENCE: 5
atggactcca ggctcaattt agttttcctt gtccttattt taaaaggtgt ccagtgtgat      60
gtgcagctgg tggagtctgg gggaggctta gtgcagcctg agggtcccg gaaactctcc     120 tgtgcagcct ctggattcac tttcagtagc tttggaatgc actgggttcg tcaggctcca     180
gagaaggggc tggagtgggt cgcatacatt agtagtggca gtagtaccat ctactatgca     240
gacacagtga agggccgatt caccatctcc agagacaatc ccaagaacac cctgttcctg     300
caaatgacca gtctaaggtc tgaggacacg gccatgtatt actgtgcaag aggaaataac     360
cctgggacgg atattacta tgctatggac tactggggtc aaggaacctc agtcaccgtc     420
tcctca                                                                426

<210> SEQ ID NO 6
<211> LENGTH: 142
<212> TYPE: PRT
<213> ORGANISM: Homo sapiens

<400> SEQUENCE: 6

Met Asp Ser Arg Leu Asn Leu Val Phe Leu Val Leu Ile Leu Lys Gly
1               5                   10                  15

Val Gln Cys Asp Val Gln Leu Val Glu Ser Gly Gly Gly Leu Val Gln
            20                  25                  30

Pro Gly Gly Ser Arg Lys Leu Ser Cys Ala Ala Ser Gly Phe Thr Phe
        35                  40                  45

Ser Ser Phe Gly Met His Trp Val Arg Gln Ala Pro Glu Lys Gly Leu
    50                  55                  60

Glu Trp Val Ala Tyr Ile Ser Ser Gly Ser Ser Thr Ile Tyr Tyr Ala
65                  70                  75                  80

Asp Thr Val Lys Gly Arg Phe Thr Ile Ser Arg Asp Asn Pro Lys Asn
                85                  90                  95

Thr Leu Phe Leu Gln Met Thr Ser Leu Arg Ser Glu Asp Thr Ala Met
            100                 105                 110

Tyr Tyr Cys Ala Arg Gly Asn Asn Pro Gly Thr Gly Tyr Tyr Tyr Ala
        115                 120                 125

Met Asp Tyr Trp Gly Gln Gly Thr Ser Val Thr Val Ser Ser
130                 135                 140

<210> SEQ ID NO 7
<211> LENGTH: 393
<212> TYPE: DNA
<213> ORGANISM: Homo sapiens
<220> FEATURE:
<221> NAME/KEY: misc_feature
<222> LOCATION: (1)..(60)
<223> OTHER INFORMATION: Leader
<220> FEATURE:
<221> NAME/KEY: misc_feature
<222> LOCATION: (61)..(129)
<223> OTHER INFORMATION: FR1
<220> FEATURE:
<221> NAME/KEY: misc_feature
<222> LOCATION: (130)..(177)
<223> OTHER INFORMATION: CDR1
<220> FEATURE:
<221> NAME/KEY: misc_feature
<222> LOCATION: (178)..(222)
<223> OTHER INFORMATION: FR2
<220> FEATURE:
<221> NAME/KEY: misc_feature
<222> LOCATION: (223)..(243)
<223> OTHER INFORMATION: CDR2
<220> FEATURE:
<221> NAME/KEY: misc_feature
<222> LOCATION: (244)..(339)
<223> OTHER INFORMATION: FR3
<220> FEATURE:
<221> NAME/KEY: misc_feature
<222> LOCATION: (340)..(363)
<223> OTHER INFORMATION: CDR3
<220> FEATURE:
<221> NAME/KEY: misc_feature
<222> LOCATION: (364)..(393)
<223> OTHER INFORMATION: FR4

<400> SEQUENCE: 7
atgatgagtc ctgcccagtt cctgtttctg ttagtgctct ggattcagga aaccaacggt     60
gatgttgtga tgacccagac tccactcact ttgtcggtta ccattggaca accagcctct    120
atctcttgca gtcaagtca gagcctctta tatagtaatg gaaaaaccta tttgaattgg    180
ttattacaga ggccaggcca gtctccaaag cgcctaatct atctggtgtc taaactggac    240
tctggagtcc ctgacaggtt cactggcagt ggatcaggaa cagattttac actgaaaatc    300
agcagagtgg aggctgagga tttgggagtt tattactgcg tgcaaggtac acattttccc    360
acgttcggag gggggaccaa gctggaaata aaa                                 393

<210> SEQ ID NO 8
<211> LENGTH: 131
<212> TYPE: PRT
<213> ORGANISM: Homo sapiens

<400> SEQUENCE: 8

Met Met Ser Pro Ala Gln Phe Leu Phe Leu Leu Val Leu Trp Ile Gln
1               5                   10                  15

Glu Thr Asn Gly Asp Val Val Met Thr Gln Thr Pro Leu Thr Leu Ser
            20                  25                  30

Val Thr Ile Gly Gln Pro Ala Ser Ile Ser Cys Lys Ser Ser Gln Ser
        35                  40                  45

Leu Leu Tyr Ser Asn Gly Lys Thr Tyr Leu Asn Trp Leu Leu Gln Arg
    50                  55                  60

Pro Gly Gln Ser Pro Lys Arg Leu Ile Tyr Leu Val Ser Lys Leu Asp
65                  70                  75                  80

Ser Gly Val Pro Asp Arg Phe Thr Gly Ser Gly Ser Gly Thr Asp Phe
                85                  90                  95

Thr Leu Lys Ile Ser Arg Val Glu Ala Glu Asp Leu Gly Val Tyr Tyr
            100                 105                 110

Cys Val Gln Gly Thr His Phe Pro Thr Phe Gly Gly Gly Thr Lys Leu
        115                 120                 125

Glu Ile Lys
    130

<210> SEQ ID NO 9
<211> LENGTH: 414
<212> TYPE: DNA
<213> ORGANISM: Homo sapiens
<220> FEATURE:
<221> NAME/KEY: misc_feature
<222> LOCATION: (1)..(57)
<223> OTHER INFORMATION: Leader
<220> FEATURE:
<221> NAME/KEY: misc_feature
<222> LOCATION: (58)..(132)
<223> OTHER INFORMATION: FR1
<220> FEATURE:
<221> NAME/KEY: misc_feature
<222> LOCATION: (133)..(162)
<223> OTHER INFORMATION: CDR1
<220> FEATURE:
<221> NAME/KEY: misc_feature
<222> LOCATION: (163)..(204)
<223> OTHER INFORMATION: FR2
<220> FEATURE:
<221> NAME/KEY: misc_feature
<222> LOCATION: (205)..(261)
<223> OTHER INFORMATION: CDR2
<220> FEATURE:
<221> NAME/KEY: misc_feature
<222> LOCATION: (262)..(357)
<223> OTHER INFORMATION: FR3
<220> FEATURE:
<221> NAME/KEY: misc_feature
<222> LOCATION: (358)..(381)
<223> OTHER INFORMATION: CDR3
<220> FEATURE:
<221> NAME/KEY: misc_feature
<222> LOCATION: (382)..(414)
<223> OTHER INFORMATION: FR4

<400> SEQUENCE: 9

```
atggtgttgg ggcttaagtg ggttttcttt gttgtttttt atcaaggtgt gcattgtgag      60
gtgcagcttg ttgagtctgg tggaggattg gtgcagccta aggatcatt gaaactctca      120 tgtgccgcct ctggtttcac cttcaatacc tatgccatgc actgggtccg ccaggctcca     180
ggaaagggtt tggaatgggt tgctcgcata agaagtaaaa gtagtaatta tgcaacatat     240
tatgccgact cagtgaaaga cagattcacc atctccagag atgattcaca aagcatgctc     300
tatctgcaaa tgaacaacct gaaaactgag gacacagcca tgtattactg tgtgagaccc     360
cttaagtggt acttcgatgt ctggggcaca gggaccacgg tcaccgtctc ctca           414
```

<210> SEQ ID NO 10
<211> LENGTH: 138
<212> TYPE: PRT
<213> ORGANISM: Homo sapiens

<400> SEQUENCE: 10

```
Met Val Leu Gly Leu Lys Trp Val Phe Phe Val Val Phe Tyr Gln Gly
1               5                   10                  15

Val His Cys Glu Val Gln Leu Val Glu Ser Gly Gly Gly Leu Val Gln
            20                  25                  30

Pro Lys Gly Ser Leu Lys Leu Ser Cys Ala Ala Ser Gly Phe Thr Phe
        35                  40                  45

Asn Thr Tyr Ala Met His Trp Val Arg Gln Ala Pro Gly Lys Gly Leu
    50                  55                  60

Glu Trp Val Ala Arg Ile Arg Ser Lys Ser Ser Asn Tyr Ala Thr Tyr
65                  70                  75                  80

Tyr Ala Asp Ser Val Lys Asp Arg Phe Thr Ile Ser Arg Asp Asp Ser
                85                  90                  95

Gln Ser Met Leu Tyr Leu Gln Met Asn Asn Leu Lys Thr Glu Asp Thr
            100                 105                 110

Ala Met Tyr Tyr Cys Val Arg Pro Leu Lys Trp Tyr Phe Asp Val Trp
        115                 120                 125

Gly Thr Gly Thr Thr Val Thr Val Ser Ser
    130                 135
```

<210> SEQ ID NO 11
<211> LENGTH: 378
<212> TYPE: DNA
<213> ORGANISM: Homo sapiens
<220> FEATURE:
<221> NAME/KEY: misc_feature
<222> LOCATION: (1)..(60)
<223> OTHER INFORMATION: Leader
<220> FEATURE:
<221> NAME/KEY: misc_feature
<222> LOCATION: (61)..(129)
<223> OTHER INFORMATION: FR1
<220> FEATURE:
<221> NAME/KEY: misc_feature
<222> LOCATION: (130)..(159)
<223> OTHER INFORMATION: CDR1
<220> FEATURE:
<221> NAME/KEY: misc_feature
<222> LOCATION: (160)..(204)
<223> OTHER INFORMATION: FR2
<220> FEATURE:
<221> NAME/KEY: misc_feature
<222> LOCATION: (205)..(225)
<223> OTHER INFORMATION: CDR2
<220> FEATURE:
<221> NAME/KEY: misc_feature
<222> LOCATION: (226)..(321)
<223> OTHER INFORMATION: FR3

```
<220> FEATURE:
<221> NAME/KEY: misc_feature
<222> LOCATION: (322)..(348)
<223> OTHER INFORMATION: CDR3
<220> FEATURE:
<221> NAME/KEY: misc_feature
<222> LOCATION: (349)..(378)
<223> OTHER INFORMATION: FR4

<400> SEQUENCE: 11
atggattttc aagtgcagat tttcagcttc ctgctaatca gtgcctcagt atccagagga    60
caaattgttc tcacccagtc tccagcaatc ttgtctgcat ctccagggga gaaggtcacc   120
atgacctgca gtgccagctc aactgttaat tacatgcact ggtaccagca gaagtcaggc   180
acctccccca aaatatggat ttatgacaca tccaaactgg cttctggagt ccctgctcgc   240
ttcagtggca gtgggtcttg gacctcttac tctctcacaa tcagcagcat ggaggctgaa   300
gatgctgcca cttattactg ccagcagtgg aatagtaacc cacccacgtt cggtgctggg   360
accaagctgg agctgaaa                                                 378

<210> SEQ ID NO 12
<211> LENGTH: 126
<212> TYPE: PRT
<213> ORGANISM: Homo sapiens

<400> SEQUENCE: 12

Met Asp Phe Gln Val Gln Ile Phe Ser Phe Leu Leu Ile Ser Ala Ser
1               5                   10                  15

Val Ser Arg Gly Gln Ile Val Leu Thr Gln Ser Pro Ala Ile Leu Ser
            20                  25                  30

Ala Ser Pro Gly Glu Lys Val Thr Met Thr Cys Ser Ala Ser Ser Thr
        35                  40                  45

Val Asn Tyr Met His Trp Tyr Gln Gln Lys Ser Gly Thr Ser Pro Lys
    50                  55                  60

Ile Trp Ile Tyr Asp Thr Ser Lys Leu Ala Ser Gly Val Pro Ala Arg
65                  70                  75                  80

Phe Ser Gly Ser Gly Ser Trp Thr Ser Tyr Ser Leu Thr Ile Ser Ser
                85                  90                  95

Met Glu Ala Glu Asp Ala Ala Thr Tyr Tyr Cys Gln Gln Trp Asn Ser
            100                 105                 110

Asn Pro Pro Thr Phe Gly Ala Gly Thr Lys Leu Glu Leu Lys
        115                 120                 125

<210> SEQ ID NO 13
<211> LENGTH: 30
<212> TYPE: DNA
<213> ORGANISM: Homo sapiens

<400> SEQUENCE: 13
ggattcactt tcagtagctt tggaatgcac                                     30

<210> SEQ ID NO 14
<211> LENGTH: 51
<212> TYPE: DNA
<213> ORGANISM: Homo sapiens

<400> SEQUENCE: 14
tacattaata gtggcagtag taccatctac tatgcagaca cagtgaaggg c             51

<210> SEQ ID NO 15
```

-continued

<211> LENGTH: 42
<212> TYPE: DNA
<213> ORGANISM: Homo sapiens

<400> SEQUENCE: 15
ggaaataacc ctgggacggg atattactat tctatggact ac                             42

<210> SEQ ID NO 16
<211> LENGTH: 10
<212> TYPE: PRT
<213> ORGANISM: Homo sapiens

<400> SEQUENCE: 16

Gly Phe Thr Phe Ser Ser Phe Gly Met His
1               5                   10

<210> SEQ ID NO 17
<211> LENGTH: 17
<212> TYPE: PRT
<213> ORGANISM: Homo sapiens

<400> SEQUENCE: 17

Tyr Ile Asn Ser Gly Ser Ser Thr Ile Tyr Tyr Ala Asp Thr Val Lys
1               5                   10                  15
Gly

<210> SEQ ID NO 18
<211> LENGTH: 14
<212> TYPE: PRT
<213> ORGANISM: Homo sapiens

<400> SEQUENCE: 18

Gly Asn Asn Pro Gly Thr Gly Tyr Tyr Tyr Ser Met Asp Tyr
1               5                   10

<210> SEQ ID NO 19
<211> LENGTH: 48
<212> TYPE: DNA
<213> ORGANISM: Homo sapiens

<400> SEQUENCE: 19
aagtcaagtc agagcctctt atatagtaat ggaaaaacct atttgaat                       48

<210> SEQ ID NO 20
<211> LENGTH: 21
<212> TYPE: DNA
<213> ORGANISM: Homo sapiens

<400> SEQUENCE: 20
ctggtgtcta aactggactc t                                                    21

<210> SEQ ID NO 21
<211> LENGTH: 24
<212> TYPE: DNA
<213> ORGANISM: Homo sapiens

<400> SEQUENCE: 21
gtgcaaggta cacattttcc cacg                                                 24

<210> SEQ ID NO 22
<211> LENGTH: 16
<212> TYPE: PRT
<213> ORGANISM: Homo sapiens

<400> SEQUENCE: 22

Lys Ser Ser Gln Ser Leu Leu Tyr Ser Asn Gly Lys Thr Tyr Leu Asn
1               5                   10                  15

<210> SEQ ID NO 23
<211> LENGTH: 7
<212> TYPE: PRT
<213> ORGANISM: Homo sapiens

<400> SEQUENCE: 23

Leu Val Ser Lys Leu Asp Ser
1               5

<210> SEQ ID NO 24
<211> LENGTH: 8
<212> TYPE: PRT
<213> ORGANISM: Homo sapiens

<400> SEQUENCE: 24

Val Gln Gly Thr His Phe Pro Thr
1               5

<210> SEQ ID NO 25
<211> LENGTH: 30
<212> TYPE: DNA
<213> ORGANISM: Homo sapiens

<400> SEQUENCE: 25
ggattcactt tcagtagctt tggaatgcac                                       30

<210> SEQ ID NO 26
<211> LENGTH: 51
<212> TYPE: DNA
<213> ORGANISM: Homo sapiens

<400> SEQUENCE: 26
tacattagta gtggcagtag taccatctac tatgcagaca cagtgaaggg c               51

<210> SEQ ID NO 27
<211> LENGTH: 42
<212> TYPE: DNA
<213> ORGANISM: Homo sapiens

<400> SEQUENCE: 27
ggaaataacc ctgggacggg atattactat gctatggact ac                         42

<210> SEQ ID NO 28
<211> LENGTH: 10
<212> TYPE: PRT
<213> ORGANISM: Homo sapiens

<400> SEQUENCE: 28

Gly Phe Thr Phe Ser Ser Phe Gly Met His
1               5                   10

<210> SEQ ID NO 29
<211> LENGTH: 17
<212> TYPE: PRT
<213> ORGANISM: Homo sapiens

<400> SEQUENCE: 29

Tyr Ile Ser Ser Gly Ser Ser Thr Ile Tyr Tyr Ala Asp Thr Val Lys
1               5                   10                  15

Gly

<210> SEQ ID NO 30
<211> LENGTH: 14
<212> TYPE: PRT
<213> ORGANISM: Homo sapiens

<400> SEQUENCE: 30

Gly Asn Asn Pro Gly Thr Gly Tyr Tyr Tyr Ala Met Asp Tyr
1               5                   10

<210> SEQ ID NO 31
<211> LENGTH: 48
<212> TYPE: DNA
<213> ORGANISM: Homo sapiens

<400> SEQUENCE: 31
aagtcaagtc agagcctctt atatagtaat ggaaaaacct atttgaat                    48

<210> SEQ ID NO 32
<211> LENGTH: 21
<212> TYPE: DNA
<213> ORGANISM: Homo sapiens

<400> SEQUENCE: 32
ctggtgtcta aactggactc t                                                 21

<210> SEQ ID NO 33
<211> LENGTH: 24
<212> TYPE: DNA
<213> ORGANISM: Homo sapiens

<400> SEQUENCE: 33
gtgcaaggta cacattttcc cacg                                              24

<210> SEQ ID NO 34
<211> LENGTH: 16
<212> TYPE: PRT
<213> ORGANISM: Homo sapiens

<400> SEQUENCE: 34

Lys Ser Ser Gln Ser Leu Leu Tyr Ser Asn Gly Lys Thr Tyr Leu Asn
1               5                   10                  15

<210> SEQ ID NO 35
<211> LENGTH: 7
<212> TYPE: PRT
<213> ORGANISM: Homo sapiens

<400> SEQUENCE: 35

Leu Val Ser Lys Leu Asp Ser
1               5

<210> SEQ ID NO 36
<211> LENGTH: 8
<212> TYPE: PRT
<213> ORGANISM: Homo sapiens

<400> SEQUENCE: 36

Val Gln Gly Thr His Phe Pro Thr
1               5

<210> SEQ ID NO 37
<211> LENGTH: 30

<212> TYPE: DNA
<213> ORGANISM: Homo sapiens

<400> SEQUENCE: 37
ggtttcacct tcaataccta tgccatgcac                              30

<210> SEQ ID NO 38
<211> LENGTH: 57
<212> TYPE: DNA
<213> ORGANISM: Homo sapiens

<400> SEQUENCE: 38
cgcataagaa gtaaaagtag taattatgca acatattatg ccgactcagt gaaagac    57

<210> SEQ ID NO 39
<211> LENGTH: 24
<212> TYPE: DNA
<213> ORGANISM: Homo sapiens

<400> SEQUENCE: 39 cccccttaagt ggtacttcga tgtc                                  24

<210> SEQ ID NO 40
<211> LENGTH: 10
<212> TYPE: PRT
<213> ORGANISM: Homo sapiens

<400> SEQUENCE: 40

Gly Phe Thr Phe Asn Thr Tyr Ala Met His
1               5                   10

<210> SEQ ID NO 41
<211> LENGTH: 19
<212> TYPE: PRT
<213> ORGANISM: Homo sapiens

<400> SEQUENCE: 41

Arg Ile Arg Ser Lys Ser Ser Asn Tyr Ala Thr Tyr Tyr Ala Asp Ser
1               5                   10                  15

Val Lys Asp

<210> SEQ ID NO 42
<211> LENGTH: 8
<212> TYPE: PRT
<213> ORGANISM: Homo sapiens

<400> SEQUENCE: 42

Pro Leu Lys Trp Tyr Phe Asp Val
1               5

<210> SEQ ID NO 43
<211> LENGTH: 30
<212> TYPE: DNA
<213> ORGANISM: Homo sapiens

<400> SEQUENCE: 43
agtgccagct caactgttaa ttacatgcac                              30

<210> SEQ ID NO 44
<211> LENGTH: 21
<212> TYPE: DNA
<213> ORGANISM: Homo sapiens

<400> SEQUENCE: 44

```
gacacatcca aactggcttc t                                              21
```

<210> SEQ ID NO 45
<211> LENGTH: 27
<212> TYPE: DNA
<213> ORGANISM: Homo sapiens

<400> SEQUENCE: 45

```
cagcagtgga atagtaaccc acccacg                                        27
```

<210> SEQ ID NO 46
<211> LENGTH: 10
<212> TYPE: PRT
<213> ORGANISM: Homo sapiens

<400> SEQUENCE: 46

```
Ser Ala Ser Ser Thr Val Asn Tyr Met His
1               5                   10
```

<210> SEQ ID NO 47
<211> LENGTH: 7
<212> TYPE: PRT
<213> ORGANISM: Homo sapiens

<400> SEQUENCE: 47

```
Asp Thr Ser Lys Leu Ala Ser
1               5
```

<210> SEQ ID NO 48
<211> LENGTH: 9
<212> TYPE: PRT
<213> ORGANISM: Homo sapiens

<400> SEQUENCE: 48

```
Gln Gln Trp Asn Ser Asn Pro Pro Thr
1               5
```

<210> SEQ ID NO 49
<211> LENGTH: 140
<212> TYPE: PRT
<213> ORGANISM: Homo sapiens

<400> SEQUENCE: 49

```
Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
                20                  25                  30

Thr Lys Glu Gly Val Leu Tyr Val Gly Ser Lys Thr Lys Glu Gly Val
            35                  40                  45

Val His Gly Val Ala Thr Val Ala Glu Lys Thr Lys Glu Gln Val Thr
        50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
                100                 105                 110
```

```
Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140
```